US006291190B1

(12) United States Patent
Behr et al.

(10) Patent No.: US 6,291,190 B1
(45) Date of Patent: Sep. 18, 2001

(54) **MOLECULAR DIFFERENCES BETWEEN SPECIES OF THE *M. TUBERCULOSIS* COMPLEX**

(75) Inventors: Marcel Behr, Montreal (CA); Peter Small, Stanford, CA (US); Gary Schoolnik, Stanford, CA (US); Michael A. Wilson, Stanford, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 0 days.

(21) Appl. No.: 09/318,191

(22) Filed: May 25, 1999

Related U.S. Application Data
(60) Provisional application No. 60/097,936, filed on Aug. 25, 1998.

(51) Int. Cl.[7] .......................... G01N 33/53; A61K 39/00; A61K 39/02; C12Q 1/00; C12Q 1/68
(52) U.S. Cl. .......................... 435/7.1; 435/4; 424/184.1; 424/190.1; 436/501; 436/517; 436/518; 436/536
(58) Field of Search ................ 435/6, 7.1, 4; 424/184.1, 424/190.1, 9; 436/501, 517, 518, 536

(56) References Cited

U.S. PATENT DOCUMENTS
| | | |
|---|---|---|
| 5,686,597 | 11/1997 | Coleman et al. |
| 5,776,465 | 7/1998 | O'Donnell et al. ................ 424/200.1 |
| 5,955,356 * | 9/1999 | Content et al. ........................ 435/325 |

FOREIGN PATENT DOCUMENTS
| | | |
|---|---|---|
| WO 96/27129 | 2/1996 | (WO) . |
| 96/25519 | 8/1996 | (WO) . |

OTHER PUBLICATIONS

Brosch, et al. *Infection and Immunity*, vol. 66, No. 5 pp. 2221–2229, May 1998.*
Gordon, et al. *Molecular Microbiology*, vol. 32, No. 3 pp. 643–655, Apr. 1999.*
Behr, et al. *Science*, vol. 284 pp1520–1523, May 1999.*
Aldovini, et al., (1993) *Journal of Bacteriology*, vol. 175, No. (22):7282–7289.
Cole, et al. (1998) *Nature*, vol. 393:537–544.
Converse, et al., (1996) *Infection and Immunity*, vol. 64, No. (11):4776–4787.
Delahunty, et al., (1996) *American Journal of Human Genetics*, vol. 58:1239–1246.
DeRisi, et al., (1996) *Nature Genetics*, vol. 14, No. (4):457–460.
Ganjam, et al., (1991) *Proceedings of the National Academy of Sciences*, vol. 88, No. (12):5433–5437.
Hacia, et al., (1996) *Nature Genetics*, vol. 14, No. (4):441–447.
Jost, et al., (1994) *Journal of Biological Chemistry*, vol. 269, No. (42):26267–26273.
Lockhart, et al., (1996) *Nature Biotechnology*, vol. 14, No. (13):1675–1680.
Mahairas, et al., (1996) *Journal of Bacteriology*, vol. 178, No. (5):1274–1282.
Norman, et al., (1995) *Molecular Microbiology*, vol. 16, No. (4):755–760.
Paul, et al., (1996) *Journal of Infectious Diseases*, vol. 174, No. (1):105–112.
Ramsay, et al., (1998) *Nature Biotechnology*, vol. 16, No. (1):40–44.
Riley, et al., (1990) *Nucleic Acids Research*, vol. 18, No. (10):2887–2890.
Saiki, et al., (1988) *Science*, vol. 239:487–491.
Sambrook, et al., *Molecular Cloning: A Laboratory Manual*, CSH Press (1989), pp:14.2–14.35.
Shalon, et al., (1996) *Genome Research*, vol. 6, No. (7):639–645.
Silver, et al., (1998) *Infection and Immunology*, vol. 66, No. (3):1190–1199.
Talbot, et al., (1997) *Journal of Clinical Microbiology*, vol. 35, No. (3):566–569.
Philip, Wolfgang J., et al., "Physical Mapping of *Mycobacterium bovis* BCG Pasteur Reveals Differences from the Genome Map of *Mycobacterium tuberculosis* H37Rv and from *M. bovis*," *Microbiology* (1996) vol. 142:3135–3145.

* cited by examiner

Primary Examiner—David Guzo
Assistant Examiner—Gerald G. Leffers, Jr.
(74) *Attorney, Agent, or Firm*—Pamela J. Sherwood; Bozicevic, Field & Francis LLP

(57) ABSTRACT

Specific genetic deletions are identified in mycobacteria isolates, including variations in the *M. tuberculosis* genome sequence between isolates, and numerous deletion present in BCG as compared to *M. tb*. These deletions are used as markers to distinguish between pathogenic and avirulent strains, and as a marker for particular *M. tb* isolates. Deletions specific to vaccine strains of BCG are useful in determining whether a positive tuberculin skin test is indicative of actual tuberculosis infection. The deleted sequences may be re-introduced into BCG to improve the efficacy of vaccination. Alternatively, the genetic sequence that corresponds to the deletion(s) are deleted from *M. bovis* or *M. tuberculosis* to attenuate the pathogenic bacteria.

5 Claims, No Drawings

SEQUENCE LISTING

```
<160> NUMBER OF SEQ ID NOS:  137

<210> SEQ ID NO 1
<211> LENGTH: 1773
<212> TYPE: DNA
<213> ORGANISM: Mycobacteria tuberculosis
<220> FEATURE:
<221> NAME/KEY: CDS
<222> LOCATION: (0)...(0)

<400> SEQUENCE: 1
atgactgctg aaccggaagt acggacgctg cgcgaggttg tgctggacca gctcggcact        60
gctgaatcgc gtgcgtacaa gatgtggctg ccgccgttga ccaatccggt cccgctcaac       120
gagctcatcg cccgtgatcg gcgacaaccc ctgcgatttg ccctggggat catggatgaa       180
ccgcgccgcc atctacagga tgtgtggggc gtagacgttt ccggggccgg cggcaacatc       240
```

-continued

| | |
|---|---|
| ggtattgggg gcgcacctca aaccgggaag tcgacgctac tgcagacgat ggtgatgtcg | 300 |
| gccgccgcca cacactcacc gcgcaacgtt cagttctatt gcatcgacct aggtggcggc | 360 |
| gggctgatct atctcgaaaa ccttccacac gtcggtgggg tagccaatcg gtccgagccc | 420 |
| gacaaggtca accgggtggt cgcagagatg caagccgtca tgcggcaacg ggaaaccacc | 480 |
| ttcaaggaac accgagtggg ctcgatcggg atgtaccggc agctgcgtga cgatccaagt | 540 |
| caacccgttg cgtccgatcc atacggcgac gtctttctga tcatcgacgg atggcccggt | 600 |
| tttgtcggcg agttccccga ccttgagggg caggttcaag atctggccgc caggggctg | 660 |
| gcgttcggcg tccacgtcat catctccacg ccacgctgga cagagctgaa gtcgcgtgtt | 720 |
| cgcgactacc tcggcaccaa gatcgagttc cggcttggtg acgtcaatga acccagatc | 780 |
| gaccggatta cccgcgagat cccggcgaat cgtccgggtc gggcagtgtc gatggaaaag | 840 |
| caccatctga tgatcggcgt gcccaggttc gacggcgtgc acagcgccga taacctggtg | 900 |
| gaggcgatca ccgcggggt gacgcagatc gcttcccagc acaccgaaca ggcacctccg | 960 |
| gtgcgggtcc tgccggagcg tatccacctg cacgaactcg acccgaaccc gccgggacca | 1020 |
| gagtccgact accgcactcg ctgggagatt ccgatcggct gcgcgagac ggacctgacg | 1080 |
| ccggctcact gccacatgca cacgaacccg cacctactga tcttcggtgc ggccaaatcg | 1140 |
| ggcaagacga ccattgccca cgcgatcgcg cgcgccattt gtgcccgaaa cagtccccag | 1200 |
| caggtgcggt tcatgctcgc ggactaccgc tcgggcctgc tggacgcggt gccggacacc | 1260 |
| catctgctgg gcgccggcgc gatcaaccgc aacagcgcgt cgctagacga ggccgttcaa | 1320 |
| gcactggcgg tcaacctgaa gaagcggttg ccgccgaccg acctgacgac ggcgcagcta | 1380 |
| cgctcgcgtt cgtggtggag cggatttgac gtcgtgcttc tggtcgacga ttggcacatg | 1440 |
| atcgtgggtg ccgccggggg gatgccgccg atggcaccgc tggccccgtt attgccggcg | 1500 |
| gcggcagata tcgggttgca catcattgtc acctgtcaga tgagccaggc ttacaaggca | 1560 |
| accatggaca agttcgtcgg cgccgcattc gggtcgggcg ctccgacaat gttccttcg | 1620 |
| ggcgagaagc aggaattccc atccagtgag ttcaaggtca agcggcgccc ccctggccag | 1680 |
| gcatttctcg tctcgccaga cggcaaagag gtcatccagg cccctacat cgagcctcca | 1740 |
| gaagaagtgt tcgcagcacc cccaagcgcc ggt | 1773 |

```
<210> SEQ ID NO 2
<211> LENGTH: 297
<212> TYPE: DNA
<213> ORGANISM: Mycobacteria tuberculosis

<400> SEQUENCE: 2
```

| | |
|---|---|
| atggaaaaaa tgtcacatga tccgatcgct gccgacattg gcacgcaagt gagcgacaac | 60 |
| gctctgcacg gcgtgacggc cggctcgacg gcgctgacgt cggtgaccgg gctggttccc | 120 |
| gcggggccg atgaggtctc cgcccaagcg gcgacggcgt tcacatcgga gggcatccaa | 180 |
| ttgctggctt ccaatgcatc ggcccaagac cagctccacc gtgcgggcga agcggtccag | 240 |
| gacgtcgccc gcacctattc gcaaatcgac gacggcgccg ccggcgtctt cgccgaa | 297 |

```
<210> SEQ ID NO 3
<211> LENGTH: 1104
<212> TYPE: DNA
<213> ORGANISM: Mycobacteria tuberculosis

<400> SEQUENCE: 3
```

| | |
|---|---|
| atgctgtggc acgcaatgcc accggagcta aataccgcac ggctgatggc cggcgcgggt | 60 |

-continued

```
ccggctccaa tgcttgcggc ggccgcggga tggcagacgc tttcggcggc tctggacgct    120
caggccgtcg agttgaccgc gcgcctgaac tctctgggag aagcctggac tggaggtggc    180
agcgacaagg cgcttgcggc tgcaacgccg atggtggtct ggctacaaac cgcgtcaaca    240
caggccaaga cccgtgcgat gcaggcgacg gcgcaagccg cggcatacac ccaggccatg    300
gccacgacgc cgtcgctgcc ggagatcgcc gccaaccaca tcacccaggc cgtccttacg    360
gccaccaact tcttcggtat caacacgatc ccgatcgcgt tgaccgagat ggattatttc    420
atccgtatgt ggaaccaggc agccctggca atggaggtct accaggccga daccgcggtt    480
aacacgcttt tcgagaagct cgagccgatg gcgtcgatcc ttgatcccgg cgcgagccag    540
agcacgacga acccgatctt cggaatgccc tcccctggca gctcaacacc ggttggccag    600
ttgccgccgg cggctaccca gaccctcggc caactgggtg agatgagcgg cccgatgcag    660
cagctgaccc agccgctgca gcaggtgacg tcgttgttca gccaggtggg cggcaccggc    720
ggcggcaacc cagccgacga ggaagccgcg cagatgggcc tgctcggcac cagtccgctg    780
tcgaaccatc cgctggctgg tggatcaggc cccagcgcgg gcgcgggcct gctgcgcgcg    840
gagtcgctac ctggcgcagg tgggtcgttg acccgcacgc cgctgatgtc tcagctgatc    900
gaaaagccgg ttgcccccctc ggtgatgccg cggctgctg ccggatcgtc ggcgacgggt    960
ggcgccgctc cggtgggtgc gggagcgatg gccagggtg cgcaatccgg cggctccacc    1020
aggccgggtc tggtcgcgcc ggcaccgctc gcgcaggagc gtgaagaaga cgacgaggac    1080
gactgggacg aagaggacga ctgg                                            1104

<210> SEQ ID NO 4
<211> LENGTH: 300
<212> TYPE: DNA
<213> ORGANISM: Mycobacteria tuberculosis

<400> SEQUENCE: 4
atggcagaga tgaagaccga tgccgctacc ctcgcgcagg aggcaggtaa tttcgagcgg     60
atctccggcg acctgaaaac ccagatcgac caggtggagt cgacggcagg ttcgttgcag    120
ggccagtggc gcggcgcggc ggggacggcc gcccaggccg cggtggtgcg cttccaagaa    180
gcagccaata agcagaagca ggaactcgac gagatctcga cgaatattcg tcaggccggc    240
gtccaatact cgagggccga cgaggagcag cagcaggcgc tgtcctcgca aatgggcttc    300

<210> SEQ ID NO 5
<211> LENGTH: 285
<212> TYPE: DNA
<213> ORGANISM: M. tuberculosis

<400> SEQUENCE: 5
atgacagagc agcagtggaa tttcgcgggt atcgaggccg cggcaagcgc aatccaggga     60
aatgtcacgt ccattcattc cctccttgac gaggggaagc agtccctgac caagctcgca    120
gcggcctggg gcgtagcgg ttcggaggcg taccagggtg tccagcaaaa atgggacgcc    180
acggctaccg agctgaacaa cgcgctgcag aacctggcgc ggacgatcag cgaagccggt    240
caggcaatgg cttcgaccga aggcaacgtc actgggatgt tcgca                    285

<210> SEQ ID NO 6
<211> LENGTH: 1998
<212> TYPE: DNA
<213> ORGANISM: Mycobacteria tuberculosis
```

-continued

<400> SEQUENCE: 6

```
atggcggccg actacgacaa gctcttccgg ccgcacgaag gtatggaagc tccggacgat      60
atggcagcgc agccgttctt cgaccccagt gcttcgtttc cgccggcgcc cgcatcggca     120
aacctaccga agcccaacgg ccagactccg ccccgacgt ccgacgacct gtcggagcgg     180
ttcgtgtcgg ccccgccgcc gccaccccca ccccacctc cgcctccgcc aactccgatg     240
ccgatcgccg caggagagcc gccctcgccg gaaccggccg catctaaacc acccacaccc     300
cccatgccca tcgccggacc cgaaccggcc cacccaaac cacccacacc cccatgccc     360
atcgccggac ccgaaccggc cccacccaaa ccacccacac ctccgatgcc catcgccgga     420
cctgcaccca ccccaaccga atcccagttg gcgcccccca gaccaccgac accacaaacg     480
ccaaccggag cgccgcagca accggaatca ccggcgcccc acgtaccctc gcacgggcca     540
catcaacccc ggcgcaccgc accagcaccg ccctgggcaa agatgccaat cggcgaaccc     600
ccgcccgctc cgtccagacc gtctgcgtcc ccggccgaac caccgaccg gcctgccccc     660
caacactccc gacgtgcgcg ccggggtcac cgctatcgca cagacaccga acgaaacgtc     720
gggaaggtag caactggtcc atccatccag gcgcggctgc gggcagagga agcatccggc     780
gcgcagctcg cccccggaac ggagccctcg ccagcgccgt tgggccaacc gagatcgtat     840
ctggctccgc ccacccgccc cgcgccgaca gaacctcccc ccagcccctc gccgcagcgc     900
aactccggtc ggcgtgccga cgacgcgtc caccccgatt tagccgccca acatgccgcg     960
gcgcaacctg attcaattac ggccgcaacc actggcggtc gtcgccgcaa gcgtgcagcg    1020
ccggatctcg acgcgacaca gaaatcctta aggccggcgg ccaaggggcc gaaggtgaag    1080
aaggtgaagc cccagaaacc gaaggccacg aagccgccca agtggtgtc gcagcgcggc    1140
tggcgacatt gggtgcatgc gttgacgcga atcaacctgg gcctgtcacc cgacgagaag    1200
tacgagctgg acctgcacgc tcgagtccgc cgcaatcccc gcgggtcgta tcagatcgcc    1260
gtcgtcggtc tcaaaggtgg ggctggcaaa accacgctga cagcagcgtt ggggtcgacg    1320
ttggctcagg tgcgggccga ccggatcctg gctctagacg cggatccagg cgccggaaac    1380
ctcgccgatc gggtagggcg acaatcgggc gcgaccatcg ctgatgtgct gcagaaaaaa    1440
gagctgtcgc actacaacga catccgcgca cacactagcg tcaatgcggt caatctggaa    1500
gtgctgccgg caccggaata cagctcggcg cagcgcgcgc tcagcgacgc cgactggcat    1560
tcatcgccg atcctgcgtc gaggttttac aacctcgtct tggctgattg tggggccggc    1620
ttcttcgacc cgctgacccg cggcgtgctg tccacggtgt ccggtgtcgt ggtcgtggca    1680
agtgtctcaa tcgacggcgc acaacaggcg tcggtcgcgt tggactggtt gcgcaacaac    1740
ggttaccaag atttggcgag ccgcgcatgc gtggtcatca atcacatcat gccgggagaa    1800
cccaatgtcg cagttaaaga cctggtgcgg catttcgaac agcaagttca acccggccgg    1860
gtcgtggtca tgccgtggga caggcacatt gcggccggaa ccgagatttc actcgacttg    1920
ctcgacccta tctacaagcg caaggtcctc gaattggccg cagcgctatc cgacgatttc    1980
gagagggctg gacgtcgt                                                  1998
```

<210> SEQ ID NO 7
<211> LENGTH: 1533
<212> TYPE: DNA
<213> ORGANISM: Mycobacteria tuberculosis

<400> SEQUENCE: 7

```

-continued

```
gccaccaccc gggtgacgat cctgaccggc agacggatga ccgatttggt actgccagcg    120
gcggtgccga tggaaactta tattgacgac accgtcgcgg tgctttccga ggtgttggaa    180
gacacgccgg ctgatgtact cggcggcttc gactttaccg cgcaaggcgt gtgggcgttc    240
gctcgtcccg gatcgccgcc gctgaagctc gaccagtcac tcgatgacgc cggggtggtc    300
gacgggtcac tgctgactct ggtgtcagtc agtcgcaccg agcgctaccg accgttggtc    360
gaggatgtca tcgacgcgat cgccgtgctt gacgagtcac ctgagttcga ccgcacggca    420
ttgaatcgct ttgtggggggc ggcgatcccg cttttgaccg cgcccgtcat cgggatggcg    480
atgcgggcgt ggtgggaaac tgggcgtagc ttgtggtggc cgttggcgat tggcatcctg    540
gggatcgctg tgctggtagg cagcttcgtc gcgaacaggt tctaccagag cggccacctg    600
gccgagtgcc tactggtcac gacgtatctg ctgatcgcaa ccgccgcagc gctggccgtg    660
ccgttgccgc gcggggtcaa ctcgttgggg gcgccacaag ttgccggcgc cgctacggcc    720
gtgctgtttt tgaccttgat gacgcggggc ggccctcgga agcgtcatga gttggcgtcg    780
tttgccgtga tcaccgctat cgcggtcatc gcggccgccg ctgccttcgg ctatggatac    840
caggactggg tccccgcggg ggggatcgca ttcgggctgt tcattgtgac gaatgcggcc    900
aagctgaccg tcgcggtcgc gcggatcgcg ctgccgccaa ttccggtacc cggcgaaacc    960
gtggacaacg aggagttgct cgatcccgtc gcgaccccgg aggctaccag cgaagaaacc   1020
ccgacctggc aggccatcat cgcgtcggtg cccgcgtccg cggtccggct caccgagcgc   1080
agcaaactgg ccaagcaact tctgatcgga tacgtcacgt cgggcaccct gattctggct   1140
gccggtgcca tcgcggtcgt ggtgcgcggg cacttctttg tacacagcct ggtggtcgcg   1200
ggtttgatca cgaccgtctg cggatttcgc tcgcggcttt acgccgagcg ctggtgtgcg   1260
tgggcgttgc tggcggcgac ggtcgcgatt ccgacgggtc tgacggccaa actcatcatc   1320
tggtacccgc actatgcctg gctgttgttg agcgtctacc tcacggtagc cctggttgcg   1380
ctcgtggtgg tcgggtcgat ggctcacgtc cggcgcgttt caccggtcgt aaaacgaact   1440
ctggaattga tcgacggcgc catgatcgct gccatcattc ccatgctgct gtggatcacc   1500
ggggtgtacg acacggtccg caatatccgg ttc                                1533
```

<210> SEQ ID NO 8
<211> LENGTH: 840
<212> TYPE: DNA
<213> ORGANISM: Mycobacteria tuberculosis

<400> SEQUENCE: 8

```
atggctgaac cgttggccgt cgatcccacc ggcttgagcg cagcggccgc gaaattggcc     60
ggcctcgttt ttccgcagcc tccggcgccg atcgcggtca gcggaacgga ttcggtggta    120
gcagcaatca acgagaccat gccaagcatc gaatcgctgg tcagtgacgg gctgcccggc    180
gtgaaagccg ccctgactcg aacagcatcc aacatgaacg cggcggcgga cgtctatgcg    240
aagaccgatc agtcactggg aaccagtttg agccagtatg cattcggctc gtcgggcgaa    300
ggcctggctg gcgtcgcctc ggtcggtggt cagccaagtc aggctaccca gctgctgagc    360
acaccggtgt cacaggtcac gacccagctc ggcgagacgg ccgctgagct ggcaccccgt    420
gttgttgcga cggtgccgca actcgttcag ctggctccgc acgccgttca gatgtcgcaa    480
aacgcatccc ccatcgctca gacgatcagt caaaccgccc aacaggccgc ccagagcgcg    540
cagggcggca gcggcccaat gcccgcacag cttgccagcg ctgaaaaacc ggccaccgag    600
```

-continued

| | |
|---|---|
| caagcggagc cggtccacga agtgacaaac gacgatcagg gcgaccaggg cgacgtgcag | 660 |
| ccggccgagg tcgttgccgc ggcacgtgac gaaggcgccg gcgcatcacc gggccagcag | 720 |
| cccggcgggg gcgttccgc gcaagccatg gataccggag ccgtgcccg cccagcggcg | 780 |
| agtccgctgg cggcccccgt cgatccgtcg actccggcac cctcaacaac acaacgttg | 840 |

<210> SEQ ID NO 9
<211> LENGTH: 2187
<212> TYPE: DNA
<213> ORGANISM: Mycobacteria tuberculosis

<400> SEQUENCE: 9

| | |
|---|---|
| atgagtatta ccaggccgac gggcagctat gccagacaga tgctggatcc gggcggctgg | 60 |
| gtggaagccg atgaagacac tttctatgac cgggcccagg aatatagcca ggttttgcaa | 120 |
| agggtcaccg atgtattgga cacctgccgc cagcagaaag gccacgtctt cgaaggcggc | 180 |
| ctatggtccg gcggcgccgc caatgctgcc aacggcgccc tgggtgcaaa catcaatcaa | 240 |
| ttgatgacgc tgcaggatta tctcgccacg tgattacct ggcacaggca tattgccggg | 300 |
| ttgattgagc aagctaaatc cgatatcggc aataatgtgt atggcgctca acgggagatc | 360 |
| gatatcctgg agaatgaccc tagcctggat gctgatgagc gccataccgc catcaattca | 420 |
| ttggtcacgg cgacgcatgg ggccaatgtc agtctggtcg ccgagaccgc tgagcgggtg | 480 |
| ctggaatcca agaattggaa acctccgaag aacgcactcg aggatttgct tcagcagaag | 540 |
| tcgccgccac cccagacgt gcctaccctg gtcgtgccat ccccgggcac accgggcaca | 600 |
| ccgggaaccc cgatcacccc gggaaccccg atcacccgg gaaccccaat cacacccatc | 660 |
| ccgggagcgc cggtaactcc gatcacacca acgcccggca ctcccgtcac gccggtgacc | 720 |
| ccgggcaagc cggtcacccc ggtgaccccg gtcaaaccgg gcacaccagg cgagccaacc | 780 |
| ccgatcacgc cggtcacccc cccggtcgcc cggccacac cggcaacccc ggccacgccc | 840 |
| gttaccccag ctcccgctcc acaccccgcag ccggctccgg caccggcgcc atcgcctggg | 900 |
| ccccagccgg ttacaccggc cactcccggt ccgtctggtc cagcaacacc gggcaccca | 960 |
| ggggcgagc cggcgccgca cgtcaaaccc gcggcgttgg cggagcaacc tggtgtgccg | 1020 |
| ggccagcatg cggcgggggg gacgcagtcg gggcctgccc atgcggacga atccgccgcg | 1080 |
| tcggtgacgc cggctgcggc gtccggtgtc ccgggcgcac gggcggcggc cgccgcgccg | 1140 |
| agcggtaccg ccgtgggagc gggcgcgcgt tcgagcgtgg gtacgccgc ggcctcgggc | 1200 |
| gcggggtcgc atgctgccac tgggcgggcg ccggtggcta cctcggacaa ggcggcggca | 1260 |
| ccgagcacgc gggcggcctc ggcgcggacg gcacctcctg cccgcccgcc gtcgaccgat | 1320 |
| cacatcgaca aacccgatcg cagcgagtct gcagatgacg gtacgccggt gtcgatgatc | 1380 |
| ccggtgtcgg cggctcgggc ggcacgcgac gccgccactg cagctgccag cgcccgccag | 1440 |
| cgtggccgcg gtgatgcgct gcggttggcg cgacgcatcg cggcggcgct caacgcgtcc | 1500 |
| gacaacaacg cgggcgacta cggttcttc tggatcaccg cggtgaccac cgacggttcc | 1560 |
| atcgtcgtgg ccaacagcta tgggctggcc tacatacccg acgggatgga attgccgaat | 1620 |
| aaggtgtact tggccagcgc ggatcacgca atcccggttg acgaaattgc acgctgtgcc | 1680 |
| acctacccgg ttttggccgt gcaagcctgg gcggcttttcc acgacatgac gctgcgggcg | 1740 |
| gtgatcggta ccgcggagca gttggccagt tcggatcccg tgtgggcaa gattgtgctg | 1800 |
| gagccagatg acattccgga gagcggcaaa atgacgggcc ggtcgcggct ggaggtcgtc | 1860 |
| gaccccttcgg cggcggctca gctggccgac actaccgatc agcgtttgct cgacttgttg | 1920 |

```
ccgccggcgc cggtggatgt caatccaccg ggcgatgagc ggcacatgct gtggttcgag    1980
ctgatgaagc ccatgaccag caccgctacc ggccgcgagg ccgctcatct gcgggcgttc    2040
cgggcctacg ctgcccactc acaggagatt gccctgcacc aagcgcacac tgcgactgac    2100
gcggccgtcc agcgtgtggc cgtcgcggac tggctgtact ggcaatacgt caccgggttg    2160
ctcgaccggg ccctggccgc cgcatgc                                        2187

<210> SEQ ID NO 10
<211> LENGTH: 426
<212> TYPE: DNA
<213> ORGANISM: Mycobacteria tuberculosis

<400> SEQUENCE: 10
atggccggac tgaacattta cgtgaggcgc tggcggacag cgcttcacgc aaccgtgtcg     60
gcattgatag ttgccatcct cggactcgcc atcaccccgg tcgctagtgc ggcgacggcc    120
agggcgacgt tgtcggtgac atcgacgtgg cagaccggtt tcatcgcccg cttcaccatc    180
acaaactcga gcacggcgcc gctaaccgat tggaagcttg aattcgactt gccggcagga    240
gaatccgtct tgcacacatg gaatagcacc gttgcacgat ctggcacgca ctacgttctc    300
agcccagcga attggaatcg catcattgcc ccggtggtt cagccacggg cggcctaaga     360
ggcgggctga ccggttctta ctcgccgccg tcgagttgtc tgctcaacgg gcaatatcct    420
tgcacc                                                               426

<210> SEQ ID NO 11
<211> LENGTH: 597
<212> TYPE: DNA
<213> ORGANISM: Mycobacteria tuberculosis

<400> SEQUENCE: 11
gtgaactcac cactggtcgt cggcttcctg gcctgcttca cgctgatcgc cgcgattggc     60
gcgcagaacg cattcgtgct gcggcaggga atccagcgtg agcacgtgct gccggtggtg    120
gcgctgtgca cggtgtccga catcgtgctg atcgccgccg gtatcgcggg gttcggcgca    180
ttgatcggcg cacatccgcg tgcgctcaat gtcgtcaagt tggcggcgc cgccttccta    240 atcggctacg ggctacttgc ggcccggcgg gcgtggcgac ctgtttgcgct gatcccatct    300 ggcgccacgc cggttcgctt agccgaggtc ctggtgacct gtgcggcatt cacgttcctc    360
aacccacacg tctacctcga caccgtcgtg ttgctaggcg cgctggccaa cgagcacagc    420
gaccagcgct ggctgttcgg cctcggcgcg gtcacagcca gtgcggtatg gttcgccacc    480
ctcgggttcg gagccggccg gttgcgcggg ctgttcacca accccggctc gtggagaatc    540
ctcgacggcc tgatcgcggt catgatggtt gcgctgggaa tctcgctgac cgtgacc       597

<210> SEQ ID NO 12
<211> LENGTH: 909
<212> TYPE: DNA
<213> ORGANISM: Mycobacteria tuberculosis

<400> SEQUENCE: 12
atggtggatc cgcagcttga cggtccacag ctggccgcat ggctgccgt ggtcgaactg     60 ggcagcttcg atgcggccgc ggagcgccta catgtcaccc cgtcggctgt cagtcagcgc    120
atcaagtcgt ggagcagca ggtcggccag gtgctggtgg tcagggaaaa gccatgtcgg    180
gcgacgaccg caggtatccc gctgttgcgg ttggccgcgc aaacagcgtt gctcgagtcc    240
```

-continued

```
gaggcgctcg ctgaaatggg tggcaacgcg tcgctgaaac gcacgcggat caccattgcg      300
gtaaacgccg attccatggc gacatggttt tcggccgtgt tcgacggtct cggcgacgtc      360
ctgctcgacg ttcggatcga ggaccaggac cattccgcgc ggctgctacg ggagggtgtg      420
gcgatgggcg cggtgaccac cgagcggaac ccggtgccgg gctgccgggt gcacccgctg      480
ggtgaaatgc gctacctacc agtggccagc aggccattcg tccagcgcca tctatccgac      540
gggttcactg ccgccgcggc ggctaaagct ccgtcactgg cgtggaatcg tgacgatggg      600
ctgcaggaca tgttggtgcg taaggccttt cgtcgcgcca tcaccagacc gacgcacttt      660
gtcccgacca cagagggctt caccgccgca gcgcgcgccg ggctgggatg gggcatgttc      720
cccgagaagc tggcagcatc tccgcttgcc gatggatcgt tcgtacgggt ctgcgacata      780
cacctcgacg tccctctcta ttggcaatgc tggaaactgg acagtccgat catcgcgcga      840
attaccgaca cggtgagggc ggcggcaagc ggtctgtacc ggggccagca acgccgccgc      900
cgaccgggt                                                             909
```

<210> SEQ ID NO 13
<211> LENGTH: 651
<212> TYPE: DNA
<213> ORGANISM: Mycobacteria tuberculosis

<400> SEQUENCE: 13

```
atgactccac gcagccttgt tcgcatcgtt ggtgtcgtgg ttgcgacgac cttggcgctg       60
gtgagcgcac ccgccggcgg tcgtgccgcg catgcggatc cgtgttcgga catcgcggtc      120
gttttcgctc gcggcacgca tcaggcttct ggtcttggcg acgtcggtga ggcgttcgtc      180
gactcgctta cctcgcaagt tggcgggcgg tcgattgggg tctacgcggt gaactaccca      240
gcaagcgacg actaccgcgc gagcgcgtca acggttccg atgatgcgag cgcccacatc      300
cagcgcaccg tcgccagctg cccgaacacc aggattgtgc ttggtggcta ttcgcagggt      360
gcgacggtca tcgatttgtc cacctcggcg atgccgcccg cggtggcaga tcatgtcgcc      420
gctgtcgccc ttttcggcga gccatccagt ggttttctcca gcatgttgtg gggcggcggg      480
tcgttgccga caatcggtcc gctgtatagc tctaagacca taaacttgtg tgctcccgac      540
gatccaatat gcaccggagg cggcaatatt atggcgcatg tttcgtatgt tcagtcgggg      600
atgacaagcc aggcggcgac attcgcggcg aacaggctcg atcacgccgg a               651
```

<210> SEQ ID NO 14
<211> LENGTH: 1674
<212> TYPE: DNA
<213> ORGANISM: Mycobacteria tuberculosis

<400> SEQUENCE: 14

```
gtgtcatttc tggtcgtggt tcccgagttc ttgacgtccg cggcagcgga tgtggagaac       60
ataggttcca cactgcgcgc ggcgaatgcc gcggctgccg cctcgaccac cgcgcttgcg      120
gccgctggcg ctgatgaggt atcggcgcg gtggcagcgc tgtttgccag gttcggtcag      180
gaatatcaag cggtcagcgc gcaggcgagc gctttccatc aacagttcgt gcagacgctg      240
aactcggcgt caggatcgta tgcggccgcg gaggccacca tcgcgtcaca gttgcagacc      300
gcgcagcacg atctgctggg cgcggtcaat gcaccaaccg aaacgttgtt ggggcgtccg      360
ctaatcggcg acggagcacc cggacggca acgagtccga atggcggggc gggtgggctg      420
ctgtacggca acggcggcaa cggttattcc gcgacggcgt cggggggtcgg cggcggggcc      480 ggcggttccg cggggttgat cggcaatggc ggcgccgggg gagccggcgg acccaacgcc      540
```

```
cccggggag ccggcggcaa cggtggctgg ctgctcggca acggcgggat cggcgggccc      600
gggggcgcgt cgagcatccc cggcatgagt ggtggagccg gcggaaccgg cggtgccgca      660
ggacttttgg gctggggagc gaacggcgga gccggcggcc tcggtgatgg agtcggtgtc      720
gatcgtggca cgggcggcgc cggaggccgc ggcggcctgt tgtatggcgg atacggcgtc      780
agtgggccag gcggcgacgg cagaaccgtc ccgctggaga taattcatgt cacagagccg      840
acggtacatg ccaacgtcaa cggcggaccg acgtcaacca ttctggtcga caccggatcc      900
gctggtcttg ttgtctcgcc tgaggatgtc gggggaatcc tgggagtgct tcacatgggc      960
ctcccaaccg gattgagcat cagcggttac agcggggggc tgtactacat cttcgccacg     1020
tataccacga cggtggactt cgggaatggc atcgtcaccg cgccgaccgc cgttaatgtc     1080
gtcctcttgt ccatcccaac gtccccttc gccatttcga cctacttcag cgccttgctg     1140
gccgatccga caacaactcc gttcgaagcc tatttcggtg ccgtcggcgt ggacggcgtt     1200
ctgggagttg ggcccaatgc ggtgggacca ggccccagca ttccgacgat ggcgttaccg     1260
ggtgacctca accagggagt gctcatcgac gcacccgcag gtgagctcgt gttcggtccc     1320
aacccgctac ctgcgcccaa cgtcgaggtc gtcggatcgc cgatcaccac cctgtacgta     1380
aagatcgatg gtgggactcc catacccgtc ccctcgatca tcgattccgg tggggtaacg     1440
ggaaccatcc cgtcatatgt catcggatcc ggaaccctgc cggcgaacac aaacattgag     1500
gtctacacca gccccggcgg tgatcggctc tacgcgttca acacaaacga ttaccgcccg     1560
accgtcattt catccggcct gatgaatacc gggttcttgc ccttcagatt ccagccggtg     1620
tacatcgact acagccccag cggtataggg acaacagtct ttgatcatcc ggcg          1674
```

<210> SEQ ID NO 15
<211> LENGTH: 1674
<212> TYPE: DNA
<213> ORGANISM: M. tuberculosis
<400> SEQUENCE: 15

```
gtgtcatttc tggtcgtggt tcccgagttc ttgacgtccg cggcagcgga tgtggagaac       60
ataggttcca cactgcgcgc ggcgaatgcc gcggctgccg cctcgaccac cgcgcttgcg      120
gccgctggcg ctgatgaggt atcggcggcg gtggcagcgc tgtttgccag gttcggtcag      180
gaatatcaag cggtcagcgc gcaggcgagc gctttccatc aacagttcgt gcagacgctg      240
aactcggcgt caggatcgta tgcggccgcg gaggccacca tcgcgtcaca gttgcagacc      300
gcgcagcacg atctgctggg cgcgtcaat gcaccaaccg aaacgttgtt ggggcgtccg      360
ctaatcggcg acggagcacc cggacggca acagtccga atggcgggc gggtgggctg      420 ctgtacggca acggcggcaa cggttattcc gcgacggcgt cggggtgtcgg cggcggggcc      480 ggcggttccg cggggttgat cggcaatggc ggcgccgggg gagccggcgg acccaacgcc      540
cccgggggag ccggcggcaa cggtggctgg ctgctcggca acggcgggat cggcgggccc      600
gggggcgcgt cgagcatccc cggcatgagt ggtggagccg gcggaaccgg cggtgccgca      660
ggacttttgg gctggggagc gaacggcgga gccggcggcc tcggtgatgg agtcggtgtc      720
gatcgtggca cgggcggcgc cggaggccgc ggcggcctgt tgtatggcgg atacggcgtc      780
agtgggccag gcggcgacgg cagaaccgtc ccgctggaga taattcatgt cacagagccg      840
acggtacatg ccaacgtcaa cggcggaccg acgtcaacca ttctggtcga caccggatcc      900
gctggtcttg ttgtctcgcc tgaggatgtc gggggaatcc tgggagtgct tcacatgggc      960
```

-continued

```
ctcccaaccg gattgagcat cagcggttac agcgggggc tgtactacat cttcgccacg      1020
tataccacga cggtggactt cgggaatggc atcgtcaccg cgccgaccgc cgttaatgtc      1080
gtcctcttgt ccatcccaac gtccccctcc gccatttcga cctacttcag cgccttgctg     1140
gccgatccga caacaactcc gttcgaagcc tatttcggtg ccgtcggcgt ggacggcgtt      1200 ctggagttg ggcccaatgc ggtgggacca ggccccagca ttccgacgat ggcgttaccg       1260
ggtgacctca accagggagt gctcatcgac gcacccgcag gtgagctcgt gttcggtccc      1320
aacccgctac ctgcgcccaa gtcgaggtc gtcggatcgc cgatcaccac cctgtacgta       1380
aagatcgatg gtgggactcc catacccgtc ccctcgatca tcgattccgg tggggtaacg      1440
ggaaccatcc cgtcatatgt catcggatcc ggaaccctgc cggcgaacac aaacattgag      1500
gtctacacca gccccggcgg tgatcggctc tacgcgttca acacaaacga ttaccgcccg      1560
accgtcattt catccggcct gatgaatacc gggttcttgc ccttcagatt ccagccggtg      1620
tacatcgact acagccccag cggtataggg acaacagtct ttgatcatcc ggcg            1674

<210> SEQ ID NO 16
<211> LENGTH: 417
<212> TYPE: DNA
<213> ORGANISM: Mycobacteria tuberculosis

<400> SEQUENCE: 16
atgatcgtgg acacaagcgc cgtggtggcc ctggttcaag gcgagcggcc gcacgccacc       60
ctggtcgcgc cgcccctggc cggcgcccat agccccgtca tgtctgcacc caccgtcgcc      120
gaatgcctga ttgtcttgac cgcccgtcac ggccccgttg cgcgcacgat cttcgaacga      180
cttcgcagcg aaatcggctt gagcgtgtca tctttcaccg ccgagcatgc cgctgccacg      240
caacgagcct tctgcgata cggcaagggg cgccaccgcg cggctctcaa cttcggagac       300
tgtatgacgt acgcgaccgc ccagctgggc caccaaccac tgctggccgt cggcaacgac      360
ttcccgcaaa ccgaccttga gttccgcggc gtcgtcggct actggccagg cgtcgcg         417

<210> SEQ ID NO 17
<211> LENGTH: 684
<212> TYPE: DNA
<213> ORGANISM: M. tuberculosis

<400> SEQUENCE: 17
gtgcgcatca agatcttcat gctggtcacg gctgtcgttt tgctctgttg ttcgggtgtg       60
gccacggccg cgcccaagac ctactgcgag gagttgaaag gcaccgatac cggccaggcg      120
tgccagattc aaatgtccga cccggcctac aacatcaaca tcagcctgcc cagttactac      180
cccgaccaga agtcgctgga aaattacatc gcccagacgc gcgacaagtt cctcagcgcg      240
gccacatcgt ccactccacg cgaagccccc tacgaattga atatcacctc ggccacatac      300
cagtccgcga taccgccgcg tggtacgcag gccgtggtgc tcaaggtcta ccagaacgcc      360
ggcggcacgc acccaacgac cacgtacaag gccttcgatt gggaccaggc ctatcgcaag      420
ccaatcacct atgacacgct gtggcaggct gacaccgatc cgctgccagt cgtcttcccc      480
attgtgcaag gtgaactgag caagcagacc ggacaacagg tatcgatagc gccgaatgcc      540
ggcttggacc cggtgaatta tcagaacttc gcagtcacga acgacggggt gattttcttc      600
ttcaacccgg gggagttgct gcccgaagca gccggcccaa cccaggtatt ggtcccacgt      660
tccgcgatcg actcgatgct ggcc                                            684
```

<210> SEQ ID NO 18
<211> LENGTH: 684
<212> TYPE: DNA
<213> ORGANISM: M. tuberculosis

<400> SEQUENCE: 18

```
gtgcgcatca agatcttcat gctggtcacg gctgtcgttt tgctctgttg ttcgggtgtg     60
gccacggccg cgcccaagac ctactgcgag gagttgaaag gcaccgatac cggccaggcg    120
tgccagattc aaatgtccga cccggcctac aacatcaaca tcagcctgcc cagttactac    180
cccgaccaga agtcgctgga aaattacatc gcccagacgc gcgacaagtt cctcagcgcg    240
gccacatcgt ccactccacg cgaagccccc tacgaattga atatcacctc ggccacatac    300
cagtccgcga taccgccgcg tggtacgcag gccgtggtgc tcaaggtcta ccagaacgcc    360
ggcggcacgc acccaacgac cacgtacaag gccttcgatt gggaccaggc ctatcgcaag    420
ccaatcacct atgacacgct gtggcaggct gacaccgatc cgctgccagt cgtcttcccc    480
attgtgcaag gtgaactgag caagcagacc ggacaacagg tatcgatagc gccgaatgcc    540
ggcttggacc cggtgaatta tcagaacttc gcagtcacga acgacggggt gattttcttc    600
ttcaacccgg gggagttgct gcccgaagca gccggcccaa cccaggtatt ggtcccacgt    660
tccgcgatcg actcgatgct ggcc                                           684
```

<210> SEQ ID NO 19
<211> LENGTH: 1443
<212> TYPE: DNA
<213> ORGANISM: Mycobacteria tuberculosis

<400> SEQUENCE: 19

```
gtggtcggcc cgcggacgag aggatatgcg atccacaagc tgggtttctg cagcgtcgtc     60
atgctcggga tcaactcgat aatcggcgcc ggtatcttcc taactccagg tgaggtgatc    120
gggctcgcag gacccttcgc gccgatggcc tatgttttag ctggcatttt cgcgggtgtc    180
gtggcgatcg tcttcgcgac ggcggcaagg tacgtcagaa caaacggtgc ctcctacgcc    240
tacacaacgg ccgcatttgg gcgccggatc ggcatctatg tcggtgtcac ccacgccatt    300
accgcgtcca tcgcttgggg ggtgttggct tcttttttcg tctcgacgct gttgcgagtg    360
gccttccccg acaaggcctg ggccgacgcc gagcaactgt tcagtgtgaa gacgctgacg    420
tttctcggct ttatcggcgt gctgttggcc atcaacctct tcggcaaccg ggcgatcaag    480
tgggccaacg gaacgtcaac ggtaggcaag gcattcgcgc tctcggcatt cattgtcggc    540
gggctgtgga tcatcaccac ccagcacgtg aacaactacg caacggcgtg gtcggcatac    600
agcgcgaccc cgtactcgtt gcttggcgtc gccgaaattg gcaagggcac gttctcgagt    660
atggcgctgg ccacgattgt cgcgttgtac gcattcaccg gtttcgaatc gatcgcgaac    720
gccgccgaag aaatggacgc gccggaccgg aacctgccga gagctatacc gatcgcgatc    780
ttctcggttg gcgcgatcta cttgctcacc ctaacggtag cgatgctgct cggatcgaac    840
aagatcgccg cgtcggacga caccgtgaaa ctggccgcgg ccatcggaaa cgctaccttc    900
cgaacgatca tcgtcgtcgg agccctgata tcgatgttcg gcatcaatgt cgcggcctcg    960
ttcggtgcac cgcggctttg gaccgcgtta gcggacagcg ggttctgcc gacacgcttg    1020
tcacgcaaga accaatacga cgtgccgatg gtctccttcg caattacggc gtcgttggcg   1080
ctcgcattcc cgttggcgct gcggttcgac aacctgcacc tgaccggcct ggcggtgatc   1140
gcccgattcg tccagttcat catcgtgccg atcgctctca tcgcattggc gaggtctcag   1200
```

```
gcagtagaac atgctgctgt gcggcgaaat gcgttcaccg acaaggtgtt accgcttgtt    1260
gcgatcgtgg tctcggttgg gctggcagtg tcctacgact accgctgcat ctttctagtg    1320
cggggtggtc cgaactactt ctcgattgct ttgatcgtga tcacgttcgt cgtggtaccg    1380
gcgatggctt atctgcacta ctaccgaatc attcgccggg ttggcgatcg gccgagcact    1440
cgc                                                                  1443
```

<210> SEQ ID NO 20
<211> LENGTH: 846
<212> TYPE: DNA
<213> ORGANISM: Mycobacteria tuberculosis

<400> SEQUENCE: 20

```
atgggtgagg cgaacatccg cgagcaggcg atcgccacga tgccacgggg tggccccgac      60
gcgtcttggc tggatcgtcg attccagacc gacgcactgg agtacctcga ccgcgacgat     120
gtgcccgatg aggtcaaaca gaagatcatc ggggtgctcg accgggtggg caccctgacc     180
aacctgcacg agaagtacgc ccggatagcc ctgaaacttg tttctgacat tcccaacccg     240
cgaatcctgg aacttggtgc gggccatggc aagctctcag cgaaaatcct cgagctacac     300
ccgacagcga cggtgacgat cagcgatcta gatcccacct cggtggccaa catcgccgcg     360
ggagagctgg gaacacatcc gcgagcacgc acccaagtga tcgacgccac cgcaatcgac     420
ggccacgacc acagctatga cctggcggtc ttcgcgctgg catttcacca cctgccgcct     480 acgtcgcct gcaaagcgat cgccgaggcc acccgggtgg ggaagcgctt tctgatcatc      540
gacctcaaac ggcagaaacc gctgtcgttc acgctctctt cggtgctgct actgccgctc     600
cacctactgc tgctgccatg gtcgtcgatg cgctcgagca tgcacgacgg ctttatcagc     660
gcactacgtg cctacagtcc ctcggcgttg cagacgcttg cccgcgccgc cgatccggga     720
atgcaggttg aaatcttgcc cgcaccgacc aggctattcc cgccatcgct cgccgttgtg     780
ttctcccgtt cgagctcagc gccaacggaa tctagcgagt gctcggccga tcgccaaccc     840
ggcgaa                                                               846
```

<210> SEQ ID NO 21
<211> LENGTH: 1407
<212> TYPE: DNA
<213> ORGANISM: Mycobacteria tuberculosis

<400> SEQUENCE: 21

```
gtgagataca ctacacctgt gcgtgctgct gtctacctcc gaatctcaga agaccgctcc     60
ggcgaacagc tcggcgtggc ccgccaacgc gaggactgcc taaagctgtg cgggcagcga    120
aaatgggtgc ccgtcgagta cctcgacaac gacgtcagcg catcaaccgg caagcgccgc    180
cccgcctacg agcagatgtt ggccgacatc accgccggca agatcgccgc cgtggtggcc    240
tgggacctgg accggctcca tcgccgtccc atcgagctgg aagccttcat gtcattagcc    300
gacgagaagc ggctggccct ggccaccgtc gccggcgacg ttgacctggc gacaccccag    360
ggccggctag tcgcccgcct gaaggggtcg gtggccgctc acgaaaccga gcacaagaag    420
gcacgacagc gccgcgccgc ccgccagaaa gctgaacgcg gccaccccaa ctggtcgaaa    480
gccttcggct acctgcccgg ccccaacggt cccgaacccg acccccggac agcgccgctg    540
gtcaaacagg cctacgccga catcctcgcc ggggcgtccc tgggcgacgt gtgccgccag    600
tggaacgacg ccggggcgtt caccatcacc ggccgcccgt ggacgactac aacgctgtcg    660
aaattcttgc gcaaaccccg caacgccgga ctacgcgcat ataagggtgc ccgctacggc    720
```

```
ccggtggacc gcgacgcgat tgtcggcaag gcccagtggt cgccgctggt ggacgaggcg    780
acgttctggg ccgcccaggc cgtgctggac gcccccggcc gcgccccggg ccgcaaaagc    840
gtgcgccgcc acctgctgac cgggctggca ggctgcggca atgcggcaa ccacctggcc    900 ggcagctacc gcaccgacgg ccaggtcgtc tacgtgtgca aggcgtgcca cggggtggcc    960
atcctggccg acaacatcga accgatcctg tatcacatcg tggccgagcg gctggccatg   1020
cccgacgccg ttgacttgtt gcgccgggag attcacgacg ccgccgaagc cgaaaccatc   1080
cgcctggaac tggaaaccct ctacggggag ctggacaggc tcgccgtcga acgcgccgaa   1140
gggctactga ccgcgcgcca ggtgaagatc agcaccgaca tcgtcaacgc caagataacg   1200
aaacttcagg cccgccaaca ggatcaggaa cggctccgag tgttcgacgg gataccgttg   1260
ggaacaccgc aagtcgccgg gatgatagcc gagctgtcgc cggaccggtt ccgcgccgtc   1320
ctcgacgtcc tcgctgaagt cgttgtccag ccggtcggca gagcggcag gatattcaat    1380 cccgaacggg tgcaggtgaa ttggcga                                      1407

<210> SEQ ID NO 22
<211> LENGTH: 513
<212> TYPE: DNA
<213> ORGANISM: M. tuberculosis

<400> SEQUENCE: 22
atgagccggc accacaacat cgtgatcgtc tgtgaccacg gccgcaaagg cgatggccgc     60
atcgaacacg agcgctgcga tcttgtcgcg ccgatcattt gggtcgacga gacccagggc    120
tggttaccgc aggcgccagc ggtggcaaca ttactgacg acgacaacca gccgcgagcc    180
gttattggct tgccgcccaa cgagtctcgc ctacgacctg aaatgcgccg cgacgggtgg    240
gtgcggctgc actgggaatt cgcctgcctg aggtacggcg ccgccggcgt gcgcacgtgc    300
gagcagcggc ccgtgcgggt tcgcaacggc gacctgcaaa cactgtgcga gaacgttccg    360
cggctactga ccggactggc cggcaaccc gactacgcac cgggttttgc ggtgcagtcg    420
gacgcggtgg tcgtcgccat gtggctgtgg cgcacgctct gcgaaagcga cacgccgaac    480
aaactacgcg ccaccccaac gcgtggtagc tgc                                513

<210> SEQ ID NO 23
<211> LENGTH: 219
<212> TYPE: DNA
<213> ORGANISM: M. tuberculosis

<400> SEQUENCE: 23
gtgtcgacca tctaccatca tcgcggccgc gtagccgcac tgtctcgttc ccgcgcatcc     60
gacgatcccg agttcatcgc cgcgaaaacc gatctcgttg ccgcgaacat cgcggactac    120
ctcatccgca ccctcgccgc agcgccgccc ctgactgacg agcagcgcac ccggctggcc    180
gagctgctgc gccccgtgcg gcggtcaggc ggtgcccga                           219

<210> SEQ ID NO 24
<211> LENGTH: 396
<212> TYPE: DNA
<213> ORGANISM: Mycobacteria tuberculosis

<400> SEQUENCE: 24
atgaccgccg cgccggcgg gtcgccgccg acgcgacgat gcccggccac ggaggaccgg     60
gcacccgcga cagtcgccac accgtctagc gccgatccta ccgcgtcacg cgccgtgtcg    120
```

-continued

| | | |
|---|---|---|
| tggtggtcgg tgcacgagca tgtcgcgccg gtcctggatg ctgccgggtc gtggccgatg | 180 |
| gccggcacac cggcctggcg tcagctcgac gacgccgatc ctcgcaaatg ggccgcgatc | 240 |
| tgcgacgcag cccggcactg ggctctgagg gtagagacgt gccaggaggc gatggcgcag | 300 |
| gcgtcacgtg acgtatctgc ggccgccgac tggcccggca tcgcccgcga gatcgtccga | 360 |
| cggcgcggcg tgtacatccc gcgggcgggg gtggcg | 396 |

<210> SEQ ID NO 25
<211> LENGTH: 1413
<212> TYPE: DNA
<213> ORGANISM: Mycobacteria tuberculosis

<400> SEQUENCE: 25

| | |
|---|---|
| atggccgaca tccctacgg caccgactat cccgacgccc cctggatcga ccgggacggg | 60 |
| cacgtgctca tcgacgacgg tggcaaaccg acgcaagttc atcgcggcca agcccgaatc | 120 |
| gcctaccggc tagccgaacg ttaccaggac aagctgctgc acgtggccgg gatcggctgg | 180 |
| cactcctggg acggcagacg ctgggcagcc gacgaccgcg gcgaagccaa acgtgcagtg | 240 |
| ctggcagagc tgcgccaagc gctctcagac agcctcaacg acaaggaatt acgcgccgac | 300 |
| gtccgaaaat gcgaatcggc gtccggcgtg gccggcgtgc tcgacctggc cgccgcactg | 360 |
| gtaccattcg ccgcgacggt agccgacctc gacagcgacc cgcacttgct caacgtcgcg | 420 |
| aatgggacgc tggacctgca cacgctcaaa ttgcggcccc acgcgccgc tgaccgcatc | 480 |
| acaaagatat gccgcggtgc ctaccagtcc gacaccgaat cgcctctctg caagcgttc | 540 |
| ttgacccgcg ttctgcccga tgaaggtgtg cgcgggttcg tgcaacgcct ggccggcgtc | 600 |
| ggcctactag gcaccgtccg cgaacatgtc ctggcgattc ttatcggtgt aggtgccaac | 660 |
| ggaaaatctg tgttcgacaa ggcgattcgc tatgcccttg gcgattatgc ctgcaccgct | 720 |
| gagcctgacc ttttcatgca ccgggaaaac gctcacccaa caggcgaaat ggacctccgc | 780 |
| ggcgtgcgat gggtagcggt atccgagagc gaaaagatc gccggctggc cgaatcaacg | 840 |
| ataaaacggc tgactggcgg cgacaccatc cgcgcccgaa agatgcggca agacttcgtg | 900 |
| gaattcacgc cgtcacatac cccactgctc atcaccaacc acctaccgag agtgcccggc | 960 |
| gatgatacgc ccatctggcg gcgaattcga gtggtgccgt ttgaagtagt gattcctgcc | 1020 |
| gacgagcagg accgggaact ggacgcacgg ttgcagttgg aggccgacag catcctgtcc | 1080 |
| tgggcggtgg ccggatggag cgactatcag cgaatcggac tatcccagcc ggacgcggtg | 1140 |
| ctcgcggcaa cgtcgaatta ccgcgaggac tccgacacga taagagggtt catcgacgac | 1200 |
| gaatgcgtca ccagctcgcc ggtgctgaaa gccactacta cgcatctgtt cgaggcgtgg | 1260 |
| caaaggtggc gggtgcaaga aggcgtaccc gaaatctcgc gcaaagcgtt cggccagtcg | 1320 |
| ctcgacaccc acgataccc ggtcactgac aaggcccgtg atggtcgttg gcgggccgga | 1380 |
| atagcggtga gaggggccga tgatttcgat gat | 1413 |

<210> SEQ ID NO 26
<211> LENGTH: 393
<212> TYPE: DNA
<213> ORGANISM: Mycobacteria tuberculosis

<400> SEQUENCE: 26

| | |
|---|---|
| atgaccgctg tcgcgatcac cccggcatcc ggcggtcggc acagcgtccg attcgcctac | 60 |
| gactctcgca tcgtgtcgtt gatcaagtcc acgatccccg cctatgcccg ctcctggtcc | 120 |
| gcgcacaccc gctgctggtt catcgacgct gactggaccc cactgctggc cgccgagctg | 180 |

```
cgctaccacg gccacaccgt caccggaccc gccgacccgg cgcaacagca gtgcaccgac      240
tgggccaaag cgttgttccg ggcggtcgga ccccagcgga cacccgccgt gtacagggct      300
ttatccaaag tgctgcaccc cgacgcccca accggatgcc cgatactgca acagcagctc      360
aatgccgcca gaaccgcact taccaaccct gct                                   393
```

<210> SEQ ID NO 27
<211> LENGTH: 270
<212> TYPE: DNA
<213> ORGANISM: Mycobacteria tuberculosis

<400> SEQUENCE: 27

```
atggctgaaa cccccgacca cgccgaactg cggcgacgaa tcgccgacat ggctttcaac       60
gccgatgtcg gtatggcgac ctgcaaacgc tgtggtgacg ccgtgccgta catcatcctg      120
ccgaacctgc agaccggcga acccgtcatg ggtgtcgccg acaacaaatg gaagcgcgcg      180
aactgtcccg tcgacgtcgg taagccgtgc ccgttcctaa tcgccgaggg tgtcgccgac      240
agcaccgacg acaccataga ggtcgaccag                                       270
```

<210> SEQ ID NO 28
<211> LENGTH: 312
<212> TYPE: DNA
<213> ORGANISM: Mycobacteria tuberculosis

<400> SEQUENCE: 28

```
gtgaccccga tcaaccggcc cctgaccaac gacgaacgac aactgatgca cgagctggca       60
gtccaggttg tctgctcgca gacgggttgc tcacccgatg cggcggtcga agcactcgaa      120
tccttcgcga aagacggaac acttatcctc cgcggcgaca ccgagaacgc ctacctcgaa      180
gccggaggca atgttcttgt ccatgccgat cgtgactggc ttgccttcca cgcgtcgtat      240
cccggcaacg acccgctgcg agacgcccga cctatcgagc aggacgacga ccaggggcg      300 gggtcgccat cg                                                          312
```

<210> SEQ ID NO 29
<211> LENGTH: 468
<212> TYPE: DNA
<213> ORGANISM: Mycobacteria tuberculosis

<400> SEQUENCE: 29

```
atgccaagac caccgaaacc ggcccggctc aaactggttg agggccgctc ccccggccgc       60
gattccggcg gccggaaagt ccccgagtcg ccgaagtttta tccgtcaggc accggatgcc      120
ccggactggc tcgacgccga ggcgctgccc gaatggcggc gcgtcgcacc gactttggag      180
cggcttgacc tgctcaaacc tgaggatcgg gcgctcctgt ccgcgtactg cgagacctgg      240
tccgtctacg tcgcggcgt tcagcgggtc cgcgccgaag gcctcacaat tacctcaccg      300
aaatccggtg tcgtgcaccg gaacccggcg gtgacggttg cggagacggc gcgcatgcat      360
ctgctgcgct tggcctccga gtttggcctg acccccgccg ccgagcagcg actggcggtg      420
gcgccgggcg acgacggcga cgggctcaac ccgtttgccc cggaccgg                   468
```

<210> SEQ ID NO 30
<211> LENGTH: 510
<212> TYPE: DNA
<213> ORGANISM: Mycobacteria tuberculosis

<400> SEQUENCE: 30

-continued

```
atggccgagc tgcggtctgg cgaaggccga accgtgcacg gcaccatcgt gccctacaac        60
gaggcgacca ccgtccgcga cttcgacggc gagttccagg aaatgttcgc tcctggcgct       120
tttcggcgct ccatcgccga gcgcggccac aaattgaagc tgctggtctc tcacgacgct       180
cgaacccgct acccggtggg ccgggccgtt gagttgcggg aggagcctca cggcttgttc       240
ggggcgttcg agattgcgga cacccccgac ggcgacgagg cttttggcgaa cgtaaaagct       300 ggtgtcgtcg actcgttttc ggtgggtttc cgaccgatcc gggaccgtcg cgaaggggat       360
gtgctggtgc gcgtcgaagc ggcgctgtta gaggtttccc taaccggcgt tccggcctat       420 tcggggcac aaatcgccgg ggtgcgcgcg gaatcgctta cagtcgtttc ccgttcgaca        480
gccgaagcct ggctgtccct actcgattgg                                         510

<210> SEQ ID NO 31
<211> LENGTH: 1419
<212> TYPE: DNA
<213> ORGANISM: Mycobacteria tuberculosis

<400> SEQUENCE: 31
atgaccgaat tcgacgacat caaaaacctc tctttacctg aaacccgtga cgcggcgaag        60
cagctcctcg acagtgtcgc cggcgacctg accggtgagg cggcgcagcg ttttcaggcg       120
ctgacgcgcc acgccgagga actgcgggcg gagcagcgcc gccgcggccg cgaagccgag       180
gaggcgctgc gccgctaccg ggccggtgag ctgagggtgg tgcccggcgc tcccaccggc       240
ggcgacgacg gcgacgcgcc gccgggcaac tcgttgcggg acaccgcgtt cgcacactg       300 gattcttgtg tgcgagacgg cctgatgtcg tcgcgggcgg cggagaccgc ggaaaccttg       360
tgccgcaccg ggccgccgca gtccacctcg tgggcgcagc gctggctggc ggccaccggc       420
agccgcgact atttgggcgc gttcgtcaag cgggtttcca atcctgttgc ggggcacacg       480
gtttggaccg accgggaagc ggccgcgtgg cgtgaggctg ccgcggtggc cgccgagcag       540
cgagcgatgg gcctggtgga cacccaaggc gggtttctga tcccggcggc gctggacccg       600
gcgatcctgc tgtcgggtga tgggtcgacg aacccgattc ggcaggtggc gagggtggtg       660
caaacgacct ccgagatttg gcggggcgtg acttccgaag gcgccgaagc tcgttggtac       720
tccgaagccc aggaggtgtc cgacgattcg ccagcgttgg cccagccggc ggtgccgaac       780
taccgtggaa gctgctggat tccgttctcc atcgagctgg agggtgacgc ggcgagcttc       840
gttggcgaga tcggcaagat tctcgcggac agcgttgagc aactgcaggc cgcggcgttc       900
gtcaacggct ccggcaacgg cgagcccacc gggttcgtca gcgcgctaac cggcacctcc       960
gatcaggtgg tcgtcggcgc ggggtcagaa gcgattgtgg cggcggatgt ttacgcgttg      1020
cagtcggcgc tgccgccaag gttccaggcc agcgccgcgt tcgcggcgaa cttgtccacc      1080
atcaacacgt tgcggcaggc ggaaacttcg aatggcgcgc tgaaattccc atcgctgcac      1140
gacagtccgc cgatgctagc cgggaagtct gtcctggaag tctcccacat ggacaccgtt      1200
gattcggcgg tgacagcgac gaatcatcca ctggtgcttg gcgactggaa gcaattcctc      1260
atcggcgaca gagttgggtc catggtggag ttggtgcctc acctgttcgg gccgaatcgc      1320
cggccgaccg ggcagcgcgg attcttcgcc tggttcaggg tcggatcaga tgtgctggtg      1380
cgcaacgcgt ttcgagttct gaaggtggag actaccgcg                             1419

<210> SEQ ID NO 32
<211> LENGTH: 351
<212> TYPE: DNA
<213> ORGANISM: Mycobacteria tuberculosis
```

-continued

<400> SEQUENCE: 32
atggcgccgc tggccgccgg atcgccgagc tggaacggcc gaaagccaag cagcggcaac 60
aggaaggcgg cgaccatggc cgccaggctc gatattctgg cttggggccc atgggcccca 120
agccagaatc ggagcgtcgt tcgacgaaaa cagacactgc tatcggcgca gccctcggca 180
tctccgccgg cacctaccgg cggctcaaac gaatcgacaa cgcaacccgc agcgagttgg 240
cgcgtgggcg gcccggcacc cctaagcaga ggccgcccac gcctggccct atcctaccta 300
cgcggtagtc tccaccttca gaactcgaaa cgcgttgcgc accagcacat c 351

<210> SEQ ID NO 33
<211> LENGTH: 309
<212> TYPE: DNA
<213> ORGANISM: Mycobacteria tuburculosis

<400> SEQUENCE: 33
atgggctaca aaccagaatc agagcgtcat tcgacgaaaa cagacactgc tatcggcgca 60
gccctcggca tctccgccgg cacctaccgg cggctcaaac gaatcgacaa cgcaacccac 120
agcgacgaca aagaaatccg ccggttcgcg gagaaacaaa tggcgccgct ggtcgccgga 180
tcgccgagct ggaacgcccg aaagccaagg agcgccaacg cgagggtggt cgcctcggtg 240
catcgatcac caatgccggc tttggtccca tggaaccaaa gccgtctcag cgccacactg 300
acaaggagg 309

<210> SEQ ID NO 34
<211> LENGTH: 408
<212> TYPE: DNA
<213> ORGANISM: Mycobacteria tuburculosis

<400> SEQUENCE: 34
atgaccacca caccagcacg tttcaaccac ttggtgacgg taaccgacct ggaaacgggt 60
gaccgcgccg tctgcgaccg cgaccaggtg gccgagacga tccgggcgtg gttcccggac 120
gcgcccttgg aggtgaggga agcgctcgtt cggctgcagg ccgcgttgaa tcggcacgag 180
cacaccggcg agctcgaagc gttcctgcgg atcagcgtcg agcacgccga cgccgccggc 240
ggcgacgagt gcggcccggc gatcctggcc ggccgctccg ggccggaaca agccgccatc 300
aaccggcaac tcggactcgc cggcgacgac gagcccgacg gcgacgacac cccgccgtgg 360
agccggatga tcgggcttgg cggcggaagc ccagcggaag acgagcgc 408

<210> SEQ ID NO 35
<211> LENGTH: 1407
<212> TYPE: DNA
<213> ORGANISM: Mycobacteria tuburculosis

<400> SEQUENCE: 35
gtgaaacggc tcagcggctg ggacgcggta ctgctttaca gcgagacccc gaatgtgcac 60
atgcacacac tcaaggtcgc cgtgatcgaa ttggattcgg acagacagga attcggtgtc 120
gacgcgtttc gcgaggtgat cgctggccgg ctgcataagc ttgagccatt gggctatcag 180
ctggttgatg tcccgttgaa gttccatcac ccgatgtggc gggagcactg ccaggtcgat 240
ctcaactacc acatccggcc gtggcggttg cgcgccccgg ggggtcggcg cgaactcgac 300
gaggcggtcg gagaaatcgc cagcaccccg ctgaaccgcg accacccgct gtgggagatg 360
tacttcgttg aggggcttgc caaccaccgg atcgcggtgg ttgccaaaat tcaccatgcg 420

-continued

```
ttggctgacg gtgttgcctc ggcaaacatg atggcacggg ggatggatct gctgccggga        480
ccggaggtcg gccgctatgt gcctgacccc gctcctacca agcggcagtt gctgtccgcg        540
gcgttcatcg accacttgcg ccacctcggc cggattcctg caaccatccg gtacaccacg        600
cagggtctag gccgggtgcg acgtagctcg cgcaagctct caccctgcact gaccatgcca        660 tttaccccgc caccgacgtt catgaatcac cggctcaccc cggagcgcag gttcgccacc        720
gccaccctgg cgctgattga cgtgaaggcg acggccaagt tgctggggggc gacgatcaac       780 gacatggtgc tggccatgtc gaccggcgct ctgcgtaccc tgctattgcg ctatgacggc        840
aaggccgaac cgctgctggc gtcggtcccg gtgagttacg acttctcacc ggagcggatc        900
tccggtaacc gcttcaccgg aatgctggtg gcgctgcctg ccgactccga cgacccgttg        960
cagcgggtgc gcgtctgtca cgaaaacgcg gtctccgcca aggagagcca ccagcttttg       1020
ggaccggagt tgatcagccg ctgggcggct actggccac ctgccggtgc ggaagccttg        1080
ttccggtggt tgtctgagcg cgacgggcag aacaaggtac tcaacttgaa tatctcgaat       1140
gttcccggtc cgcgcgaacg cggccgcgtg ggggccgcgc tggtcaccga gatctattcg       1200
gtgggcccgt tgaccgccgg tagcggattg aatatcacgg tgtggagtta tgtcgatcag       1260
ctcaatatct cggtgttaac cgatggttcc accgtgcagg accgcatgaa agtaaccgcg       1320
ggaatgatcg cggacttcat cgaaatacgc gcgccgctg tctttccgt ggagttgaca         1380 gtcgtcgagt ccgcgatggc gcaggca                                           1407
```

<210> SEQ ID NO 36
<211> LENGTH: 786
<212> TYPE: DNA
<213> ORGANISM: Mycobacteria tuburculosis

<400> SEQUENCE: 36

```
atgagcagcg aaagcgacgc agccaacacc gaacctgagg ttctggtaga acagcgggat         60
cggattttga tcatcacgat caaccgcccg aaagccaaga acgcggtcaa cgccgcagtc        120
agccggggct tggccgatgc gatggatcag cttgacggcg atgccggcct gtcggtggca        180
atcctgaccg gtgggggcgg ttcgttctgc gcgggcatgg acctcaaggc gttcgcccgg        240
ggcgagaatg tcgtcgtcga aggtcgcggc cttggcttta ccgaacgtcc gccgaccaag        300
ccgctcattg ctgcggtgga aggctacgcg ttggcgggtg gcaccgagct ggcgcttgct        360
gccgacctga tcgtggcggc cagggattcg gcgttcggga ttcctgaagt caagcgggggt       420 ctggttgccg gcggcggggg attgctgcgg ttgccggagc gcatcccgta tgcgatagcc       480
atggagttgg cgctgaccgg tgacaaccta ccggccgaac gcgcgcacga gctgggggctc      540 gtcaacgttt tggccgagcc ggggaccgcc ctcgatgctg cgatcgcgtt ggcggagaag       600
atcaccgcca atgggccgct ggcggtggtg gccaccaagc ggattatcac cgagtcgcgt       660
gggtggagtc ccgacactat gttcgctgag cagatgaaga tcctggtgcc ggtgttcacc       720
tccaacgacg cgaaggaagg tgcgatcgcg ttcgccgaga ggcgccggcc ccgttggacg       780
ggcacc                                                                 786
```

<210> SEQ ID NO 37
<211> LENGTH: 1461
<212> TYPE: DNA
<213> ORGANISM: M. tuberculosis

<400> SEQUENCE: 37

```
atgtctgaca gtgccacgga atacgacaag ctttttcatcg gcggc

-continued

```
tcgacctccg atgttatcga ggtacgctgc ccagccactg gggaatatgt cggcaaggtg      120
ccgatggcgg ccgccgccga cgtcgacgcc gcggtcgccg cagcacgtgc ggcgttcgac      180
aacggcccct ggccctcgac cccgccgcac gagcgtgcgc cggtgatcgc tgcggcggtc      240
aagatgctgg ctgagcgcaa ggacctgttc accaagctgc tcgcagccga accggccag      300 ccgccgacca tcatcgagac gatgcactgg atgggttcga tggggcgat gaactacttt      360 gccggtgcag cggacaaggt cacctggacc gaaacccgca ccggctccta tggacagagc      420
attgtcagcc gtgagccggt cggtgtggtg ggcgcgatcg tggcctggaa cgtcccgctg      480
tttctggccg tcaacaagat gcgccggcg ctgctggccg gctgcaccat cgtgctcaag      540
cccgccgccg aaacaccgct gaccgcaaac gctttggcgg aggtgttcgc cgaggtgggc      600
ctgcccgagg gggtgttgtc ggtagtgccg ggagggattg agaccggtca ggcgctgacg      660
tctaacccgg acatcgacat gtttaccttc accggcagct cggccgtcgg ccgagaggtc      720
ggcaggcgtg ccgctgagat gctcaagccg tgcaccttag aactcggcgg caagtcggcg      780
gccatcattc tcgaggacgt cgacctggcc gcagctattc cgatgatggt gttctccggc      840
gtcatgaacg ccggacaggg ctgcgtcaac cagacccgca ttctggctcc gcgctcccgg      900
tacgacgaaa tcgtggctgc ggtaactaat ttcgtaacgg ctctcccggt gggcccgccg      960
tcggacccgg cagctcagat cgggccgctg atctcggaga agcagcggac tcgcgttgaa     1020
ggctacatcg ccaagggcat cgaggaggc gctcggttgg tgtgcggcgg cggccgtccc     1080
gagggcttgg acaacggctt ctttatccaa cccaccgtat tcgccgatgt cgacaacaag     1140
atgaccatcg cacaggagga gatcttcggg ccggtgctgg ccatcattcc ttatgacacc     1200
gaggaggacg cgatcgcgat cgccaacgat tcagtgtatg ggctggcggg cagcgtgtgg     1260
accaccgacg tgcccaaagg catcaagatc tcgcagcaga tccgcaccgg gacatacgga     1320
atcaactggt acgccttcga tcccggctca cccttcggcg gctacaagaa ctccggaatc     1380
ggccgcgaga acgggcccga gggtgtcgaa cacttcaccc agcaaaagag tgtcctgctg     1440
ccgatgggct acaccgtcgc g                                               1461
```

<210> SEQ ID NO 38
<211> LENGTH: 831
<212> TYPE: DNA
<213> ORGANISM: M. tuberculosis

<400> SEQUENCE: 38

```
atggcacgct gcgatgtcct ggtctccgcc gactgggctg agagcaatct gcacgcgccg       60
aaggtcgttt tcgtcgaagt ggacgaggac accagtgcat atgaccgtga ccatattgcc      120
ggcgcgatca agttggactg gcgcaccgac ctgcaggatc cggtcaaacg tgacttcgtc      180
gacgcccagc aattctccaa gctgctgtcc gagcgtggca tcgccaacga ggacacggtg      240
atcctgtacg gcggcaacaa caattggttc gccgcctacg cgtactggta tttcaagctc      300
tacggccatg agaaggtcaa gttgctcgac ggcgccgca agaagtggga gctcgacgga      360
cgcccgctgt ccagcgaccc ggtcagccgg ccggtgacct cctacaccgc ctccccgccg      420
gataacacga ttcgggcatt ccgcgacgag gtcctggcgg ccatcaacgt caagaacctc      480
atcgacgtgc gctctcccga cgagttctcc ggcaagatcc tggccccgc gcacctgccg      540 caggaacaaa gccagcggcc cggacacatt cctggtgcca tcaacgtgcc gtggagcagg      600
gccgccaacg aggacggcac cttcaagtcc gatgaggagt tggccaagct ttacgccgac      660
```

-continued

```
gccggcctag acaacagcaa ggaaacgatt gcctactgcc gaatcgggga acggtcctcg     720
cacacctggt tcgtgttgcg ggaattactc ggacaccaaa acgtcaagaa ctacgacggc     780
agttggacag aatacggctc cctggtgggc gccccgatcg agttgggaag c              831

<210> SEQ ID NO 39
<211> LENGTH: 300
<212> TYPE: DNA
<213> ORGANISM: M. tuberculosis

<400> SEQUENCE: 39
atgtgctctg gacccaagca aggactgaca ttgccggcca gcgtcgacct ggaaaaagaa      60
acggtgatca ccggccgcgt agtggacggt gacggccagg ccgtgggcgg cgcgttcgtg     120
cggctgctgg actcctccga cgagttcacc gcggaggtcg tcgcgtcggc caccggcgat     180
ttccggttct tcgccgcgcc cggatcctgg acgctgcgcg cgctgtcggc ggccggcaac     240
ggcgacgcgg tggtgcagcc ctcgggcgcg ggcatccacg aggtagacgt caagatcacc     300

<210> SEQ ID NO 40
<211> LENGTH: 441
<212> TYPE: DNA
<213> ORGANISM: M. tuberculosis

<400> SEQUENCE: 40
atggccaatg tggtagctga aggtgcctac ccttactgtc ggctcactga tcagccgctg      60
agtgtggacg aagtgctagc cgccgtctcg ggccccgaac aaggcggcat tgtcatattt     120
gtgggaaacg tgcgtgacca caatgccggg catgatgtca cgcggttgtt ctacgaggcg     180
tatccgccga tggtgattcg gacattgatg tcgatcatcg gacggtgtga agacaaggcc     240
gagggtgtcc gcgttgctgt cgcgcaccgg accggtgaat tgcaaatcgg tgatgccgcg     300
gtcgttattg gcgcgtcagc tccccaccgt gcggaggcat ttgacgccgc gcgtatgtgt     360
atcgagttgc ttaagcagga agtgccgatt tggaagaagg aattcagctc gaccggtgct     420
gaatgggtcg gcgatagacc a                                               441

<210> SEQ ID NO 41
<211> LENGTH: 600
<212> TYPE: DNA
<213> ORGANISM: M. tuberculosis

<400> SEQUENCE: 41
atgagtccgt ctccatcggc cctgctcgcc gaccacccgg accgcattcg ttggaacgcg      60
aaatacgagt gcgctgaccc cacggaggcg gtatttgcgc ccatatcctg gctcggcgac     120
gtgctgcagt tcggggtgcc agaagggccg gttctggaac tggcgtgcgg tcggtccggc     180
accgcgctgg ggctagccgc ggcgggccgc tgcgtgactg cgatcgacgt ttccgatacc     240
gcgttggttc agctcgagct cgaagcgacc cgacgggaat tggccgatcg cctcacactg     300
gtgcacgccg atctctgctc ctggcagtcg ggggatggac gctttgctct ggtactttgc     360
cgactattct ggcatccgcc cacttttcgc caggcttgcg aggctgtggc gccgggcggt     420
gtagtggcgt gggaggcatg gcggcggccc atcgatgtcg ctcgggatac ccgtcgagcc     480
gaatggtgct tgaagccagg ccagcccgag tctgaacttc ccgccggctt cacggtgatt     540
cgggtggtcg acaccgatgg ttcagagccg tcgcggcgca tcatcgccca acggtcactg     600

<210> SEQ ID NO 42
<211> LENGTH: 1200
```

-continued

<212> TYPE: DNA
<213> ORGANISM: Mycobacteria tuburculosis

<400> SEQUENCE: 42

```
atgacaagca cctcgattcc gacgttcccg ttcgaccggc cggtcccgac ggagccgtcc     60
ccaatgctgt cggaactgag aaacagctgt ccggtagccc cgatagagtt gccctcgggg    120
cacacagcat ggctcgtcac tcgctttgac gatgtaaagg gagtgctgtc cgacaagcgt    180
ttcagctgca gggcggcagc gcacccgtcg tcgcccccgt tcgtgccgtt cgtgcagctt    240
tgccccagct tgttgagcat cgatgggccc caacacaccg cggcccgccg tctgctcgcg    300
cagggcctaa atcccggctt catcgcacgc atgcggcccg ttgtccaaca gatcgtcgac    360
aatgcgctcg acgatctggc agccgcggaa ccaccggtgg acttccagga aatagtaagt    420
gtccctatcg gagaacagct catggccaag ctactcgggg tcgagcccaa aaccgtgcac    480
gagctcgcgg cgcacgtgga tgcggcgatg tccgtgtgtg agatcggcga cgaggaggtg    540
agccggcggt ggtcagcact gtgcacgatg gtcatcgaca tactgcaccg caagctcgcc    600
gaaccgggtg atgacctact tagcacgatc gcccaggcga accggcaaca gtccaccatg    660
accgacgagc aggttgtcgg catgctcctc accgtcgtga tcggaggagt cgacacaccg    720
atcgccgtga tcacaaacgg gctggcgagc ctgctgcacc accgcgatca atatgaacgg    780
ctcgttgaag acccaggccg tgtcgctcgt gcggttgaag aaatagtccg gtttaatccg    840
gcaactgaaa ttgagcactt gcgagttgtc accgaggatg tcgtcattgc cggaaccgcg    900
ctatcggcgg ggagcccagc atttacctct atcacttcgg ctaaccgcga ctccgaccaa    960
ttcctggacc ccgatgagtt tgatgtcgaa cgtaatccga acgaacacat agcatttgga   1020
tatggtccac atgcttgccc ggcctcagcg tattcacgca tgtgcttgac gacgttcttc   1080
acctcgctta cccagcgatt tccgcaactt caactcgcaa gaccgtttga ggatttggaa   1140
cgacggggta agggcctaca ttcggtgggg atcaaggaac tccttgttac ctggccgacg   1200
```

<210> SEQ ID NO 43
<211> LENGTH: 498
<212> TYPE: DNA
<213> ORGANISM: Mycobacteria tuburculosis

<400> SEQUENCE: 43

```
gtgcgcattg tcaatgcggc ggacccattt tcgatcaacg atctaggctg tggctatggg     60
gctctactgg actacctaga tgcgcgtggc ttcaaaactg attacaccgg catcgacgtc    120
tcccccgaaa tggtgcgcgc ggccgcacta cgtttcgaag gtcgggcgaa cgcagacttc    180
atctgcgcgg cgcgcataga tcgggaggcg gactatagcg tcgcgagtgg aatattcaat    240
gttcgtctga aatcgttgga cacggaatgg tgcgctcaca tcgaagcgac gctcgacatg    300
ctgaatgccg cgagtcgccg tggcttctct tttaattgcc tgacatctta ttccgatgca    360
tcaaagatgc gcgacgacct gtactatgct gacccatgcg ccctatttga tctctgcaag    420
cgcaggtact ccaagagtgt tgcgcttctg cacgactacg gcttgtatga attcacaatt    480
ctggttagga aggcgtca                                                 498
```

<210> SEQ ID NO 44
<211> LENGTH: 693
<212> TYPE: DNA
<213> ORGANISM: Mycobacteria tuburculosis

<400> SEQUENCE: 44

-continued

```
ttgaagaaag tcgcgattgt tcaatcaaat tacatacctt ggcgaggata ttttgacctg      60
attgcattcg tcgatgaatt catcatctat gatgacatgc aatataccaa gcgtgattgg     120
cgaaacagaa atcggatcaa aacgagccag gggttacagt ggataactgt tcccgtccag     180
gtgaagggac gtttccatca aaagatacgt gagacgctga tcgacggcac cgattgggcg     240
aaagcgcact ggcgggcact agaattcaac tacagcgcgg ccgctcattt tgcggagatc     300
gctgactggc tcgcgccgat ttacctcgaa gaacagcaca cgaatctttc cttactcaac     360
aggcgtctat tgaatgcgat tgcagttat ctcggtatca gcacgcgact ggcaaattcg     420
tgggactacg aattagccga cggcaagacc gagagactgg ccaacctctg ccaacaggcc     480
gcagcgaccg aatatgtctc tggcccctca gcccgttcgt atgtcgatga gcgcgtgttc     540
gacgaactta gcatccgggt aacttggttc gattatgacg gctaccgcga ttataagcaa     600
ttgtggggag ggttcgagcc cgccgtgtcg attctggatc tgctctttaa cgtcggagcc     660
gaggctccgg actatttgag gtactgtcgc cag                                  693
```

<210> SEQ ID NO 45
<211> LENGTH: 395
<212> TYPE: DNA
<213> ORGANISM: Mycobacteria tuburculosis
<220> FEATURE:
<221> NAME/KEY: misc_feature
<222> LOCATION: (1)...(395)
<223> OTHER INFORMATION: n = A,T,C or G

<400> SEQUENCE: 45

```
vvmsartgva rhgtsgrgcg dvgargndvs vatrkrsrgd rvgnhgarar rmkrvrgavt      60
asrrwagssr tmgtasvsaa tayaswyavd vstvvgdcwd wgmngrhcsd yamvaaagna    120
dysadytava awaaryagsh wgargcyvat mavsawaarg argrvvvtga aaawgvdrgn    180
stgvvaayva srrwgattva vvkvvgvvaa rwrwaggtgv vvsnaawrgg tashgknssg    240
grdrnvsgka dsknysgkgt grtgavvvvv avagrrvmvg vatatsadva yyvvaavard    300
nggagdaahg drrravgvcv savasvnvav gyvyggakgv vgttvttvtw awvtcvvvsy    360
arkarhdshn gtrsddtaas ttscnvssrg gcnyt                                395
```

<210> SEQ ID NO 46
<211> LENGTH: 879
<212> TYPE: DNA
<213> ORGANISM: Mycobacteria tuburculosis

<400> SEQUENCE: 46

```
gtgtttgcgt tgagtaataa tctgaaccgt gtgaacgcat gcatggatgg attccttgcc      60
cgtatccgct cacatgttga tgcgcacgcg ccagaattgc gttcactgtt cgatacgatg    120
gcggccgagg cccgatttgc acgcgactgg ctgtccgagg acctcgcgcg gttgcctgtc    180
ggtgcagcat tgctggaagt gggcgggggg gtacttctgc tcagctgtca actggcggcg    240
gagggatttg acatcaccgc catcgagccg acgggtgaag gttttggcaa gttcagacag    300
cttggcgaca tcgtgctgga attggctgca gcacgaccca ccatcgcgcc atgcaaggcg    360 gaagactta tttccgagaa gcggttcgac ttcgccttct cgctgaatgt gatgagcac     420 atcgaccttc cggatgaggc agtcaggcgg gtatcggaag tgctgaaacc gggggccagt    480
taccacttcc tgtgcccgaa ttacgtattc ccgtacgaac cgcatttcaa tatcccaaca    540
ttcttcacca aagagctgac atgccgggtg atgcgacatc gcatcgaggg caatacgggc    600
atggatgacc cgaagggagt ctggcgttcg ctcaactgga ttacggttcc caaggtgaaa    660
```

-continued cgctttgcgg cgaaggatgc gacgctgacc ttgcgcttcc accgtgcaat gttggtatgg 720
atgctggaac gcgcgctgac ggataaggaa ttcgctggtc gccgggcaca atggatggtc 780
gctgctattc gctcggcggt gaaattgcgt gtgcatcatc tggcaggcta tgttcccgct 840
acgctgcagc ccatcatgga tgtgcggcta acgaagagg 879

<210> SEQ ID NO 47
<211> LENGTH: 1296
<212> TYPE: DNA
<213> ORGANISM: Mycobacteria tuburculosis

<400> SEQUENCE: 47
atgtacgaga gacggcatga gcgcggaatg tgcgaccgtg ccgtcgagat gaccgacgtc 60
ggcgctacgg cagcccccac cggacctatc gcgcggggca gcgtcgctcg ggtcggcgcg 120
gcgaccgcgt tggccgttgc ctgcgtctac acggtcatct atctggcggc ccgcgaccta 180
cccccggctt gtttttcgat attcgcggtg ttttgggggg cgctcggcat tgccaccggc 240
gccacccacg gcctcctgca agaaacgacc cgcgaggtcc gctgggtgcg ctccacccaa 300
atagttgcgg gccatcgtac ccatccgctg cgggtggccg ggatgattgg caccgtcgcg 360
gccgtcgtaa ttgcgggtag ctcaccgctg tggagccgac agctattcgt cgaggggcgc 420
tggctgtccg tggggctact cagcgttggg gtggccgggt tctgcgcgca ggcgaccctg 480
ctgggcgcgc tggccggcgt cgaccggtgg acacagtacg ggtcactgat ggtgaccgac 540
gcggtcatcc ggttggcggt cgccgcggca gcggttgtga tcggatgggg tctggccggg 600
tacttgtggg ccgccaccgc gggagcggtg gcgtggctgc tcatgctgat ggcctcgccc 660
accgcgcgca gcgcggccag cctgctgacg cccgggggaa tcgccacgtt cgtgcgcggt 720
gccgctcatt cgataaccgc cgcgggtgcc agcgcgattc tggtaatggg tttcccagtg 780
ttgctcaaag tgacctccga ccagttaggg gcaaagggcg gagcggtcat cctggctgtg 840
accttgacgc gtgcgccgct tctggtccca ctgagcgcga tgcaaggcaa cctgatcgcg 900
catttcgtcg accggcgcac ccaacggctt cgggcgctga tcgcaccggc gctggtcgtc 960
ggcggcatcg gtgcggtcgg gatgttggcc gcagggctta ccggtccctg gttgctgcgt 1020
gttggattcg gccccgacta ccaaactggc ggggcgttgc tggcctggtt gacggcagcg 1080
gcggtagcta tcgccatgct gacgctgacc ggcgccgccg cggtcgcggc cgcactgcac 1140
cgggcgtatt tgctgggctg ggtcagcgcg acggtggcgt cgacgctgtt gctgctgctg 1200
ccgatgccgc tggagacgcg caccgtgatc gcgctgttgt tcggtccaac ggtgggaatc 1260
gccatccatg tggccgcgtt ggcgcggcga cccgac 1296

<210> SEQ ID NO 48
<211> LENGTH: 1020
<212> TYPE: DNA
<213> ORGANISM: M. tuberculosis

<400> SEQUENCE: 48
gtgaagcgag cgctcatcac cggaatcacc ggccaggacg gctcgtatct cgccgaactg 60
ctgctggcca aggggtatga ggttcacggg ctcatccggc gcgcttcgac gttcaacacc 120
tcgcggatcg atcacctcta cgtcgacccg caccaaccgg gcgcgcggct gtttctgcac 180
tatggtgacc tgatcgacgg aacccggttg gtgaccctgc tgagcaccat cgaacccgac 240
gaggtgtaca acctggcggc gcagtcacac gtgcgggtga gcttcgacga acccgtgcac 300

```
accggtgaca ccaccggcat gggatccatg cgactgctgg aagccgttcg gctctctcgg    360
gtgcactgcc gcttctatca ggcgtcctcg tcggagatgt tcggcgcctc gccgccaccg    420
cagaacgagc tgacgccgtt ctacccgcgg tcaccgtatg cgccgccaa  ggtctattcg    480 tactgggcga cccgcaatta tcgcgaagcg tacggattgt tcgccgttaa cggcatcttg    540
ttcaatcacg aatcaccgcg gcgcggtgag acgttcgtga cccgaaagat caccagggcc    600
gtggcacgca tcaaggccgg tatccagtcc gaggtctata tgggcaatct ggatgcggtc    660
cgcgactggg ggtacgcgcc cgaatacgtc gaaggcatgt ggcggatgct gcagaccgac    720
gagcccgacg acttcgtttt ggcgaccggg cgcggtttca ccgtgcgtga gttcgcgcgg    780
gccgcgttcg agcatgccgg tttggactgg cagcagtacg tgaaattcga ccaacgctat    840
ctgcggccca ccgaggtgga ttcgctgatc ggcgacgcga ccaaggctgc cgaattgctg    900
ggctggaggg cttcggtgca cactgacgag ttggctcgga tcatggtcga cgcggacatg    960
gcggcgctgg agtgcgaagg caagccgtgg atcgacaagc cgatgatcgc cggccggaca   1020
```

<210> SEQ ID NO 49
<211> LENGTH: 966
<212> TYPE: DNA
<213> ORGANISM: M. tuberculosis
<400> SEQUENCE: 49

```
atgaacgcgc acacctcggt cggcccgctt gaccgcgcgg cccgggtcta catcgccggg     60
catcgcggcc tggtcgggtc cgcgctgcta cgcacgtttg cgggcgcggg gttcaccaac    120
ctgctggtgc ggtcacgcgc cgagcttgat ctgacggatc gggccgcgac gttcgacttc    180
gttctcgagt cgaggccgca ggtcgtcatc gacgcggcgg cccgggtcgg cggcatcctg    240
gccaacgaca cctacccggc cgatttcctg tcggaaaacc tccagatcca ggtcaacctg    300
ctggatgccg ccgtggcggc gcgggtgccg gcctgctgt tcctgggctc gtcgtgcatc    360
tacccgaaac tcgccccgca gccgatcccg gagagcgcgc tgctcaccgg tccgttggag    420
ccgaccaacg acgcgtacgc gatcgccaaa atcgccggca tccttgcggt ccaggcggtg    480
cgccgccaac atggcctgcc gtggatctcg gcgatgccca ccaacctgta cgggccaggc    540
gacaactttt cgccgtccgg ctcgcatctg ctgccggcac tcatccgccg ctatgacgag    600
gccaaagcca gtggcgcgcc caacgtgacc aactggggca ccggcacgcc ccgacgggag    660
ttgctgcacg tcgacgacct ggcgagcgca tgcctgtatc tgctggaaca tttcgacggg    720
ccgacccatg tcaacgtggg aaccggcatc gaccacacca tcggcgagat cgccgagatg    780
gtcgcctcgg cggtaggcta tagcggcgaa acccgctggg atccaagcaa accggacgga    840
acaccacgca aactgctgga tgtttcggtg ctacgggagg cgggatggcg gccttcgatc    900
gcgctgcgcg acggcatcga ggcgacggtg gcgtggtatc gcgagcacgc gggaacggtt    960
cggcaa                                                              966
```

<210> SEQ ID NO 50
<211> LENGTH: 729
<212> TYPE: DNA
<213> ORGANISM: Mycobacteria tuberculosis
<400> SEQUENCE: 50

```
atgaggctgg cccgtcgcgc tcggaacatc ttgcgtcgca acggcatcga ggtgtcgcgc     60
tactttgccg aactggactg ggaacgcaat ttcttgcgcc aactgcaatc gcatcgggtc    120
agtgccgtgc tcgatgtcgg ggccaattcg gggcagtacg ccaggggtct gcgcggcgcg    180
```

-continued

```
ggcttcgcgg gccgcatcgt ctcgttcgag ccgctgcccg ggcccttttgc cgtcttgcag    240 cgcagcgcct ccacggaccc gttgtgggaa tgccggcgct gtgcgctggg cgatgtcgat    300
ggaaccatct cgatcaacgt cgccggcaac gagggcgcca gcagttccgt cttgccgatg    360
ttgaaacgac atcaggacgc ctttccacca gccaactacg tgggcgccca acgggtgccg    420
atacatcgac tcgattccgt ggctgcagac gttctgcggc ccaacgatat tgcgttcttg    480
aagatcgacg ttcaaggatt cgagaagcag gtgatcgcgg gtggcgattc aacggtgcac    540
gaccgatgcg tcggcatgca gctcgagctg tctttccagc cgttgtacga gggtggcatg    600
ctcatccgcg aggcgctcga tctcgtggat tcgttgggct ttacgctctc gggattgcaa    660
cccggtttca ccgaccccccg caacggtcga atgctgcagg ccgatggcat cttcttccgg    720
ggcagcgat                                                           729
```

<210> SEQ ID NO 51
<211> LENGTH: 786
<212> TYPE: DNA
<213> ORGANISM: Mycobacteria tuburculosis

<400> SEQUENCE: 51
gtgacgtctg ctccgaccgt ctcggtgata acgatctcgt tcaacgacct cgacgggttg 60
cagcgcacgg tgaaaagtgt gcgggcgcaa cgctaccggg gacgcatcga gcacatcgta 120
atcgacggtg gcagcggcga cgacgtggtg gcatacctgt ccgggtgtga accaggcttc 180
gcgtattggc agtccgagcc cgacggcggg cggtacgacg cgatgaacca gggcatcgcg 240
cacgcatcgg gtgatctgtt gtggttcttg cactccgccg atcgtttttc cgggcccgac 300
gtggtagccc aggccgtgga ggcgctatcc ggcaagggac cggtgtccga attgtggggc 360
ttcgggatgg atcgtctcgt cgggctcgat cgggtgcgcg gcccgatacc tttcagcctg 420
cgcaaattcc tggccggcaa gcaggttgtt ccgcatcaag catcgttctt cggatcatcg 480
ctggtggcca agatcggtgg ctacgacctt gatttcggga tcgccgccga ccaggaattc 540
atattgcggg ccgcgctggt atgcgagccg gtcacgattc ggtgtgtgct gtgcgagttc 600
gacaccacgg gcgtcggctc gcaccgggaa ccaagcgcgg tcttcggtga tctgcgccgc 660
atgggcgacc ttcatcgccg ctacccgttc gggggaaggc gaatatcaca tgcctaccta 720
cgcggccggg agttctacgc ctacaacagt cgattctggg aaaacgtctt cacgcgaatg 780
tcgaaa 786

<210> SEQ ID NO 52
<211> LENGTH: 894
<212> TYPE: DNA
<213> ORGANISM: Mycobacteria tuburculosis

<400> SEQUENCE: 52
atgtcgacaa acccaggacc agccgaaggg gctaaccaag tgatggcaca ggaacattcg 60
gccggcgcgg tacaattcac cgcccacaac gttcgcctcg acgacggaac cttgacgata 120
ccggagtcct cgcgcacgtt agacgaatcg tcctggttca tctcggcgcg cgggattctg 180
gaaaccgtct ttcccgggga caagagccac ctacgcctgg ccgatgtcgg ctgcttggaa 240
ggcgggtacg cggtcgggtt cgcgcgcatg ggatttcagg tcctcgggat cgaggttcgc 300
gagctgaaca tggcggcctg caactacatc aaatcgaaga ccaacctgcc gaatctccgg 360
ttcgtccacg acaacgccct caacatcgcc aaccacgggc tcttcgatac cgtcttctgc 420

```
tgcggcctct tctaccacct ggagaatccg aagcaatacc tggaaaccct ctcgtcggta      480
acgaacaagc tgctgattct ccagacgcac ttctcgatca tcaaccggag cgataaatgg      540
ctccggttgc ccacgacggc acgacaattg accgatcggt tgctgcggcg gccggcgccg      600
gtgaagttca tgctctcggc gcccaccgaa catgagggac ttcccggtag gtggtttacc      660
gagttttccg acgaccgctc gtttggccag cgcgacaccg caaaatgggc gtcctgggac      720
aatcgccggt cattctggat tcaacgcgag cacctacttc aggccatcaa agacgtcggc      780
gtcgacctgg tgatggagga gtacgacaac ttggaaccaa gcatcgccga gtcgttgctc      840
ggaggttcct atgcggcgaa tcttcgaggc accttcatcg gtatcaagac ccgg           894
```

<210> SEQ ID NO 53
<211> LENGTH: 1119
<212> TYPE: DNA
<213> ORGANISM: Mycobacteria tuburculosis

<400> SEQUENCE: 53

```
gtgccgtacg tccgccgacc accaggccac gacggccgac ggccggcggg cacaggcgat       60
tcacgttcgc catcgcaata cccttgcggc cgcgcaggaa aagggccgac ggtgagtccc      120
cagctttgcc ccaaggtgag catcgtctcg accactcaca accaggcggg ctacgcccgt      180
caggccttcg acagctttct cgaccagcaa accgacttcc cggtggagat catcgtcgcc      240
gacgacgcgt cgaccgatgc caccccggcg atcatccgtg agtacgccga gcggtacccg      300
cacgtgttcc ggccgatctt caggaccgaa aacctcggcc tcaatgggaa cctgaccggc      360
gccctgtcgg ccgctcgcgg cgagtacgtc gcgttgtgcg aggcggacga ctactggatc      420
gatccgctga agctaagcaa acaggtcgca ttcctcgacc ggcaccccaa gacgacggtg      480
tgcttccatc ccgtccgagt gatatgggag gacggccatg ccaaggactc gaagttcccc      540
ccggttcggt gcggggcaa cttgagcctg gatgcgttga tcttgatgaa cttcatccag      600
accaactcgg ccgtgtaccg tcgcctcgag cgctacgacg acattcctgc cgacgtcatg      660
cccctggact ggtatctgca cgtccggcac gcggtgcatg cgacatcgc catgttgccc       720 gacaccatgg ccgtgtatcg ccgccacgcc caaggcatgt ggcacaacca ggtggtggac      780
ccgccaaagt tctggttgac gcagggtccg ggcatgcgg cgacgtttga cgcgatgctc      840
gacctgttcc cggagaccc cgcgcgcgag gagctcatcg ccgtcatggc cgactggatc      900
cttcgccaga tcgccaacgt tccaggcccg gaggggcgcg ccgcgctgca ggaaaccatc      960
gcgcgccatc cccggatcgc catgctggcg ctgcagcacc gcggggcgac acccgcgcgg     1020
cggctcaaga cccagtggcg caagctcgcc gccgcgacgc cgagccgcag ggggctcgtg     1080
gatgtgtggc cctcccggct ccgacgcggc tgtcgagcc                            1119
```

<210> SEQ ID NO 54
<211> LENGTH: 282
<212> TYPE: DNA
<213> ORGANISM: Mycobacteria tuburculosis

<400> SEQUENCE: 54

```
atgaccatca actatcagtt cggtgatgtc gacgctcatg gcgccatgat ccgcgctcag       60
gccgggttgc tggaggcgga gcatcaggcc atcgttcgtg atgtgttggc cgcgggtgac      120
ttttggggcg cgccggttc ggtggcttgc caggagttca tcacccagct gggccgtaac      180
ttccaggtga tctacgagca ggccaacgcc cacgggcaga aggtgcaggc tgccggcaac      240
aacatggcac aaaccgacag cgccgtcggc tccagctggg cc                        282
```

<210> SEQ ID NO 55
<211> LENGTH: 294
<212> TYPE: DNA
<213> ORGANISM: Mycobacteria tuburculosis

<400> SEQUENCE: 55

```
atggcaacac gttttatgac ggatccgcac gcgatgcggg acatggcggg ccgttttgag     60
gtgcacgccc agacggtgga ggacgaggct cgccggatgt gggcgtccgc gcaaaacatc    120
tcgggcgcgg gctggagtgg catggccgag gcgacctcgc tagacaccat ggcccagatg    180
aatcaggcgt ttcgcaacat cgtgaacatg ctgcacgggg tgcgtgacgg gctggttcgc    240
gacgccaaca actacgagca gcaagagcag gcctcccagc agatcctcag cagc          294
```

<210> SEQ ID NO 56
<211> LENGTH: 324
<212> TYPE: DNA
<213> ORGANISM: Mycobacteria tuburculosis

<400> SEQUENCE: 56

```
gtgcttttgc ctcttggtcc gcctttgccg cccgacgcgg tggtggcgaa acgggctgag     60
tcgggaatgc tcggcgggtt gtcggttccg ctcagctggg gagtggctgt gccacccgat    120
gattatgacc actgggcgcc tgcgccggag gacggcgccg atgtcgatgt ccaggcggcc    180
gaaggggcgg acgcagaggc cgcggccatg gacgagtggg atgagtggca ggcgtggaac    240
gagtgggtgg cggagaacgc tgaaccccgc tttgaggtgc cacggagtag cagcagcgtg    300
attccgcatt ctccggcggc cggc                                           324
```

<210> SEQ ID NO 57
<211> LENGTH: 1524
<212> TYPE: DNA
<213> ORGANISM: M. tuberculosis

<400> SEQUENCE: 57

```
atgtcacgcc gagcattcct ggctaaggcg gctggagccg gggcagcggc ggttttgacg     60
gactgggccg caccggtgat cgaaaaggcc tatggtgccg gtccctgctc gggtcatttg    120
accgatatcg agcacatcgt gctgtgccta caggagaaca ggtcgttcga tcactatttc    180
ggcacgcttt ctgccgtcga cgggttcgac actccgacgc cgctgtttca acaaaagggc    240
tggaacccgg agacgcaggc gctggacccc accggcatta cgctgcccta ccgcatcaat    300
accaccgggg gtcccaacgg ggttggcgag tgcgtcaacg acccagacca ccagtggatt    360
gccgcgcact tgtcatggaa cggcggcgcc aatgacggct ggctgccggc gcaggcgcgg    420
acccggtcgg tggccaacac gcccgtggtg atgggctatt acgcacgtcc tgacataccg    480
atccactact tgttggccga taccttcacg atctgcgacc agtacttctc gtcgcttctt    540
ggcgggacga tgcctaaccg gctctattgg atcagcgcca ccgtcaatcc cgacggggat    600
caaggtgggc cgcagatcgt cgaacccgcc atccagccga agttgacctt cacctggcgc    660
atcatgccgc agaacctcag tgacgccggc atcagttgga aggtgtacaa cagcaagctg    720
ctcggcgggc tcaacgacac ttccttgagc cgtaacgggt atgtgggcag tttcaaacag    780
gccgcagatc cgaggtcgga cctggcccgt tatggcatcg ccccggccta cccgtgggat    840
ttcatccgcg acgtcatcaa caacacgctg ccccaggtgt cctgggtcgt tccgttgacc    900
gtcgagtccg aacatccgtc attcccggtg gcagtcggtg cggtgacgat cgtgaacttg    960
```

-continued

```
ataagggtgt tgctgcgcaa tccggcggtg tgggagaaaa ccgcgttgat catcgcctat    1020
gacgaacatg gcggcttctt cgaccacgtc acaccgctca ccgcgccgga gggcacaccc    1080
ggcgaatgga ttcccaacag tgttgacatc gacaaggtcg acggctccgg cggaatacgt    1140
ggacccatcg gcttgggctt tcgcgtgccc tgcttcgtca tttcgcctta cagtcgcggc    1200
gggctgatgg tccatgatcg gttcgaccac acatcgcagc tgcaattgat cggcaagcgt    1260
ttcggggtgc cggttcccaa cttgacaccc tggcgtgcca gtgtcaccgg cgatatgacg    1320
tcggcattca atttcgcggc cccgccggac ccgtcgccac ccaatctgga ccacccggtc    1380
cgtcaattgc cgaaggtcgc caagtgcgtg cccaatgtgg tgctgggttt cttgaacgaa    1440
ggcctgccgt atcgggtgcc ctaccccaa acaacgccag tccaggaatc cggtcccgcg    1500
cggccgattc ccagcggcat ctgc                                           1524
```

<210> SEQ ID NO 58
<211> LENGTH: 1536
<212> TYPE: DNA
<213> ORGANISM: M. tuberculosis

<400> SEQUENCE: 58

```
atgtcacgtc gagagttttt gacaaagctc actggcgcag gcgcagcggc attcctgatg     60
gactgggctg caccggtgat tgaaaaggcc tacgcgccg gccttgtcc cggacatttg     120 accgacatcg agcatatcgt gttgctgatg caggagaacc ggtcattcga ccactatttc    180
ggaacgcttt ccagcaccaa tgggttcaac gccgcgtcgc cggcattcca acaaatgggt    240
tggaacccca tgacgcaggc gttggacccc gccggggtca ccattccgtt ccgcttggac    300
accacccgag gcccttcct ggacggcgag tgcgtcaacg accccgagca ccagtgggtg    360
gggatgcacc tggcctggaa cggtggtgcc aacgacaact ggctgccggc gcaggcgacc    420
acccgcgcag gaccatatgt cccctttgacc atgggttact acacgcgcca agacatcccg    480
atccactatc tgctggccga cacgttcacc atctgcgacg gctaccattg ctcgctgctg    540
acgggcaccc tgcccaaccg gctctactgg ttgagcgcca acatcgaccc cgccggcacc    600
gacgggggac cccaattggt agagccgggc ttcctgccgc tgcagcaatt cagttggcgc    660
atcatgccgg aaaacctcga agatgccggg gtcagctgga aggtgtacca gaacaagggc    720
ctcgggcgat tcatcaacac gcccatcagc aataacgggc tggtgcaggc cttccgccag    780
gcagctgatc cgaggtcgaa cttggcccgc tacggtatcg ccccgaccta ccctggggac    840
ttcgctgccg acgtcagggc caaccggcta cccaaggtct cctggttagt tcccaacatc    900
ctgcagtccg aacaccccgc cctgccgta gcgcttggcg cggtgtccat ggtgaccgcg    960
ctgcggatct tgctgtccaa tccgcggtg tgggaaaaga ccgcacttat cgtcagctat   1020
gacgagaacg gcggcttctt cgaccacgtc acgcccccca cggcaccgcc cgggacaccc   1080
ggcgaattcg tcacggtgcc caacatcgac gcagtacccg ggtccggtgg cattcgtggt   1140
ccgctcggtc tgggttttcg cgttccctgc attgtcattt gccgtacag ccgcggcccg   1200 ctgatggtct ccgacacgtt cgaccacacc tgcaattga agttgattcg cgcccggttc   1260
ggcgtgccgg ttcccaacat gaccgcctgg cgcgacggcg tggttggcga catgacctca   1320
gcgttcaact tgcgactcc accgaattcg accagaccca acttgagcca cccgttgctg   1380
ggagcgctgc cgaagctgcc gcagtgcatc cctaacgtgg tgttgggaac caccgacggc   1440
gcgttgccga gcattcccta tcgggtgccc tatccgcagg tgatgccaac tcaggaaacc   1500
acacccgtcc gcgggactcc cagcgggctg tgcagc                             1536
```

<210> SEQ ID NO 59
<211> LENGTH: 1536
<212> TYPE: DNA
<213> ORGANISM: M. tuberculosis

<400> SEQUENCE: 59

| |

```
gcggcgttgg cggccacggt gcatccggcg gcggtgacgg cgaatcgggt gttgttgggg      360
gcgttggtgg cgacgaacat tttgggtcag aacacgccgg cgattgcggc cactgagttc      420
gattatgtgt agatgtgggc tcaggacgtg ggtgcgatgt ggggtatca cgcggggcg        480 gcggcggtgg ctgagacgtt gacgccgttt agtgtgccgc cgctggattt ggcggggttg      540
gcttcccagg ccggtgcgca gttgaccggg atggcgacgt cggtttcggc tgcgttgtct      600
ccgatcgcgg agggtgcggt ggaggggtg ccggctgtgg tggctgcggc gcagtcggtg       660
gcggcggggt tgccggtgga tgcggcgctg caggtgggc aggccgcggc gtatccggcc       720
agtatgttga ttgggccgat gatgcagttg gcgcagatgg ggactacggc caacacggct     780
gggttggccg gtgcggaggc tgcggggttg gctgcggcgg atgtgccgac gtttgccggt     840
gatatcgctt cggggacggg cctaggtggt gccggtggtc tgggtgcggg gatgtcggcg      900
gagttgggta aggcgcggtt ggtggggcg atgtcggtgc ctccgacctg ggaggggtcg       960
gttcctgcgc ggatggccag ttcggcgatg gcgggtttgg gggctatgcc tgctgaggtg     1020
ccggcggcag gcgggcccat ggggatgatg ccgatgccga tgggtatggg gggtgctggg    1080
gcgggtatgc cggccgggat gatgggccgc ggtggcgcaa atccgcatgt ggtgcaggct     1140
cggcccagtg tggtgccgcg ggtcgggatc gga                                  1173

<210> SEQ ID NO 61
<211> LENGTH: 1062
<212> TYPE: DNA
<213> ORGANISM: Mycobacteria tuburculosis

<400> SEQUENCE: 61 atgccgggc ggttcagaaa cttcggtagc caaaacctgg gtagcggcaa catcggcagc        60
accaacgtgg gcagcggcaa catcggcagc accaacgtgg gcagcggcaa catcggcgac      120
acgaacttcg gtaacggaaa caacggcaac ttcaactttg gtagcggcaa taccggcagt      180
aacaacatcg gcttcggaaa caccggcagc gggaatttcg gtttcggaaa cacgggcaac      240
aacaacatcg gtatcgggct caccggcgat ggtcagatcg gcatcggcgg actgaactcg      300
ggcagcggaa acatcggtttt cgggaactcc ggcaccggaa acgtcggtttt gttcaactcc    360 ggcaccggca acgtaggctt cgggaactcc ggtactgcga acactggatt cgggaacgcg      420
ggcaacgtca acaccggatt ttggaacggc ggcagcacaa acactggcct cgctaacgcc     480
ggcgccggca acacaggctt tttcgacgct ggcaactaca acttcggcag tcttaacgcc     540
ggaaacataa actcgagttt tgggaattcg ggtgacggca acagtggttt cctcaatgct     600
ggcgacgtca actccggtgt gggcaatgcg ggtgatgtca acactggctt agggaactcg     660
ggcaacatca atactggtgg gtttaatccg gcacgctca acacgggctt cttcagcgcg      720
atgacccaag ctggtccgaa ttcgggcttc ttcaacgccg gtaccggtaa ctctggtttc     780
gggcacaacg acccggctgg cagtggcaac tcgggcattc agaactcggg cttcggcaac    840
tcgggctatg tcaataccag caccacaagc atgttcggcg gtaactcagg ggtgctcaac     900
acgggctacg gcaactcagg tttctataac gcggccgtca caacaccgg gatttttgtg      960 accggcgtga tgagttcggg attttttcaat tttgggacgg gcaactcggg cctgctggtc   1020
agcggcaatg ggctttcggg tttcttcaag aacttgttcg ga                       1062

<210> SEQ ID NO 62
<211> LENGTH: 654
<212> TYPE: DNA
<213> ORGANISM: Mycobacteria tuburculosis
```

-continued

<400> SEQUENCE: 62
atgagccgac tcctagcttt gctgtgcgct gcggtatgca cgggctgcgt tgctgtggtt 60
ctcgcgccag tgagcctggc cgtcgtcaac ccgtggttcg cgaactcggt cggcaatgcc 120
actcaggtgg tttcggtggt gggaaccggc ggttcgacgg ccaagatgga tgtctaccaa 180
cgcaccgccg ccggctggca gccgctcaag accggtatca ccacccatat cggttcggcg 240
ggcatggcgc cggaagccaa gagcggatat ccggccactc cgatgggggt ttacagcctg 300
gactccgctt ttggcaccgc gccgaatccc ggtggcgggt tgccgtatac ccaagtcgga 360
cccaatcact ggtggagtgg cgacgacaat agccccacct ttaactccat gcaggtctgt 420
cagaagtccc agtgcccgtt cagcacggcc gacagcgaga acctgcaaat cccgcagtac 480
aagcattcgg tcgtgatggg cgtcaacaag gccaaggtcc caggcaaagg ctccgcgttc 540
ttctttcaca ccaccgacgg cgggcccacc gcgggttgtg tggcgatcga cgatgccacg 600
ctggtgcaga tcatccgttg gctgcggcct ggtgcggtga tcgcgatcgc caag 654

<210> SEQ ID NO 63
<211> LENGTH: 489
<212> TYPE: DNA
<213> ORGANISM: Mycobacteria tuburculosis

<400> SEQUENCE: 63
gtgtgctgca atggcgtggt gactccgggt gatccagccg acattgcagc gatcaaacag 60
ctcaaatacc ggtatctgcg ggcattggac accaagcatt gggacgactt caccgacacc 120
ctggccgagg atgtcaccgg cgattacggg tcatcggtcg gtacggagct gcacttcacc 180
aaccgcgccg acctggtcga ctacctgcgc caggcactcg gcccgggtgt catcaccgaa 240
caccgggtca cccatccgga aatcaccgtg accggcgata ccgcaaccgg catctggtac 300
ctgcaagacc gggtcatcgt cgccgagttc aatttcatgc tcatcggcgc cgcgttctac 360
cacgaccagt accgacgaac caccgacggc tggcggatca gcgccaccgg ctacgaccga 420
acctacgagg cgaccatgtc gttggcgggc cttaacttca acatcaggcc gggccgcgcg 480
ctggccgat 489

<210> SEQ ID NO 64
<211> LENGTH: 1227
<212> TYPE: DNA
<213> ORGANISM: Mycobacteria tuburculosis

<400> SEQUENCE: 64
atgagccaat cccggtacgc ggggttgtcc cgcagcgagc tggcagttct gttacccgag 60
ctgttgttga tcggccagct gatcgaccga tcgggcatgg cctggtgtat acaggcattc 120
ggccgccagg agatgctgca gatcgccatc gaggagtggg cgggcgccag cccgatctac 180
accaagcgca tgcaaaaggc gctgaacttc gagggcgacg acgtgcccac catcttcaag 240
gggctacagc tcgacatcgg cgcgccgccg caattcatgg acttccgttt caccctgcac 300
gaccgctggc acggcgagtt tcacctcgac cactgcggtg cgctgctcga cgtggagccg 360
atgggcgacg actacgtcgt cggcatgtgc cacaccatcg aagatccgac gttcgacgcc 420
accgcgatcg cgaccaaccc gcgcgcgcag gtgcgcccca tccaccggcc gccccgcaag 480
ccggccgacc ggcatccgca ctgtgcgtgg accgtcatca tcgacgagtc ctatcccgag 540
gctgagggta ttccggcgct ggacgcggtc cgtgaaacca aagctgccac ctgggaatta 600

-continued

```
gacaacgtcg atgcgtctga cgacgggctg gtggactatt cgggtccgct ggtgtccgac      660
ctggacttcg gggcgttctc gcattccgca ctggtgcgga tggccgatga ggtctgcctg      720
caaatgcacc tgctgaatct gtcgttcgcc attgccgtgc ggaaacgggc caaagccgat      780
gctcaactgg ccatttcggt gaacacccgc cagttgatcg gagtggccgg gctgggcgca      840
gaacgcattc accgtgcgat ggctttaccc ggcggaatcg aaggcgcgtt aggtgtgctg      900
gagctacacc cgctgctcaa cccggccggt tacgtgctgg ccgaaacgtc gccggaccgt      960
ctggtggtgc acaactcgcc agcccacgcc gacggcgcct ggatttcgtt gtgcacaccg     1020
gcatccgtgc agccgttgca ggccatcgcc accgctgtag acccgcatct gaaggttcgg     1080
atcagcggga cggacaccga ctggaccgcg gaactcatcg aggccgatgc cccagcgagc     1140
gaactgccgg aggtgttggt agccaaggtc agtcgcggat cggtcttcca gttcgagccg     1200
aggcgctcac tgccgttgac cgtgaaa                                        1227
```

<210> SEQ ID NO 65
<211> LENGTH: 1860
<212> TYPE: DNA
<213> ORGANISM: Mycobacteria tuburculosis

<400> SEQUENCE: 65

```
atgtacgacc cgctggggtt gtcgatcggg accacaaacc tggtcgcggc gggtaacgga       60
ggtccgccgg ttactcgtcg cgccgtgctg accctgtacc cgcattgcgc accgaaaatc      120
ggtgtgccta gccagaaccc gaacttgatc gagccgggcg ccctaatgag cggctttgtt      180
gagcgcattg gagatgcggt ggcgctggtg tctcccgacg gatccgtgca cgatccagac      240
ctcttgctgg tcgaggcgct ggatgcgatg gtgctgaccc ccgtgcggga cgcgagttcc      300
tcggagatcg ccattgccgt tcccgcgcat ggaagcccg agctgtaca cgcactgcgt       360 aacggtttgc ggacgcacgt cggcttcgtc cgcagcggca tggcgccgcg cctggtttcc      420
gatgcgatcg cggcgttgac cgcggtgaac tcggaattgg cctgccccca cggcagtgtg      480
gtggggttgc ttgatttcgg tggctccgcg acttacgtca ccttggtgga gaccaagtcg      540
gattccagga cgtcggattt ccagcccgtt agtgccacgg cacggtacca ggactttcc      600 ggtagtcaga tcgaccaggc tttgctgctt cgggtcatcg accaattcgg gtacggcgat      660
gacgtcgatc cggccagtac cgccgcggtc gggcaactcg ccaactcag ggagcagtgc      720 cgtgcggcaa aggaacgact gtccaccgac gttgccacgg aattgttcgc tgagcttgcc      780
gggtgcagct cgagcatcga gatgactcgg gaacagctcg aagacctgat ccaggatcca      840
ttgaccggct tcatctacgc gttcgacgac atgctgcgc ccacaacgc gagctgggcg       900 gatctcgcgg cggtggtcac cgtcggcggt ggtgccaata ttccccttgt gactcaacgt      960
ctttcgttcc acactcgtcg acctgtgctg accgcgtcgc aacccgggtg cgcggcggcg     1020
atgggtgcgt tgctgctcgc caaccgtggg ggagagcgcg attcgcgaac gcggacgtcc     1080
atcggcctcg ccacggccgc agccgccggc accagtgtca tcgagctgcc ggccggcgac     1140
gtcatggtca tcgaccatga ggccttgacc gatcgcgagt tggcctggtc gcagaccgac     1200
ttcccaagcg aagctccggc gcgtttcgag ggcgactcgt ataacgaagg cggcccctgc     1260
tggtcgatgc gtctgaacgc ggtcgagccc cccaaaggac cagcgtggcg gcgaatccgg     1320
gtgtcgcagt tgctcatcgg ggtgtcggcg gtagtggcca tgaccgcgat cgggggcgtg     1380
gcattgacgt tgacagccat cgagagacgc ccaagcccgc taccaacccc aattgtgccc     1440
ggcctggccc cgatgccgcc cggatccgtc gtgcctagct cgcgcgcacc gaccccgccg     1500
```

| | |
|---|---:|
| ccaccgccgt cgaccgttgc gccgcttccc agtgcggcac cggccccgac gacggtcgcg | 1560 |
| ccggcaccgc cgccgcccac acaggtggtg acgaccacga cagcgccacc cgtcaccacg | 1620 |
| acgccgaggc cgtcgccgac caccacaacg accaccgcgc caccgtcgac aacgacgaca | 1680 |
| accgagccgc cggtgacgac cacttcgacg attccaacga ttccgacgac tacgacgacg | 1740 |
| gtgaagatga ccacggagtg gttgcacgtc ccgttttgc ccgttccgat cccggtcccg | 1800 |
| attccgcaaa tccgggtgc cggcgaaccg cagaacccgt tcggaagcct tggctctggg | 1860 |

<210> SEQ ID NO 66
<211> LENGTH: 720
<212> TYPE: DNA
<213> ORGANISM: M. tuberculosis
<400> SEQUENCE: 66

| | |
|---|---:|
| atgatccgat tggtccgtca ttcgatcgcc ctggtggccg ccggccttgc cgccgcattg | 60 |
| tcggggtgcg attcccacaa ctcgggatcg ctcggtgccg atccgcggca ggtgaccgtg | 120 |
| ttcggatccg ggcaagtgca gggtgtgccg gacacgttga tcgctgacgt cggcattcag | 180 |
| gtcaccgcgg ccgacgtcac cagcgcgatg aaccagacca atgatcgcca gcaagcggtg | 240 |
| atcgatgcac tggtgggtgc cggcctggac cgcaaggaca tccgcaccac cagggtcacc | 300 |
| gtggcaccgc agtacagcaa tccggagccg gccggaaccg ccaccatcac cgggtatcgg | 360 |
| gcagacaacg acatcgaggt gaagatccac ccgaccgacg ccgcgtcgcg gctgctggcc | 420 |
| ctcgtcgtca gcaccggcgg tgacgccacc cggatcagct cggtcagcta ctcgattggc | 480 |
| gacgactcgc agctggtgaa ggatgcccgg gcgcgcgcct tccaagacgc caagaaccgt | 540 |
| gcggaccagt acgcacaact gtcggggctg cggctaggca aggtgatctc gatctccgag | 600 |
| gcatctggcg ccgcgcccac gcacgaggcg ccggcgccgc cgcgcggcct atccgcggtg | 660 |
| ccgctggaac ccggccagca gacggtgggc ttctcggtca cggtggtctg ggaactgacc | 720 |

<210> SEQ ID NO 67
<211> LENGTH: 297
<212> TYPE: DNA
<213> ORGANISM: Mycobacteria tuburculosis
<400> SEQUENCE: 67

| | |
|---|---:|
| atgtcgatca tgcacgccga gccagagatg ctggctgcga ccgcgggga actgcagtcg | 60 |
| atcaacgccg ttgcgcgggc cggaaatgca gcggtggcgg gcccgacgac gggtgtggtt | 120 |
| ccggccgccg ctgatttggt gtccctgcta accgcctccc agtttgccgc gcatgcacag | 180 |
| ctgtaccagg cgattagtgc cgaggcgatg gcggtccagg agcagttggc gaccacgctg | 240 |
| ggcatcagcg ccggttcata tgcggccacc gaggctgcca acgccgccac gatcgct | 297 |

&l

-continued

```
gccgggcagg ccgagcaagc cggcagccaa gcggtggcag cggcgagtgc ttatgaggcg    300
gcgtttttcg cgaccgtgcc gcccccggag atcgcggcca acagggcgtt gttgatggcg    360
ttgctggcga cgaacttcct tggccagaac acggcggcga tcgcggccac cgaggcgcaa    420
tacgccgaga tgtgggccca ggatgcggcc gcgatgtacg gctatgctgg cgcgtcggcg    480
gcggcgacgc agttgtcgcc attcaatccg gcggcgcaga ccatcaaccc ggccgggctg    540
gccagccagg ccgcatctgt cggacaagct gtcagcgggg ccgcaaatgc gcaagcactc    600
accgacattc ctaaagcgtt gtttgggctt agcggaatct tcaccaatga accgccttgg    660
ctcaccgacc ttggcaaggc gctcggtttg accgggcaca cctggtcctc ggacggtagc    720
gggctcatcg tgggcggagt gcttggcgac tttgtgcagg gtgtgaccgg gtcggccgaa    780
cttgatgcca gcgtggccat ggacacgttc ggcaaatggg tctcgcccgc tcggctcatg    840
gtcacccaat tcaaggacta ctttggcctg gcgcacgacc tgccgaagtg ggcgagtgaa    900
ggcgccaaag ccgccggtga ggccgccaag gcgttgccgg ccgccgttcc ggccattccg    960
agtgctggcc tgagcggcgt tgcgggcgcc gtcggtcagg cggcgtcggt cgggggattg   1020
aaggttccgg ccgtttggac cgccacgacc ccggcggcga gccccgcggt gctggcggcg   1080
tccaacggcc tcggagccgc ggccgccgct gaaggttcga cacacgcgtt tggcgggatg   1140
ccgctcatgg gtagcggtgc cggacgtgcg tttaacaact tcgctgcccc tcgatacgga   1200
ttcaagccga ccgtgatcgc ccaaccgccg gctggcgga                           1239
```

<210> SEQ ID NO 69
<211> LENGTH: 294
<212> TYPE: DNA
<213> ORGANISM: Mycobacteria tuburculosis

<400> SEQUENCE: 69

```
atgacctcgc gttttatgac ggatccgcac gcgatgcggg acatggcggg ccgttttgag     60
gtgcacgccc agacggtgga ggacgaggct cgccggatgt gggcgtccgc gcaaaacatt    120
tccggcgcgg gctggagtgg catggccgag gcgacctcgc tagacaccat gacccagatg    180
aatcaggcgt ttcgcaacat cgtgaacatg ctgcacgggg tgcgtgacgg gctggttcgc    240
gacgccaaca actacgaaca gcaagagcag gcctcccagc agatcctcag cagc          294
```

<210> SEQ ID NO 70
<211> LENGTH: 282
<212> TYPE: DNA
<213> ORGANISM: Mycobacteria tuburculosis

<400> SEQUENCE: 70

```
atgaccatca actatcaatt cggggacgtc gacgctcacg gcgccatgat ccgcgctcag     60
gccgggtcgc tggaggccga gcatcaggcc atcatttctg atgtgttgac cgcgagtgac    120
ttttggggcg gcgccggttc ggcggcctgc caggggttca ttacccagct gggccgtaac    180
ttccaggtga tctacgagca ggccaacgcc cacgggcaga aggtgcaggc tgccggcaac    240
aacatggcac aaaccgacag cgccgtcggc tccagctggg cc                       282
```

<210> SEQ ID NO 71
<211> LENGTH: 1185
<212> TYPE: DNA
<213> ORGANISM: Mycobacteria tuburculosis

<400> SEQUENCE: 71

```
atgaaggcac cgttgcgttt tggcgttttc atcacgccat tccatccgac cggtcaatcc     60
```

-continued

```
ccgaccgtgg cgttgcaata cgacatggag cgcgtcgttg cgctggaccg gctcggctac      120
gacgaggcgt ggtttggcga acaccactcc ggtggctacg agctgatcgc ttgcccggag      180
gtgtttatcg cggccgcagc ggaacggacc acccacatcc ggctaggtac cggagtggtt      240
tcgctgccct accatcatcc gctaatggtg gccgaccgtt gggtgctgct ggatcacctg      300
acccgtgggc gggtcatgtt cggcaccggc cccgcgcgc tgccgtcgga cgcctacatg      360
atgggcatcg atccggtcga gcagcgacga atgatgcagg agtccctcga ggcgattctc      420
gcgctgttcc gtgccgcacc tgacgagcga atcgaccgcc actccgactg gttcaccctg      480
cgtgaagcgc aattgcacat ccgcccctac acctggccgt accccgaaat cgctaccgca      540
gccatgattt cgccatcggg tccgcgactg ccggtgcgc tgggcacgtc gctgttatca      600
ctgtcgatgt cagtgcccgg cggctacgct gcgctggaaa cagcgtgggg cgtggtgcgg      660
gagcaggccg ccaaagctgg gcggggcgag ccggatcgcg ccgattggcg ggtgttgagc      720
atcatgcact tgtcggacag ccgcgaccag gcgatcgacg actgcactta cgggttaccc      780
gacttctcga ggtacttcgg cgcggcaggg tttgtcccgt tggcgaacac cgtggaaggc      840
acccagtcgt ctcgggaatt cgtcgagcaa tacgcggcca agggaaattg ctgcatcggc      900
acgcccgatg acgcgatcgc ccacattgaa gacttgctgc accggtcggg tggcttcgga      960
acgttgctac tgctcggcca cgactgggcc ccgccaccgg caacctttca ctcctatgag     1020
ctgttcgccc gtgctgtgat tccttatttc aagggacaac tcgcggcgcc gcgggcgtcg     1080
cacgaatggg ctagaggcaa gcgcgaccaa ttgattggcc gcgccggcga agcggtcgtc     1140
aaagccatca ccgagcacgt cgccgaacaa ggggaagcgg gcagc                    1185
```

<210> SEQ ID NO 72
<211> LENGTH: 966
<212> TYPE: DNA
<213> ORGANISM: M. tuberculosis

<400> SEQUENCE: 72

```
atgggcgcac ctaccgaacg gttagttgat accaacggcg tgcgactgcg agtggtcgag       60
gccggtgagc ccggcgcacc cgtggtgata ctggcccacg gctttcccga actggcctat      120
tcatggagac accagattcc tgcgcttgcc gacgccggct accacgtgtt ggctcccgat      180
cagcgcggtt acgcgggatc gtctcgccca gaggcgatcg aggcctacga cattcaccgg      240
ttgaccgctg acctagtggg cctactagat gatgtcggtg ccgagcgggc ggtctgggtt      300
ggtcatgact ggggtgccgt ggtggtgtgg aacgcgccac tgctgcacgc tgaccgagtc      360 gccgcgttg ccgcgttgag cgtccccgcg ctgccccggg cacaggtgcc gccgacgcaa      420
gcgttccgca gcaggtttgg ggagaacttc ttctacatcc tttatttcca ggagcccggc      480
atcgccgacg ccgaactcaa tggcgacccg gcccgcacga tgcgccgaat gatcggcggt      540
ctgcgccctc cgggcgatca gagcgcggca atgcgtatgc tggcgccggg ccccgacggc      600
tttatcgatc ggcttccgga gccggccggg ttgccggcct ggattagtca ggaggaactc      660
gaccactaca tcggcgagtt cacccgcacc ggtttcaccg gcggcctgaa ctggtaccgc      720
aacttcgacc gcaactggga gaccacgacc gacctcgccg gcaagacgat ctccgtgccc      780
tcgttgttca ttgcgggcac agccgatccc gtcttgacgt tcacccgcac cgaccgcgct      840
gcggaggtga tctccggccc gtatcgcgag gtgctgatcg acgggccgg tcactggctg      900 cagcaggaac gtcccggtga ggtgaccgcg gccctgctgg agttcctgac ggggttggag      960
```

```
ttgcga                                                                 966

<210> SEQ ID NO 73
<211> LENGTH: 1365
<212> TYPE: DNA
<213> ORGANISM: Mycobacteria tuburculosis

<400> SEQUENCE: 73
gtgaataccg atgtgctggc tggcctgatg gccgagctgc ccgaggggat ggtggtcacc         60
gaccccgccg tcaccgacgg ctaccggcaa gaccgggcct ttgacccttc ggccggcaaa        120
ccgctggcaa tcatccggcc acggcgcacc gaagaggtgc agacggtgct gcgttgggcc        180
agtgcgaacc aggtgcccgt ggtgacccga ggagccggta gcggcctttc gggcggggcg        240
accgccctgg atggcgggat cgtgctgtcc accgaaaaga tgcgcgacat caccgtcgac        300
ccggtcaccc gcaccgcagt gtgccagccc ggcctgtaca acgccgaggt gaaggaggcc        360
gccgccgaac acggcctgtg gtatcccccg gatccgtcgt cgttcgagat ctgcagcatc        420
ggcggcaaca tcgccaccaa cgccggcggg ctgtgctgcg tgaagtacgg cgtcacaggc        480
gactacgtac tgggcatgca ggttgtgctg gccaacggca ccgcggtccg gctgggcggc        540
ccacggctca aggacgtcgc cgggcttttc ctgaccaaac tgttcgtcgg cagcgaaggc        600
acgctgggcg tcatcacgga ggtgacgttg cgactgctgc ccgcacagaa tgcatcgagc        660
atcgtggtgg ccagcttcgg ctcggtgcag gcggcggtcg atgcggtgct cggggttacc        720
ggccgacttc gccccgcgat gctggagttc atggattcgg tggcgatcaa cgccgtcgag        780
gacaccttgc ggatggacct ggaccgcgat gcggcggcca tgctggtggc tggttctgat        840
gaacgtggcc gcgcggccac cgaagacgcc gccgtgatgg ccgccgtgtt cgccgaaaac        900
ggtgcgatag acgtgttttc gaccgacgac ccggatgagg gcgaggcgtt cattgcggcc        960
cggcggttcg ccattccggc ggtcgagagc aaggggcgt tgctgctcga ggacgtcggg       1020
gtaccgctgc ccgcactggg cgaactggtc accgggattg cgcgcatcgc cgaggagcgg       1080
aatctgatga tctcggtgat cgcccacgcc ggggacggca ataccaccc gttgctggtg       1140 tacgaccccg cagatgccgc gatgctagag cgcgcccacc tcgcgtacgg cgaaatcatg       1200
gacctggccg tcgcctgggc cggcacgatc accggcgaac acggcgtggg ccggttgaaa       1260
cggccgtggt tggccggcta tctcgggccc gacgtcctgg ccctcaacca gcgcatcaag       1320
caagcgctgg accccaggg catcctcaat cccggctcgg cgatc                        1365

<210> SEQ ID NO 74
<211> LENGTH: 1215
<212> TYPE: DNA
<213> ORGANISM: Mycobacteria tuburculosis

<400> SEQUENCE: 74
atgacatcag taatgtctca cgaattccag ctcgccaccg ccgaaacctg gccgaatccg         60
tggccgatgt accgcgcgtt gcgcgaccac gacccggtgc accacgtcgt cccgccgcag        120
cgtcccgagt acgactacta cgtgctgtcc cggcacgccg acgtctggtc ggcagcgcgg        180
gaccatcaga cgttctcgtc ggcgcaaggc ttgaccgtta actacggcga gctgaaatg         240 attggactgc acgacacccc gcccatggtg atgcaggatc cgccggtcca caccgagttt        300
cgcaagctgg tgtcgcgcgg cttcacgcca cgacaggtcg aaaccgtcga gcccacggtg        360
cgcaagttcg tcgttgagcg gctcgaaaag ctgcgcgcca acggtggcgg cgacattgtc        420
accgaactat tcaaaccgct cccgtcgatg gtggtggcgc actatctcgg tgttcccgaa        480
```

```
gaggattgga cgcaattcga cgggtggacc caggccatcg tggcggcgaa cgcggttgac      540
ggcgccacca ccggcgcact ggacgcggtc ggctcgatga tggcctactt caccgggctg      600
atcgagcgac gccgcaccga gcccgccgac gacgccatct cccacctggt agccgccggg      660
gtcggcgccg acggcgacac cgccggcaca ctgtccatac tggcgttcac gttcaccatg      720
gtcaccggcg gcaacgacac cgtcaccggc atgctaggcg gttcgatgcc gttgctgcac      780
cggcggcccg accagcgccg gctgctgctg gatgacccag agggcatccc cgacgcggtc      840
gaggagctgc tgcggctcac ctcgccggtg caggggctgg cgcgcacaac cacgcgcgac      900
gtcacgatcg gtgacaccac catcccggcc ggtcgccggg tgctgctgct gtacggctcg      960
gccaaccgtg acgaacgcca atacggcccg gacgcagccg aactcgatgt cactcggtgc      1020
ccgcgcaaca tcttgacctt cagccacggc gcccaccact gcctgggtgc ggccgcggcc      1080
cggatgcaat gccgggtggc gctgaccgaa ctgctggccc ggtgcccgga cttcgaggtg      1140
gccgagtcac gcatcgtgtg gtccggcggc agttatgtcc ggcgtccgct gtcggtgccg      1200
ttccgagtga catcc                                                      1215

<210> SEQ ID NO 75
<211> LENGTH: 606
<212> TYPE: DNA
<213> ORGANISM: Mycobacteria tuburculosis

<400> SEQUENCE: 75
atggcgggta ccgactggct gtccgcgcgt cggaccgagt tagccgcaga tcggatactc       60
gacgccgccg agcgactctt tacgcagcgt gacccggcgt cgatcggcat gaacgagatc      120
gccaaggccg caggctgttc gcgcgcaaca ctgtatcggt acttcgacag ccgcgaggcg      180
ctgcgaaccg cgtacgtgca ccgcgagacc cgccggctcg gccgcgagat catggtgaag      240
atcgccgatg tcgtcgaacc tgccgaacgg ctgctggtga gcatcaccac gacgttgcgg      300
atggtccgcg acaaccccgc gttggccgcg tggtttacca ccacccgccc accgatcggc      360
ggcgagatgg ccggacggtc cgaggtgatc gcggccctgg ccgcggcatt cctcaactca      420
ctaggtcccg acgatccgac caccgtcgaa cgccgcgccc gctgggtggt ccggatgctc      480
acatcgctgc tgatgttccc cggccgtgac gaagccgacg aacgagcgat gatcgcggag      540
ttcgtcgtcc cgatcgtgac acctgcttct gccgccgcta ggaaggccgg tcaccctgga      600
cccgag                                                                606

<210> SEQ ID NO 76
<211> LENGTH: 534
<212> TYPE: DNA
<213> ORGANISM: Mycobacteria tuburculosis

<400> SEQUENCE: 76
atgcatccaa tgataccagc ggagtatatc tccaacataa tatatgaagg tccgggtgct       60
gactcattgt ctgccgccgc cgagcaattg cgactaatgt ataactcagc taacatgacg      120
gctaagtcgc tcaccgacag gctcggcgag ctgcaggaga actggaaagg tagttcgtcg      180
gacttgatgg ccgacgcggc tggcggtat ctcgactggc tgactaaaca ctctcgtcaa      240
attctggaaa ccgcctacgt gatcgacttc ctcgcatacg tctatgagga gacacgtcac      300
aaggtggtac ccccggcgac tatcgccaac aaccgcgagg aggtgcacag gctgatcgcg      360
agcaacgtgg ccggggtaaa cactccagca atcgcaggac tcgatgcaca atatcagcag      420
```

-continued taccgggccc aaaatatcgc tgtcatgaac gactatcaaa gtaccgcccg gtttatccta 480
gcgtatctgc cccgatggca ggagccgccg cagatctacg ggggcggggg cggg 534

<210> SEQ ID NO 77
<211> LENGTH: 1230
<212> TYPE: DNA
<213> ORGANISM: Mycobacteria tuburculosis

<400> SEQUENCE: 77
gtggccacga tagcccaacg gctgcgtgac gaccacgggg tggcggcgtc ggagtcgtcg 60
gtgaggcgtt ggatcgcaac gcatttcgcc gaggaggtgg cccgcgagag agtcacggtg 120
ccgcgcggac cggtcgatgc gggtagtgag gcgcagatcg attacgggcg gctgggcatg 180
tggttcgacc cggccaccgc gcgccgggtc gcggtgtggg cgttcgtgat ggtgctggcg 240
ttctcccgac acctgttcgt gcgtccggtc atccggatgg accaaaccgc ttggtgtgct 300
tgccatgtcg ccgcattcga attcttcgac ggggtgccgg cgcggctagt gtgtgacaac 360
ctcaggaccg gggtggacaa gcccgacctg tacgacccgc agatcaaccg ctcctacgcc 420
gagctggcca gccactacgc cacgctggtc gacccggccc gcgccagaaa acccaaagat 480
aaaccccgcg tggagcggcc gatgacctat gtgcgggact cgttttggaa aggccgcgag 540
ttcgattcgc tggcccagat gcagcaggcg gcggtcacct ggagcaccga agtggccggg 600
cttcggtact tacgtgcctt ggagggcgcc caacccctgc ggatgttcga agctgtggag 660
caacaagcgt tgatcgcatt gccgcccagg gcatttgaac tcaccagctg gtcgatcggc 720
accgtcgggg tggacacgca cctcaaagtt ggcaaggcac tctattccgt gccgtggcgg 780
ctgatcgggc aacgcctgca cgcgcgcacc gccggtgatg tggtgcagat cttcgccggc 840
aacgatgtgg tggccaccca tgtgcgccga cccagcgggc gctccaccga cttctcccac 900
tacccaccgg agaagatcgc cttccacatg cgcaccccga cctggtgtcg acacaccgcc 960
gaactggtcg gcccagccag ccagcaagtg atcgccgaat tcatgcgcga caacgccatc 1020
caccacctac ggtcggccca aggcgtgctc gggctacgcg acaaacacgg ctgcgaccgg 1080
ctggaggccg cctgcgcccg cgccatcgag gtcggcgacc cgagctatcg caccatcaag 1140
ggcatccttg ttgccggcac cgaacacgcc gccaacgagc cgaccaccag tagtccggca 1200
agcaccgctg gggcgttcc tgcgcggccc 1230

<210> SEQ ID NO 78
<211> LENGTH: 753
<212> TYPE: DNA
<213> ORGANISM: Mycobacteria tuberulosis

<400> SEQUENCE: 78
atgtctatct gtgatccggc gctgcgtaat gcgctacgta ccctgaaact gtccggcatg 60
ctcgacaccc tcgacgcccg cctggcccaa acccgcaacg gcgacctggg gcatctggaa 120
ttcctgcaag cgttgcgtga agacgagatc gcccgccgcg agtccgccgc cctgacacga 180
cgattacgcc gcgccaagtt cgaagcccaa gccaccttcg aagacttcga cttcactgcc 240
aacccgaaac tgcccggtgc gatgttgcgc gatctggccg cgctgcgctg gctggatgcc 300
ggcgaatcgg tcatcctcca cggcccggtc ggcgtcggaa aaacccatgt agcacaagca 360
cttgtccacg ccgtggcccg ccgcggcggc gacgtgcgct tcgccaaaac ctcccgcatg 420
ctctccgacc tcgccggcgg gcacgccgac cgatcctggg gccaacgcat ccgcgaatac 480
accaagccgc tcgtgctcat tctggacgac ttcgcgatgc gtgagcacac cgccatgcac 540

```
gctgatgacc tctacgagct catcagcgac cgcgccatca ctggcaaacc gctgatcttg     600
accagcaacc gcgcaccgaa taactggtac ggcctgttcc ccaacccgt cgtcgccgaa      660 tcactcctgg atcggctcat caacaccagc caccaaatcc tcatggacgg acccagctac    720
cgaccccgca agagacccgg ccgcaccacc agc                                  753
```

<210> SEQ ID NO 79
<211> LENGTH: 696
<212> TYPE: DNA
<213> ORGANISM: Mycobacteria tuberulosis

<400> SEQUENCE: 79

```
atgcatctaa tgatacccgc ggagtatatc tccaacgtaa tatatgaagg tccgcgtgct      60
gactcattgt atgccgccga ccagcgattg cgacaattag ctgactcagt tagaacgact    120
gccgagtcgc tcaacaccac gctcgacgag ctgcacgaga actggaaagg tagttcatcg    180
gaatggatgg ccgacgcggc tttgcggtat ctcgactggc tgtctaaaca ctcccgtcag    240
attttgcgaa ccgcccgcgt gatcgaatcc ctcgtaatgg cctatgagga gacacttctg    300
agggtggtac ccccggcgac tatcgccaac aaccgcgagg aggtgcgcag gctgatcgcg    360
agcaacgtgg ccgggggtaa acactccagc aatcgcagac ctcgaggcac aatacgagca    420
gtaccgggcc gaaaatatcc aagcaatgga ccgctatcta agttggaccc gatttgcgct    480
atcgaagctg ccccgatggc gggagccgcc gcagatccac aggagcgggt aggtccaaga    540
ggccggcgcg gtcttgcagg ccagcaacaa tgccgcggtc gaccaggccc atcgcttcgc    600
tgctcgcacg acacaccgcg gtttcagatg aatcaggcgt ttcacaccat ggtgaacatg    660
ttgctgacgt gttttgcatg tcaggagaaa ccgaga                              696
```

<210> SEQ ID NO 80
<211> LENGTH: 528
<212> TYPE: DNA
<213> ORGANISM: Mycobacteria tuberulosis

<400> SEQUENCE: 80

```
atgcatccaa tgataccagc ggagtatatc tccaacataa tatatgaagg cccgggcgct      60
gactcattgt ttttcgcctc cgggcaattg cgagaattgg cttactcagt tgaaacgacg    120
gctgagtcgc tcgaggacga gctcgacgag ctggatgaga actggaaagg tagttcgtcg    180
gacttgttgg ccgacgcgt tgagcggtat ctccaatggc tgtctaaaca ctccagtcag    240
cttaagcatg ccgcctgggt gatcaacggc ctcgcgaacg cctataacga cacacgtcgg    300
aaggtggtac ccccggagga gatcgccgcc aaccgcgagg agaggcgcag gctgatcgcg    360
agcaacgtgg ccgggtaaa cactccagca atcgcagacc tcgatgcaca atacgaccag    420
taccgggccc gcaatgtcgc tgtaatgaac gcctatgtaa gttggacccg atctgcgcta    480
tcggatctgc cccggtggcg ggaaccgccg cagatctaca ggggcggg                 528
```

<210> SEQ ID NO 81
<211> LENGTH: 1170
<212> TYPE: DNA
<213> ORGANISM: M. tuberculosis

<400> SEQUENCE: 81

```
atgatcatcg ttgtcgggat cggcgccgac ggcatgaccg tctctccga gcattctcgc      60 tccgaattgc gcagggccac agtaatttac ggctcgaaac ggcaacttgc cctgctcgac    120
```

-continued

| | |
|---|---|
| gataccgtca ccgccgagcg ctgggagtgg ccgacgccga tgctgcccgc ggtgcaaggc | 180 |
| ctgtcaccgg atgggctga cctacacgtg gttgccagcg gcgacccgtt gttgcatggt | 240 |
| atcggctcca ccctgatccg gctgttcggc cacgacaacg tgaccgtgtt gccgcacgtg | 300 |
| tccgcggtga cgttggcgtg cgcccggatg ggctggaacg tgtatgacac cgaggtgatc | 360 |
| agcctggtca ccgcgcaacc acacaccgcg gtgcgccgcg cgggccgggc catcgtgctg | 420 |
| tccggcgatc ggtccacccc gcaggcgctg gcggtgctgc tgaccgagca cggtcgcggt | 480 |
| gactccaagt tcagcgtgct cgaacagctt ggcggcccgg ccgaacgccg ccgcgacggt | 540 |
| acggcccggg catgggcctg cgacccaccc ctcgatgtcg atgagctcaa cgtgatcgcc | 600 |
| gtgcgctacc tgctcgacga gcgcacgtcg tgggcacccg acgaggcatt cgcgcacgac | 660 |
| gggcagatca ccaaacaccc gatccgcgtg ctgaccctgg ctgcgctggc gccaaggccc | 720 |
| gggcagcggt tatgggacgt cggcgcgggc tcaggcgcca tcgcggtcca gtggtgtcgg | 780 |
| agctggccgg gctgcaccgc ggtggcgttc gagcgcgacg aacggcgccg ccgcaacatt | 840 |
| gggttcaatg ccgcggcctt cggggtgagc gtcgacgtgc gcggcgacgc gcccgatgcg | 900 |
| ttcgacgacg ccgcacggcc gtcggtgatt tttcttggcg gtggtgtaac ccagccaggc | 960 |
| ctgcttgagg cctgcctgga cagcctgccc gcaggcggga acttggtcgc caacgctgtc | 1020 |
| accgtcgaat cggaagccgc tctggcgcat gcatattcgc gcctcggtgg cgagctacga | 1080 |
| cgattccagc actatctcgg cgaaccgctg ggcggcttca ccggttggcg cccacagctg | 1140 |
| ccggtcaccc agtggtcggt gaccaagcga | 1170 |

<210> SEQ ID NO 82
<211> LENGTH: 747
<212> TYPE: DNA
<213> ORGANISM: Mycobacteria tuberulosis

<400> SEQUENCE: 82

| | |
|---|---|
| gtggacgaca cgggcgctgc tccggtagta attttcggcg gccgcagcca gatcggcggc | 60 |
| gaactcgcgc gacgcctggc tgccggggcg acgatggtgc tggccgcgcg gaacgccgat | 120 |
| caactcgccg accaggccgc cgcactccgc gcagctggcg ctatagcggt gcacacccgg | 180 |
| gagttcgacg ccgacgacct ggccgcacac ggcccgttgg tcgcttcgct cgttgccgag | 240 |
| cacggcccca tcggcaccgc ggtgctggcc ttcgggatac tcggcgacca ggcccgcgcc | 300 |
| gagacagacg cggcgcacgc ggtggccatc gtgcacaccg actacgtcgc ccaggtcagc | 360 |
| ctgctgactc atctggcagc ggcgatgcgc accgccggac ggggatcgct ggtggtgttc | 420 |
| tcctcggtcg ccgggattcg ggtgcgccgc gccaactatg tctacggatc ggccaaagcc | 480 |
| ggcctggacg gcttcgccag cggcctggcc gatgcgttgc acggcaccgg ggtgcggtta | 540 |
| ctgatcgcgc ggccgggatt cgtcatcggg cgcatgaccg agggcatgac gcccgcaccc | 600 |
| ctgtcggtca ccccggagcg ggtggccgcc gcgaccgcgc gtgcgctggt caacggtaag | 660 |
| cgcgtggtgt ggattccgtg ggcgctgcgg ccaatgtttg ttgcgctgcg gttgcttccc | 720 |
| cggttcgtct ggcgcaggat gccgcga | 747 |

<210> SEQ ID NO 83
<211> LENGTH: 411
<212> TYPE: DNA
<213> ORGANISM: Mycobacteria tuberulosis

<400> SEQUENCE: 83

| | |
|---|---|
| gtggcgatgg tcaacaccac tacgcggctt agtgacgacg cgctggcgtt tctttccgaa | 60 |

-continued

```
cgccatctgg ccatgctgac cacgctgcgg gcggacaact cgccgcacgt ggtggcggta    120
ggtttcacct tcgaccccaa gactcacatc gcgcgggtca tcaccaccgg cggctcccaa    180
aaggccgtca atgccgaccg cagtgggctt gccgtgctca gccaggtcga cggcgcgcgc    240
tggctctcac tggagggtag ggcggcggtg aacagcgaca tcgacgccgt gcgcgacgcc    300
gagctgcgct acgcgcagcg ctatcgcacc ccgcgtccca atccacgccg agtggtcatc    360
gaggtccaga ttgagcgcgt gctgggatcc gcggatctgc tcgaccgggc c             411
```

<210> SEQ ID NO 84
<211> LENGTH: 1461
<212> TYPE: DNA
<213> ORGANISM: Mycobacteria tuberulosis

<400> SEQUENCE: 84

```
atgccccgcg cccgatggct gcagagcgcg gccctcatgg gcgccttggc cgtggtgttg     60
ataaccgcgg caccggtggc cgccgatgcc taccaggtgc ccgctccgcc ctcgcccacc    120
gcatcctgtg acgtaataag cccggttgcg atcccctgcg tggcgctcgg caagttcgcc    180
gacgcggtcg ctgcggagtg tcgccgcgtc ggtgtgcccg atgcgcggtg cgtgcttccg    240
ctcgcgcacc gggtgaccca ggccgcgcgt gatgcctacc tacagtcttg ggtgcatcgc    300
accgcgcggt tccaggatgc gttgcaagac ccggtgccgc tgcgggaaac tcagtggctc    360
ggcacgcaca actcgttcaa cagcctcagc gattcgttca cggtctcgca cgcagactca    420
aaccagcagc tgtcgttggc ccaacagctc gacatcgacg tccgcgcgct cgagctagac    480
ctgcactact tgccccgcct cgagggccac ggcgcccccg gcgtcaccgt gtgtcacggg    540
ctgggaccga agaacgcgaa cctaggctgc accgtcgaac ctctgctggc cacagtgctg    600
ccgcagatcg ccaactggtt gaacgcaccc gggcataccg aggaggtcat cctgctctac    660
ctggaggacc agctgaagaa cgcgtcggcg tatgagtcgg tggtggctac cctcgaccaa    720
gtgttgcggc gtgcggacgg aacaagcctt atctaccgtc ccaacccggc ccggcgtgcc    780
accaacggct gtgtcccgct tccactcgac gtgtcgcggg aggaaatccg cgcatccggc    840
gcacgagccg tgctcgtcgg gtcttgtgcg ccaggttggt cggccgccgt cttcgactgg    900
agcggcgttg agctggaaag cggctcgaac tccggctacc ggccataccc ggcctgcgat    960
gccacctatg gccgcggtgt ctacgcttgg cgactggtcc gctattacga ggactccacg   1020
ctggccacgg cgttggccaa cccgacccgt ccaccggcca atccgcaggc gcttaccccg   1080
ccgaaggtgc cggcgatgac cgattgcggg gtcaatctgt tcggcttcga tcagctgctc   1140
cccgaagacg gccgcattca ggcgtcgttg tggagctggg caccggacga accgcgtgcc   1200
ggtgccggag catgcgccct gcagggcgcg gatggccgct gggtcgccgc atcgtgcggt   1260
gacccacacc ctgcggcctg tcgggacgcg gcaggcaggt ggaccgtgac gccggcaccc   1320
gtggtcttcg ccggggctgc cctagcctgc acagccatcg gcgcggactt taccctgccc   1380
cgaacgggca atcagaacgc ccgtctgcac gccgtggccg ggcccgccgg tggcgcctgg   1440
gtgcattacc tactgccgcc a                                             1461
```

<210> SEQ ID NO 85
<211> LENGTH: 429
<212> TYPE: DNA
<213> ORGANISM: Mycobacteria tuberulosis

<400> SEQUENCE: 85

-continued

```
atgaccacca cgccccgaca accccctgttc tgcgcccacg ccgacaccaa cggcgacccg      60
ggccgctgcg cctgcggcca gcagctcgcc gacgtcggcc cggccacccc gccaccgccc     120
tggtgcgaac cgggcaccga acccatctgg gagcagctca ccgaacgata cggcggcgtc     180
acaatctgcc agtggacacg atattttccg gccggcgacc cggtggctgc cgacgtgtgg     240
atcgccgccg acgatcgtgt cgttgacggc cgggtgctgc gcacccaacc ggcgattcac     300
tacacggaac cgcccgtgtt ggggatcggc ccggcggcgg cccgccggct ggccgctgag     360
ctgctcaacg ccgccgacac cctcgacgac ggccgccggc agctagacga cctcggcgaa     420
caccggcgg                                                             429
```

<210> SEQ ID NO 86
<211> LENGTH: 996
<212> TYPE: DNA
<213> ORGANISM: Mycobacteria tuberulosis

<400> SEQUENCE: 86

```
gtgaacaccg cgacccgggt ccggctggcc cgcaaacgcg ccgaccggct caatctgaaa      60
ctaatcaaga acggccacca cttcaggttg cgtgacgccg acgagatcac gctggcggtc     120
gggcacctag gggtggtgga agccttcctg gcggcggcca agtcgcaaaa caagccgccc     180
ggtccgccgc cgagcctcca cgccccgcca tcctggcggc gcgacatcga cgactacctg     240
ctcaacctga acgccgccgg tcaacgccca gcgacgatcc ggctacgcaa gacggtgctg     300
tgcgcagccg cccacggcct cggccgccca cccgccgacg tcaccgccga acacctcctg     360
gactggctag gcaaacagca gcacctctcc ccagagggcc gcaaaaccta tcgcagcacg     420
ttgcggggct tcttcgtgtg ggcctacgaa atggaccggg tgcgcgacta tgtcgcagac     480
tccctgccta aggtgcgctg cccgaaacag ccgccccgcc cggccggcga cgacgtctgg     540
caagcggcgc tggccaaggc cgaccgtcga atcgagctga tgatccgcct agccggtgag     600
gccgggctgc gacgcgccga agccgcccag gcgcacaccg gcgacttgat ggacggcggg     660
cttctcctcg ttcacggcaa aggtggtaaa cgccgtattg tgccgatcag cgactacttg     720
gccgcgctca tccgcgacac cccgcacggc tacctgttcc ccaacggcac cggcggccac     780
ctcaccgccg aacacgtggg aaaactcgtc tcccgggcat tacccggtga cgcgaccatg     840
cacaccctgc ggcaccgata cgccacccgc gcctaccgcg gctcccacaa cttgcgagct     900
gtacaacaac ttctcggtca cgcctcgatc gtgacaacag aacgctacac agcgctgtgc     960
gacgacgagg tgcgcgccgc agcagcagcc gcatgg                                996
```

<210> SEQ ID NO 87
<211> LENGTH: 366
<212> TYPE: DNA
<213> ORGANISM: Mycobacteria tuberulosis

<400> SEQUENCE: 87

```
gtgcacgtgt gccacacgat cgccgacgtg gtcgaccggg ccaaagccga acgctccgaa      60
aacacgcttc gcaaggattt cacccccctcg gagctgctcg ccgctggtcg ccggatcgcc    120
gagctggaac ggccgaaagc caaacagcgg caacgcgaag gcggcgacca tggccgccag     180
gctcgatatt ctggcttagg ctccatggag cctaagccag aatcagagcg cgatgcccac     240
aaagccgaca ctgccatcag cgaagccctc ggcatctccc gcggccacta ccagcggctc     300
aaacgaatcg acaacgcaac ccgcagcgaa gctggctacc gggatggttt aaacggttgg     360
agcggc                                                                366
```

<210> SEQ ID NO 88
<211> LENGTH: 324
<212> TYPE: DNA
<213> ORGANISM: Mycobacteria tuberulosis

<400> SEQUENCE: 88
atgtcaggtg gttcatcgag gaggtacccg ccggagctgc gtgagcgggc ggtgcggatg 60
gtcgcagaga tccgcggtca gcacgattcg gagtgggcag cgatcagtga ggtcgcccgt 120
ctacttggtg ttggctgcgc ggagacggtg cgtaagtggg tgcgccaggc gcaggtcgat 180
gccggcgcac ggcccgggac cacgaccgaa gaatccgctg agctgaagcg cttgcggcgg 240
gacaacgccg aattgcgaag ggcgaacgcg attttaaaga ccgcgtcggc tttcttcgcg 300
gccgagctcg accggccagc acgc 324

<210> SEQ ID NO 89
<211> LENGTH: 984
<212> TYPE: DNA
<213> ORGANISM: Mycobacteria tuberulosis

<400> SEQUENCE: 89
aaagaccgcg tcggctttct tcgcggccga gctcgaccgg ccagcacgct aattacccgg 60
ttcatcgccg atcatcaggg ccaccgcgag ggccccgatg gtttgcggtg gggtgtcgag 120
tcgatctgca cacagctgac cgagctgggt gtgccgatcg ccccatcgac ctactacgac 180
cacatcaacc gggagcccag ccgccgcgag ctgcgcgatg gcgaactcaa ggagcacatc 240
agccgcgtcc acgccgccaa ctacggtgtt tacggtgccc gcaaagtgtg gctaaccctg 300
aaccgtgagg gcatcgaggt ggccagatgc accgtcgaac ggctgatgac caaactcggc 360
ctgtccggga ccacccgcgg caaagcccgc aggaccacga tcgctgatcc ggccacagcc 420
cgtcccgccg atctcgtcca gcgccgcttc ggaccaccag cacctaaccg gctgtgggta 480
gcagacctca cctatgtgtc gacctgggca gggttcgcct acgtggcctt tgtcaccgac 540
gcctacgctc gcaggatcct gggctggcgg gtcgcttcca cgatggccac ctccatggtc 600
ctcgacgcga tcgagcaagc catctggacc cgccaacaag aaggcgtact cgacctgaaa 660
gacgttatcc accatacgga taggggatct cagtacacat cgatccggtt cagcgagcgg 720
ctcgccgagg caggcatcca accgtcggtc ggagcggtcg gaagctccta tgacaatgca 780
ctagccgaga cgatcaacgg cctatacaag accgagctga tcaaacccgg caagccctgg 840
cggtccatcg aggatgtcga gttggccacc gcgcgctggg tcgactggtt caaccatcgc 900
cgcctctacc agtactgcgg cgacgtcccg ccggtcgaac tcgaggctgc ctactacgct 960
caacgccaga gaccagccgc cggc 984

<210> SEQ ID NO 90
<211> LENGTH: 1437
<212> TYPE: DNA
<213> ORGANISM: Mycobacteria tuberulosis

<400> SEQUENCE: 90
atgactaatg aacaacattt cgctgacgat ggcgacatca aacagctcag cctcgacgaa 60
acccgttccg cggcaaaaca gctcctcgac tccgtcgagg gcgacctgac cggtgatgtg 120
gcgcaacgtt ttcaggcgct gacacgccac gccgaggaac tgcgggcgga gcagcgccgc 180
cgcggccgcg aagccgagga ggcgctgcgc cgctgccggg ccggtgagct gagggtggtg 240

-continued

```
cccggtgctc ccaccggcgg cgacgacggc gacgcgccgc cgggcaactc gttgcgcgac      300
atcgcgtttc gcacactgga cgtttgtgtg cgcgatggcc tgatgtcgtc gcgggcggcg      360
gaagccgcgg aaaccttgtg ccgcaccggg ccgccgcagt cgacgtcgtg ggcgcagcgc      420
tggctggcgg ccaccggcaa ccgcgactac ctgggggcgt tcgtcaagag ggtttcgaac      480
cctgttgcgg ggcacacgac ctggaccgac cgggaagcgg ccgcgtggcg tgaggcggcc      540
gcggtggccg ccgagcagcg agcaatgggc ttggtggaca ccgccggcgg gttttttgatc     600 ccggcggcgc tggatccggc gattctgctg tcgggtgatg gttcaacgaa tccgatccgg      660
caggtggcga gggtggtgca aacgacctcc gaggtttggc ggggcgtgac ctccgaaggc      720
gccgaggctc attggtactc cgaagcccag gaggtgtccg acgattcgcc aacgctggcc      780
cagccggcgg tgccgagcta ccgtggctcc tgctggattc cgttcagtct cgagattgag      840
ggtgacgccg ccggattcgt cgcagaggtg ggccgcgtcc tagcggattc ggttgagcag      900
ctgcaggcgg cggcgttcgt cagcggctcc ggcaacggcg agcccaccgg attcgtctcc      960
gcactgaccg gcaccgcgga ctacaccgtc accggcgcgg ggacggaagc cgttgtagcc     1020
gccgacgttt acgcgctgca gtcggcgttg ccgccgcgct ttcaatccaa cagcgcgttc     1080
gcggcgaact tgtccaccat caacgtgctg cgccaggcgg aaaccgcgaa tggggcgctg     1140
aaattcccat cgctgcacgc cagcccgccg atgctggccg ggaaacacat ctgggaggtg     1200
tcgaacatgg acaccgtgga cgcggcggtg accgccacca attacccgct ggtgcttggc     1260
gactggaagc agttcatcat caccgaccgg gtcgggtcga cggtggagct ggtgccgcac     1320
gtgttcggcg gcaaccgccg accgaccgga cagcgcggat tcttctgctg gttccgagtc     1380
ggttctgatg tgctggtgga caatgcgttc cgcgtgctga aggtgcagac caccgcg        1437
```

<210> SEQ ID NO 91
<211> LENGTH: 531
<212> TYPE: DNA
<213> ORGANISM: Mycobacteria tuberulosis

<400> SEQUENCE: 91

```
ttgagtagca tccttttccg cacggccgag ctgcggcctg gtgagggccg caccgtgtac       60
ggcgtcatcg tgccttatgg cgaggtgacc accgtccgcg acctcgacgg cgagttccgg      120
gaaatgttcg ctcctggcgc ttttcggcgc tccatcgctg agcgcggcca caaggtgaag      180
ctgctggtct cccacgacgc tcgaacccgc taccggttg gcgggccgt cgagctgcgt        240 gaggagcctc acggcttgtt cggggcgttc gagcttgcga acacccggga cggcgacgag      300
gccctggcga atgtgaaagc tggtgtggtg gacgcgtttt cggtgggttt ccggccgatc      360
cgggaccgcc gggaagggga tgtgatcgtg cgggtcgagg cggcgctgtt ggaggtctcc      420
ttgaccggcg ttccggccta tctgggcgcg cagatcgccg gtgtgcgcgc ggaatcgctt      480
gcagtcgttt cccgttcgct agccgaagcc aggttagccc tgatggattg g              531
```

<210> SEQ ID NO 92
<211> LENGTH: 624
<212> TYPE: DNA
<213> ORGANISM: Mycobacteria tuberculosis

<400> SEQUENCE: 92

```
ttgccatcgc cagcaaccgc ccgaccggac accgccacgg tgggagagcg tgtgcgcgct       60
caagttttat ggggcgtttt ttggcatcat ggcattcgcg acccgaaacc cggaaagagg      120
agggtggtgt tgaaaatggg taggcgtggt cccgcgccgg cgccggcgca gttgaaactc      180
```

```
ctcggcggcc gctcgccggg ccgtgattct ggcggccggc gggttacacc accggcggcg    240
ttcgagcgtg ttgcgccgga atgcccggat tggttgccgc caggcgctaa agacatgtgg    300
gggcgcgtcg ttcccgagct tgcggcatta aacctgctga aggagtccga ccttggggtg    360
ctgacctcct tctgcgtcgc ctgggatcag ctcatgcagg ctgtaacagc ctaccgtgaa    420
cagggtttca tcgcgacgaa cgcccgcagc cgacgggtga cggtgcatcc tgccgtggcc    480
gcggcccggg ccgcgacgag ggacgttttg gtgctcgcgc gcgaatttgg gtgcacgcca    540
agcgctgagg cgaatttggc tgctgtgctg cggcggcgcg gggaccccga cgacgacgag    600
ttcaacccgt tcgccccaga ccgg                                           624

<210> SEQ ID NO 93
<211> LENGTH: 321
<212> TYPE: DNA
<213> ORGANISM: Mycobacteria tuberculosis

<400> SEQUENCE: 93
ttgacccaca agcgcactaa acgccagcca gccatcgccg cagggctcaa cgccccgcgt     60
cggaatcgcg ttgggcggca acatggttgg ccggccgacg ttccgtccgc cgagcagcgc    120
cgcgcccaac ggcagcgcga cctcgaggct atccgccgag cgtacgccga gatggtggcg    180
acatcacacg aaatcgacga cgacacagcc gaactggcgc tgttgtcgat gcatctcgac    240
gatgagcagc gccggcttga ggcggggatg aagctcggct ggcatccgta tcacttcccc    300
gacgaacccg acagcaaaca g                                              321

<210> SEQ ID NO 94
<211> LENGTH: 243
<212> TYPE: DNA
<213> ORGANISM: Mycobacteria tuberculosis

<400> SEQUENCE: 94
atgagcggcc acgcgttggc tgctcggacg ttgctggccg ccgcggacga gcttgtcggc     60
ggcccgccag tcgaggcttc ggccgccgcg ctggccggcg acgccgcggg cgcatggcgg    120
accgcggccg tcgagcttgc gcgagcgttg gtccgcgctg tggcggagtc gcacggcgtc    180
gcggccgttt tgttcgccgc gacggccgcc gcggcggcgg ccgtcgaccg gggtgatccg    240
ccg                                                                  243

<210> SEQ ID NO 95
<211> LENGTH: 1425
<212> TYPE: DNA
<213> ORGANISM: Mycobacteria tuberculosis

<400> SEQUENCE: 95
atggctgaca tcccctacgg ccgtgactat cccgacccga tctggtgtga cgaggacggc     60
cagccgatgc cgccggtcgg cgccgaattg ctcgacgaca ttagggcatt cttgcggcgg    120
ttcgtagtct atccaagcga ccatgaactg atcgcgcaca ccctctggat tgcgcattgc    180
tggtttatgg aggcgtggga ctcaacgccc cgaatcgctt ttttgtcacc ggaacccggc    240
tctggcaaga gccgcgcact cgaagtcacg gaaccgctag tgcccggcc ggtgcatgcc    300 atcaactgca caccggccta cctgttccgt cgggtggccg atcggtcgg cggccgacc    360 gtcctgtacg acgagtgtga cacctgtttt ggcccgaaag ctaaagaaca cgaggaaatt    420
cgcggcgtga tcaacgccgg ccaccgcaag ggagccgtcg cgggccgctg cgtcatccgc    480
```

-continued ggcaagatcg ttgagaccga ggaactgcca gcgtactgtg cggtcgcctt ggccggcctc 540
gacgacctgc ccgacaccat catgtctcgg tcgatcgtgg tgaggatgcg caggagggca 600
ccaaccgaac ccgtggagcc gtggcgcccc cgcgtcaacg gccccgaggc cgagaagctg 660
cacgaccggt tggcgaactg ggcggccgcc attaacccgc tggaaagcgg ttggccggcg 720
atgccggacg gggtgaccga ccggcgcgcc gacgtctggg agtccctggt tgcggttgct 780
gacaccgcgg gcgggcactg gcccaaaacc gcccgtgcaa ccgcagaaac ggatgcaacc 840
gcaaatcgag gagccaagcc cagcataggc gtgctgctgc tgcgggatat ccgtcgagtc 900
ttcagcgacc gggaccggat gcgcaccagc gacatcctga ccggactgaa ccggatggag 960
gagggaccgt ggggctccat ccgccgcggc gacccgctcg acgcgcgcgg cctcgcgacc 1020
cggctcggca gatacggcat cgggccgaag ttccagcaca gtggtggcga accaccctac 1080
aaagggtatt cgcggaccca gttcgaggat gcgtggtccc ggtatctctc tgccgacgac 1140
gaaacccccg aggaacgaga tttatcggtt tccgcggttt ccgcggtttc accgccggtt 1200
ggcgatcccg gtgatgcaac cggcgcaacc gatgcaaccg atctcccgga ggcgggcgac 1260
ttgccgtacg agccgccggc gcccaacggg caccccaacg gcgacgcgcc gctgtgctcc 1320
gggccgggat gccccaacaa gctcctcagt actgaggcca aggccgccgg caaatgccgg 1380
ccctgccgag gtcgagcggc ggctagcgct cgggacggcg cccga 1425

<210> SEQ ID NO 96
<211> LENGTH: 390
<212> TYPE: DNA
<213> ORGANISM: Mycobacteria tuberculosis

<400> SEQUENCE: 96
atgaccgccg tcggcgggtc gccgccgacg cgacgatgcc cggccacaga ggaccgggca 60
cccgcgacag tcgccacacc gtctagcacc gatcctaccg cgtcccgcgc cgtgtcgtgg 120
tggtcggtgc acgagtatgt cgcaccgacc ctggccgccg ccgtggaatg gccgatggcc 180
ggcaccccgg cgtggtgcga cctcgacgac accgacccgg tcaaatgggc cgcgatctgc 240
gacgctgctc ggcattgggc actccgggtg gagacgtgcc aggccgcgtc ggccgaggca 300
tcacgtgacg tatccgccgc cgccgactgg ccggcggtct ctcgggagat ccagcgtcgg 360
cgtgacgcct acattcggcg ggtggtggtc 390

<210> SEQ ID NO 97
<211> LENGTH: 258
<212> TYPE: DNA
<213> ORGANISM: Mycobacteria tuberculosis

<400> SEQUENCE: 97
atgtgcgcgt tcccgtcgcc gagtctcggg tggacggtct ctcacgagac cgaaaggccc 60
ggcatggcag acgctccccc gttgtcacgg cggtacatca cgatcagtga ggccgccgaa 120
tatctagcgg tcaccgaccg cacggtccgc cagatgatcg ccgacggccg cctacgcgga 180
taccgctccg gcacccgcct cgtccgtctg cgccgcgatg aggtcgacgg cgccatgcac 240
ccgttcggtg gtgccgca 258

<210> SEQ ID NO 98
<211> LENGTH: 360
<212> TYPE: DNA
<213> ORGANISM: Mycobacteria tuberculosis

<400> SEQUENCE: 98

-continued atggccgatg cggttaagta cgtagttatg tgcaactgcg acgacgaacc gggagcgctc 60
atcatcgcct ggatcgacga cgaacgaccc gccggcgggc acatacagat gcggtcgaac 120
acccgcttca ccgaaacaca gtggggccgc catatcgagt ggaaactcga atgccgggca 180
tgccgaaagt atgcgccgat atccgagatg accgccgcgg cgatcctcga cggtttcggg 240
gcgaagcttc acgagctgag aacgtcgacc atccccgacg ctgacgatcc atcaatagca 300
gaggcgcgac acgtaattcc gttcagcgca ttatgcttgc gcttgagcca gctaggcggg 360

<210> SEQ ID NO 99
<211> LENGTH: 1125
<212> TYPE: DNA
<213> ORGANISM: Mycobacteria tuberculosis

<400> SEQUENCE: 99
gtgacgcaaa ccggcaagcg tcagagacgc aaattcggtc gcatccgaca gttcaactcc 60
ggccgctggc aagccagcta caccggcccc gacggccgcg tgtacatcgc ccccaaaacc 120
ttcaacgcca agatcgacgc cgaagcatgg ctcaccgacc gccgccgcga aatcgaccga 180
caactatggt ccccggcatc gggtcaggaa gaccgccccg gagccccatt cggtgagtac 240
gccgaaggat ggctgaagca gcgtggaatc aaggaccgca cccgcgccca ctatcgcaaa 300
ctgctggaca accacatcct ggccaccttc gctgacaccg acctacgcga catcaccccg 360
gccgccgtgc gccgctggta cgccaccacc gccgtgggca caccgaccat gcgggcacac 420
tcctacagct tgctgcgcgc aatcatgcag accgccttgg ccgacgacct gatcgactcc 480
aacccctgcc gcatctcagg cgcgtccacc gcccgccgcg tccacaagat caggcccgcc 540
accctcgacg agctggaaac catcaccaaa gccatgcccg acccctacca ggcgttcgtg 600
ctgatggcgg catggctggc catgcgctac ggcgagctga ccgaattacg ccgcaaagac 660
atcgacctgc acggcgaggt tgcgcgggtg cggcgggctg tcgttcgggt gggcgaaggc 720
ttcaaggtga cgacaccgaa aagcgatgcg ggagtgcgcg acataagtat cccgccacat 780
ctgatacccg ccatcgaaga ccaccttcac aaacacgtca accccggccg ggagtccctg 840
ctgttcccat cggtcaacga ccccaaccgt cacctagcac cctcggcgct gtaccgcatg 900
ttctacaagg cccgaaaagc cgccggccga ccagacttac gggtgcacga ccttcgacac 960
tccggcgccg tgttggctgc atccaccggc gccacactgg ccgaactgat gcagcggcta 1020
ggacacagca cagccggcgc cgcactccgc taccagcacg ccgccaaggg ccgggaccgc 1080
gaaatcgccg cactgttaag caaactggcc gagaaccagg agatg 1125

<210> SEQ ID NO 100
<211> LENGTH: 225
<212> TYPE: DNA
<213> ORGANISM: Mycobacteria tuberculosis

<400> SEQUENCE: 100
gtgatagcgg gcgtcgacca ggcgcttgca gcaacaggcc aggctagcca gcgggcggca 60
ggcgcatctg gtggggtcac cgtcggtgtc ggcgtgggca cggaacagag gaacctttcg 120
gtggttgcac cgagtcagtt cacatttagt tcacgcagcc cagattttgt ggatgaaacc 180
gcaggtcaat cgtggtgcgc gatactggga ttgaaccagt ttcac 225

<210> SEQ ID NO 101
<211> LENGTH: 186
<212> TYPE: DNA

-continued

<213> ORGANISM: Mycobacteria tuberculosis

<400> SEQUENCE: 101
atgatcgagc agggccgcga ctgccgggac gtggtcaccc agctcgccgc ggtatcgcgc 60
gcactcgacc gcgccggatt caagatcgtt gcggcagggt tgaaggaatg cgtgtccggg 120
gccacggcca gcggcgcggc accgctgagt gcagctgagc tagaaaagct gttcctggcg 180
ctcgct 186

<210> SEQ ID NO 102
<211> LENGTH: 357
<212> TYPE: DNA
<213> ORGANISM: Mycobacteria tuberculosis

<400> SEQUENCE: 102
atgtcggacc agccacgtca tcaccaggtc ctcgacgacc tgctgcccca acaccgcgct 60
ctacgtcacc agattcccca ggtgtaccag cgatttgtag ccctgggcga cgccgcgctt 120
accgacggcg ctctcagccg caaggtcaag gagcttgtgg cgctggcgat cgcggttgtg 180
caggggtgcg atggctgcgt cgcatcacac gcccaagccg cggtacgggc cggcgctaca 240
gcgcaagaag ccgctgaggc catcggggtc accatcttga tgcacggtgg accggccacc 300
atccacggtg ctcgtgccta cgcggcattt tgcgaattcg ctgacacaac gccgtcc 357

<210> SEQ ID NO 103
<211> LENGTH: 1854
<212> TYPE: DNA
<213> ORGANISM: Mycobacteria tuberculosis

<400> SEQUENCE: 103
atgtcctatc tcgtcgtggt gccggagttg gtcgcagcgg cggcaacaga tttggcgaac 60
atcggttcgt cgattagtgc agccaacgcg gccgcggcgg caccgaccac ggcactggtc 120
gcagccggcg gcgacgaggt atcggcggcc atagccgcgt tgttcggagc gcatgctcgg 180
gcatatcaag cgttgagtgc ccaggcggcg atgtttcatg aacagtttgt ccgggccctc 240
gccgccggcg gtaactccta cgccgtcgct gaggcggcaa ccgcgcaatc ggttcagcaa 300
gatctgctca acctgatcaa tgcgcccacc caggcgctgt tggggcgtcc gctgatcggc 360
aacggcgcca acgggctgcc gggtacgggc cagaacggcg gcgacggcgg gattctgtac 420
ggcaacggcg gcaacggtgg gtccggcggg gtcaaccagg ccggtggcaa tggcgggaat 480
gctgggctgt ggggcaatgg cggatccggc ggagccggcg ggaacgccac cactgccggc 540
cgcaacggct tcaacggggg cgccggggga agcggcggtt tgctgtgggg caatggcggt 600
gccggcgggg ccggtgggaa cggcggtccg gctccgctcg tgggcggggt gggcaccacc 660
ggtggcgccg gcgggaacgg cggcggcgcc gggttgttct acggtttcgg cggcgccggt 720
gggaacggcg ggatgggcgg ggtggcaccg agcaccggcc cctcgatggg catcctcccg 780
gccggcggtg tcggcgggcc tggtggctcc ggcggggcga gcgcgcttgc cttcggctcc 840
ggcggcgtcg gcggtgccgg tggcttgggc gggccgaccg atggcaccgt ccagggggtg 900
ggcggcttcg gcggtcaggg cggcaacggc gggcagagcg gcttgttgtt tggcaacgcg 960
ggagccggcg gggcaggcgc tgccggcgga gccggcaccg gcgacaccga gagcttcggc 1020
ggccacggcg gggccggcgg tgatggcggc gctgttggct tgatcggtaa cggcggggcc 1080
ggcggcaccg gatctcccgg cgctgtggtg ggtggtaacg gcggcgtcgg tggtctgggt 1140
ggcgccggca gtcccggggg tctgttgtac ggcaccgggg gggccggcgg caatggcgga 1200

-continued

```
ccgggtggtg acggtggtac tggcgcgacg gtgggctttg ccggctccgg cggtttcggc      1260
ggtgcggggg gcatcgccca gctgtttggc acggtggcca tgggtggtag cggcggtggt      1320
ataggcgctg gcaccacgac cgtggtgccg ccccgacgtcg ccccgtggg tggcacaggc      1380 ggcaatggcg gtcgcgccgg gctgctgttg ggtgtgggtg gcatgggcgg taatggcggt      1440
gccaccagcg tcgcgggac gctctacgcc gccggtggaa acgcggcga cggcgggttg       1500 gtgtggggca acggtggcac cggcgggagc ggtggcgccg gcggggcggg cagcgtcggc      1560
aacggcggtg cgggtggcaa cgcggcactg ctgttcggca acggcgggc gggcgggcc       1620 ggcggcgccg gcggcatcgg tgccggcgga gccggcggct cggcgcggt tctgtttggc      1680 aacgcgggg ctggcgggag cggtgccccc ggtggcatcg gcgccggtgg caatggcgga      1740
aacgcgctgc tggtcggcaa cggcggcaac ggtggggcag gtaccggtgg ggctgctggc     1800
ggtgccggtg gctcgggcgg gttgctattc ggccaaaatg ggatgcccgg gccg           1854
```

<210> SEQ ID NO 104
<211> LENGTH: 1242
<212> TYPE: DNA
<213> ORGANISM: Mycobacteria tuberculosis

<400> SEQUENCE: 104

```
gtgcatgagg tggctgctcg tgagcaacgt tcggacgggc cgatgaggct ggatgcgcag       60
ggccgactgc agcgttacga ggaggcgttc gctgactacg atgcaccgtt tgcgttcgta      120
gatctcgacg cgatgtgggg caatgccgat caactgcttg cgcgcgccgg cgacaagccg      180
atccgggtgg cgtcgaagtc gctgcgttgc cgaccactgc aacgcgaaat ccttgatgcc      240
agtgagcgat tcgacgggct attgacgttc acgcttaccg agacgctgtg gcttccggc      300 caaggtttct cgaacctgtt gttggcctac ccgccgaccg accgggcggc attgcgtgcg      360
cttggcgagc tgacggccaa ggacccggac ggggcgccga tcgtgatggt ggacagcgtg      420
gagcaccttg acctgatcga gcgcacgacc gacaagccgg tacggctgtg tctggatttc      480
gatgccggct attggcgcgc cggcgggcgg ataaaaattg gttccaagcg ctcgccgctg      540
cacaccccgg agcaggctcg cgcactcgcg gtggagatcg cgcggcggcc ggcgctaacg      600
ttggcggcgt tgatgtgcta cgaggccac attgcgggcc tcggtgacaa cgtcgccggc      660
aagcgggtcc acaacgcgat catccgtcgg atgcagcgca tgtcgttcga agagctgcgc      720
gagcgtcgtg cccgggccgt cgagctggtg cgcgaggtcg ccgacatcaa gatcgtcaac      780
gccggtggca ccggcgactt gcagctggtt gcgcaggagc cgttgattac cgaagcgacc      840
gccggctcgg gttttacgc gccgacactg ttcgactcgt attcgacgtt cacgctgcag      900
cccgcggcga tgttcgcgct gccggtatgc cgtcgtcccg gtgcaaagac cgtgaccgcg      960
ctcgggggtg gctatttagc cagcggggtc ggggcgaagg accgcatgcc gactccctac     1020
ctgccggtcg ggctgaagct caatgcgctg gagggaacgg gcgaagttca gacaccgcta     1080
tccggtgatg cagcccgacg gctgaagctt ggcgacaagg tctacttccg ccacaccaag     1140
gccggtgagc tgtgtgagcg gttcgaccat ctgcatctgg tccgtggcgc tgaagtagtc     1200
gacaccgtcc ccacctaccg gggtgaaggg cgcaccttcc tc                        1242
```

<210> SEQ ID NO 105
<211> LENGTH: 1284
<212> TYPE: DNA
<213> ORGANISM: Mycobacteria tuberculosis

<400> SEQUENCE: 105

```
atggacgagg cccacccggc tcacccggca gatgcggggc ggcccggtgg cccaattcaa      60
ggcgcgcgaa gaggagctgc catgacaccg atcaccgccc tgccgaccga gttggcggcc     120
atgcgcgagg tagtcgagac gctcgcaccc attgagcgtg ccgcgggcga gccgggtgag     180
cacaaggcgg ccgagtggat cgtcgagcgc ctgcgcacgg cgggcgcgca ggacgcgcgc     240
atcgaggagg agcagtacct cgacggctac ccgaggctgc acctcaagct gtcggtgatc     300
ggggtggcg ccggcgtcgc gggcctgctc agcagacgtt tgcgcatccc cgccgcgctg      360
gccggggtgg gtgcggggct ggcaatcgcc gacgattgcg ccaacgggcc gcgcattgtg     420
cgcaaacgaa cggagacgcc ccggacgaca tggaacgcgg tagccgaggc cggtgatcct     480
gctggtcagc taacagttgt tgtgtgcgct caccacgacg ccgcgcacag cggcaagttt     540
ttcgaggctc atattgagga ggtaatggtc gagctgtttc ccgggattgt ggagcgcatc     600
gacacgcagc tgccgaactg gtgggggccg atcctcgcgc ccgcactcgc cggtgtcggc     660
gccctgcgcg gcagccggcc gatgatgatc gccggaacgg tgggtagcgc cctgccgcc      720
gctttgttcg ccgacatcgc gcgcagtccg gtcgtccccg gtgccaacga caatctctcc     780
gcggttgcgc tgctggtcgc gctggccgag cggctgcgcg agcggccggt gaagggcgtg     840
cgagtgttgc tcgtgtccct gggggccgag gaaacgttgc agggcgggat ctacgggttc     900
ctggcgcgac acaaacccga gctggaccgc gaccgcacat acttcctgaa cttcgacacc     960
atcggctcac ccgagctcat catgctcgag ggcgagggcc cgacggtcat ggaggactac    1020
ttctatcggc cattccggga tctggtcatc cgggcggccg agcgcgccga cgcgccgctg    1080
cggcgcggca tccggtcgcg caacagtacc gacgcggtgt tgatgagccg cgccggctac    1140
ccgaccgcgt gctttgtgtc gatcaaccgg cacaagtcgg tggccaatta ccacctgatg    1200
tccgatacac ctgagaatct ctgctatgag acggtgtccc acgccgtcac cgtcgccgaa    1260
tccgtgatca gggagctggc ccga                                           1284
```

<210> SEQ ID NO 106
<211> LENGTH: 1284
<212> TYPE: DNA
<213> ORGANISM: Mycobacteria tuberculosis

<400> SEQUENCE: 106

```
atgagcccga tatggagtaa ttggcctggt gagcaagtct cgcgccgtc ggcgatcgta       60
cggccgacct cggaggctga gctggccgac gtgatcgcgc aggcggcgaa agaggcgag      120
cgggtacgcg cggttggcag cgggcattcg tttaccgaca tcgcctgcac ggacggggtc     180
atgatcgaca tgaccggcct gcagcgggtc ctcgacgtgg accagccgac tggcctggtg     240
acggtcgagg gggcgcaaa gctacgtgcg ctgggacccc aattggcgca acgacggctc      300
ggcctggaga accagggtga cgtggatccc caatccatca ccggcgcgac cgcgaccgcg     360
acgcacggaa ccggggtgcg tttccagaat ctgtcgcgc ggatcgtttc gctgcggctg      420
gtcaccgcgg gcggggaagt gctcagtctg tccgaaggtg acgattacct ggcggcacgg     480
gtttccctcg gcgcgctagg agtgatctca caggtcaccc tgcagacggt tccgctattc     540
acgttgcatc gccatgatca gcgacgctcg ctggcgcaga cgctggagcg cctcgacgag     600
ttcgtggacg gtaatgacca tttcgagttt ttcgtattcc cttacgcaga taaggcgttg     660
acgcgcacca tgcatcgcag tgacgagcag cccaaaccca cgcccgggtg gcagcgcatg     720
gtcggcgaga acttcgagaa cggggggattg agcctgatct gccagaccgg ccgtcgtttt     780
```

```
cctagtgtgg cgccgcgact gaaccgcctg atgacgaaca tgatgtcgtc ctccaccgtg      840
caagaccgcg cctacaaggt ctttgcgacc aacgcaagg tcaggttcac cgagatggag       900
tacgcgatcc cgcgtgaaaa cgggcgcgag gcgctccagc gtgtcatcga ccttgtgcgc      960
cgtcgcagct tgccgatcat gtttccgatt gaggtgcgat tctccgcccc cgacgattcc      1020
ttcctgtcga ccgcatatgg gcgcgacact tgctacatcg cggttcatca atacgccggt     1080
atggagttcg aaagctactt ccgcgccgtc gaggagatca tggacgacta cgccggtcgg     1140
ccacactggg gtaaacgtca ctatcagacc gccgccacgt tcgtgagcg ctatccgcag      1200 tgggatcggt tcgccgcggt tcgcgatcgc ctcgatccgg accgggtgtt tctcaacgac     1260
tacacccggc gcgttctcgg tccc                                            1284

<210> SEQ ID NO 107
<211> LENGTH: 309
<212> TYPE: DNA
<213> ORGANISM: Mycobacteria tuberculosis

<400> SEQUENCE: 107
ttgggttcaa caggaggtag ccaacccatg acggcgaatc gagggcccgc tgcaatctcg       60
agcggctcga actctggccg cgttctcgac accgccgggg tatcctcat cgctcttcgg      120 cggtgccccg cagagaccgc gttcgacgag ttgcacaacg ccgctcaacg gcacagattg     180
ccggtcttcg aaatagcttg gcactagtg catttggcgg tcgagggaag cacgccatgc     240
cggagcttcg tcgatgccca gtcggcggct cggcgggagt ggggtcagct ttttgcgcat     300
gcggcggcg                                                             309

<210> SEQ ID NO 108
<211> LENGTH: 744
<212> TYPE: DNA
<213> ORGANISM: Mycobacteria tuberculosis

<400> SEQUENCE: 108
gtgccgccta cggaaggaaa gtcgacaacg aatcgcgacg aaggcatcca ggtgctccgt       60
cgcgccgtcg ccgcgctgga cgaaatagct gccgaaccgg acacctgcg cctagtcgat     120 ctctgcgagc ggctggggct ggccaaatcg acgactcgac gcttgctggt cggcctggtc     180
gaggtggggc tggttagtgt cgattcgcac ggccgcttcg cactgggcga gcgtttgctg     240
ggattcggaa gtgtcaccgg agcccacata gccgcggcgt tccggccgac cgtcgagcga     300
gttgcccgcg cgaccgacgg cgaaacggtc gacctgtcgg tactgcgcgg ccagcgaatg     360
tggtttgtcg accagatcga atcgtcttac cggctgcgtg cggtctcagc cgtcgggctc     420
cgcttcccgt tgaacggaac cgcgaatgga aaagcggcgc tggctgctct cgacgacgcc     480
gacgccgagc ccgcgctctg ccgtctggat cccatggtgg ccgaaggtct acggcgcgag     540
atcgtcgaga tccggcgcac cggtatcgct ttcgaccgca acgagcacac cccagggata     600
tccgcggctc cgatcgcacg acgcgccctg ggcgacaacg tgatcgcgat ctcggtgccg     660
gcgcccaccg cacgatttct ggaaaaagag cagcgcataa tcgccgcgtt gcgcgccgcc     720
gcggactcgc cggactggac tcgc                                            744

<210> SEQ ID NO 109
<211> LENGTH: 1218
<212> TYPE: DNA
<213> ORGANISM: Mycobacteria tuberculosis
```

<400> SEQUENCE: 109

```
atggcatccg tcgcccaacc cgttaggcgc cgcccaaagg accggaagaa gcagattttg      60
gatcaggccg ttggactgtt catcgaacgt ggcttccatt cggtcaaatt ggaggacatt     120
gccgaggcgg ccggggtgac cgcgcgcgcg ttgtatcgcc actacgacaa caagcaggcg     180
ttgctcgccg aagcgatccg aaccggccag gatcagtacc agagcgcgcg tcgtctcacc     240
gagggcgaga cggagccgac gccgcggccg ttgaacgccg atctggaaga cctgatcgcc     300
gcggcggtcg cctctcgggc gttgacggtg ctgtggcagc gcgaggcccg ctacctcaac     360
gaggacgacc gcacggcggt ccggcgccgc atcaacgcga tcgtcgccgg catgcgtgac     420
agcgtgctgc tggaggtgcc cgatctgagt ccacagcatt cggagttgcg ggcgtgggcg     480
gtgtccagca ctttgaccag cctgggccgg cacagcctaa gcctgccggg cgaggaactg     540
aaaaagcttc tctaccaggc gtgtatggcc gcggcaagga cgcctcccgt ctgcgaattg     600
ccgccactgc cggccggtga tgccgcacgc gacgaggccg acgtgctgtt ctcccgctac     660
gagaccctgc tggccgcggg cgcgcggctg ttccgtgcgc agggctatcc ggccgtcaac     720
accagcgaaa tcggcaaggg agccggcatc gcgggcccgg ggctgtaccg ttcgttttct     780
tccaaacagg ccatcctgga cgcgctcatc cgccgcctcg acgagtggcg ctgcctggag     840
tgcatccgag cgctacgagc gaatcagcaa gcggcacaac ggttgcgcgg ccttgtccaa     900
gggcacgttc ggatcagctt ggacgctccg gatctggtgg cagtgtcggt caccgaactg     960
tcgcacgcct ctgtcgaagt acgcgacggc tacctgcgaa atcagggcga ccgcgaggcc    1020
gtgtggatcg acctcatcgg caagctggta cccgcgacca gtgtcgccca ggggcgactg    1080
ctggtcgcgg cggcgattag cttcatcgaa gacgtcgctc gcacctggca tctcacgcgc    1140
tacgccggag tcgccgacga gatcagtggc ctggcgctgg cgatcctgac cagcggggca    1200
ggtaacctct gcgcgca                                                   1218
```

<210> SEQ ID NO 110
<211> LENGTH: 795
<212> TYPE: DNA
<213> ORGANISM: Mycobacteria tuberculosis

<400> SEQUENCE: 110

```
atggtaatcg tggccgacaa ggcggccggt cgggtcgctg atccggtctt gcggccggtg      60
ggcgcgctgg gcgatttctt cgcgatgacg ctcgacacgt ccgtgtgcat gttcaagccg     120
cctttcgcgt ggcgtgaata cctacttcag tgctggttcg tggcgcgggt gtcgacgctg     180
cctggggtgt tgatgacgat cccatgggcg gtgatctcgg ggtttctctt caacgtcttg     240
ctgaccgaca tcggtgccgc ggacttttcc ggcaccggct gtgcgatctt caccgtgaac     300
caaagcgccc cgatcgtcac ggtcttggtg gtcgcgggcg cgggcgccac cgccatgtgc     360
gccgatctgg gtgcgcgcac catccgtgag gaactcgacg cactgcgggt gatgggcatc     420
aacccgatcc aagcgctagc ggctccgcgc gtgctggcgg ccaccacggt gtcgttggcg     480
ctgaattcgg tggtgaccgc gacggggctg atcggcgcgt tcttttgctc ggtgtttctc     540
atgcacgtct cggcggggc atgggtgacc gggcttacca cgctgaccca caccgtggac     600
gtcgtcattt cgatgatcaa ggcgacgttg ttcgggctga tggccggact gatcgcctgc     660
tataagggca tgtcggtcgg tggcggcccg gccggagtcg gccggcggt gaacgaaacc     720
gtggtgtttg ccttcatcgt cttgttcgtg atcaacatcg tcgtcaccgc ggtcggcatc     780
ccattcatgg tgtcc                                                     795
```

<210> SEQ ID NO 111
<211> LENGTH: 813
<212> TYPE: DNA
<213> ORGANISM: Mycobacteria tuberculosis

<400> SEQUENCE: 111

| | | | | | |
|---|---|---|---|---|---|
| atgacggcag | cgaaagccct | tgtaagcgaa | tggaatcgga | tgggatcgca | gatgcggttc | 60 |
| ttcgtcggca | cgctggccgg | gattcccgac | gccctcatgc | actaccgcgg | cgagctgctg | 120 |
| cgggtgatcg | cgcaaatggg | gttggggacc | ggggttcttg | cggtgatcgg | tggaacggtc | 180 |
| gcgatcgtcg | ggttcttggc | gatgaccacc | ggcgcgatcg | tggccgtgca | gggctacaac | 240 |
| cagttcgctt | cggtgggtgt | ggaggcgctg | accggcttcg | cgtcggcctt | cttcaacacc | 300 |
| cgcgagattc | agcccggaac | cgtgatggtc | gcgctagcgg | ccaccgtcgg | tgccggtacc | 360 |
| accgctgcgc | tgggggcgat | gcggataaac | gaggagatcg | acgcgctcga | ggtgatcggc | 420 |
| atccgcagca | tcagctacct | ggcgagcacc | cgggtgctgg | ccggagtggt | cgtggccgtc | 480 |
| cctctgttct | gtgtgggact | gatgacggcc | tacctggccg | cgcgcgtcgg | caccaccgcc | 540 |
| atctatggcc | aggggtcggg | cgtgtacgac | cactacttca | acacgttcct | gcgcccgacc | 600 |
| gacgtgctct | ggtcgtcggt | tgaagtcgtc | gtggtcgctc | tgatgatcat | gctggtgtgc | 660 |
| acctattacg | gctacgccgc | acatggcggg | ccggccgggg | ttggcgaggc | ggtcggccgg | 720 |
| gccgtgcgtg | cctcgatggt | cgtcgcgtcg | atcgcaatcc | ttgtcatgac | gctggccatc | 780 |
| tacggccagt | cgcccaactt | tcacctggcg | acc | | | 813 |

<210> SEQ ID NO 112
<211> LENGTH: 1275
<212> TYPE: DNA
<213> ORGANISM: M. tuberculosis

<400> SEQUENCE: 112

| | | | | | |
|---|---|---|---|---|---|
| atgagacgcg | ggccgggtcg | acaccgtttg | cacgacgcgt | ggtggacgct | gatcctgttc | 60 |
| gcggtgatcg | gggtggctgt | cctggtgacg | gcggtgtcct | tcacgggcag | cttgcggtcg | 120 |
| actgtgccgg | tgacgctggc | ggccgaccgc | tccgggctgg | tgatggactc | cggcgccaag | 180 |
| gtcatgatgc | gcggtgtgca | ggtcggccgg | gtcgcccaga | tcggtcggat | cgagtgggcc | 240 |
| cagaacgggg | cgagcctcag | actggagatc | gaccccgacc | agatccggta | catcccggcc | 300 |
| aatgtcgagg | cacagatcag | cgccaccacc | gcattcggtg | ccaagttcgt | cgacctggtg | 360 |
| atgccgcaaa | acccaagtcg | tgcacggctg | tccgctgggg | cggtactgca | ttcgaagaac | 420 |
| gtcagcacgg | aaatcaacac | cgtcttcgaa | acgtcgtcg | acctgctcaa | catgatcgac | 480 |
| ccgctgaaac | tgaacgccgt | gctgaccgcg | gtcgccgacg | ccgttcgcgg | gcaaggtgaa | 540 |
| cggataggcc | aggccaccac | cgacctcaac | gaggtgctgg | aggcactcaa | cgcacgcggc | 600 |
| gacaccatcg | gcggcaactg | gcgatcgctc | aagaacttca | ccgacaccta | tgacgcggcc | 660 |
| gcccaagaca | tcctgacgat | cctgaacgcc | gccagcacca | ccagtgcgac | cgtcgtgaat | 720 |
| cattcgacgc | agctggatgc | cttgctactc | aacgccatcg | gactatccaa | cgctggcacc | 780 |
| aacctgcttg | gcagcagccg | agacaatctc | gtcgcgcgg | ccgacatcct | ggcgccgacc | 840 |
| acgagcctgc | tgttcaagta | caaccccgaa | tacacctgct | tcctgcaggg | cgccaagtgg | 900 |
| tatctcgaca | acggcggcta | tgcggcctgg | ggcggggcca | acgggcgcac | gctacaactc | 960 |
| gatgtggcgc | tactgttcgg | caacgacccc | tatgtctatc | cggacaacct | gccggttgtc | 1020 |

-continued

| | |
|---|---|
| gcggccaagg ggggtcccgg cggaaggccg ggatgcgggc cattgccgga tgccacccac | 1080 |
| aacttcccgg tgcgccagct ggtcaccaac accggatggg gaaccgggct ggacatccgg | 1140 |
| cccaaccccg gcatcgggca tccctgctgg gccaactact tcccggtgac ccgcgcggtg | 1200 |
| cccgagccgc cgtcgatccg tcagtgcatc cccgggccgg cgatcgggcc caaccccgcg | 1260 |
| gcggggagc agcca | 1275 |

<210> SEQ ID NO 113
<211> LENGTH: 1026
<212> TYPE: DNA
<213> ORGANISM: Mycobacteria tuberculosis

<400> SEQUENCE: 113

| | |
|---|---|
| atgagggaga acctgggggg cgtcgtggtg cgcctcggcg tcttcctggc ggtatgcctg | 60 |
| ctgacggcgt tcctgctgat tgccgtcttc ggggaggtgc gcttcggcga cggcaagacc | 120 |
| tactacgccg agttcgccaa cgtgtccaat ctgcgaacgg gcaagctggt gcgcatcgcc | 180 |
| ggcgtcgagg tcggcaaggt caccaggatc tccatcaacc ccgacgcgac ggtgcgggtg | 240 |
| cagttcaccg ccgacaactc ggtcaccctc acgcggggca cccggcggt gatccgctac | 300 |
| gacaacctgt tcggtgaccg ctatttggcg ctggaggaag gggccggcgg actgccgtt | 360 |
| cttcgtcccg gtcacacgat tccgttgcg cgcacccaac cggcgttgga tctggatgcc | 420 |
| ctgatcggtg gattcaagcc gctgtttcgt gcgctgaacc ccgagcaggt caacgcgctg | 480 |
| agcgaacagt tgctgcacgc gtttgccgga caggggccca cgatcgggtc attgctggcc | 540 |
| cagtccgcgg ccgtgaccaa caccctggcc gaccgtgatc ggctgatcgg gcaggtgatc | 600 |
| accaacctca acgtggtgct gggctcgctg gcgctcaca ccgatcggtt ggaccaggcg | 660 |
| gtgacgtcgc tatcagcgtt gattcaccgg ctcgcgcaac gcaagaccga catctccaac | 720 |
| gccgtggcct acaccaacgc cgccgccggc tcggtcgccg atctgctgtc gcaggctcgc | 780 |
| gcgccgttgg cgaaggtggt tcgcgagacc gatcgggtgg ccggcatcgc ggccgccgac | 840 |
| cacgactacc tcgacaatct gctcaacacg ctgccggaca ataccaggc gctggtccgc | 900 |
| cagggtatgt acggcgactt cttcgccttc tacctgtgcg acgtcgtgct caaggtcaac | 960 |
| ggcaagggcg ccagccggt gtacatcaag ctggccggtc aggacagcgg gcggtgcgcg | 1020 |
| ccgaaa | 1026 |

<210> SEQ ID NO 114
<211> LENGTH: 1230
<212> TYPE: DNA
<213> ORGANISM: Mycobacteria tuberculosis

<400> SEQUENCE: 114

| | |
|---|---|
| atgaaatcct tcgccgaacg caaccgtctg gccatcggca cagtcggcat cgtcgtcgtc | 60 |
| gccgccgttg cgctggccgc gctgcaatac cagcggctgc cgttttttcaa ccagggcacc | 120 |
| agggtctccg cctatttcgc cgacgccggc gggctgcgca ccggcaacac cgtcgaggtc | 180 |
| tccggctatc cggtgggaaa agtgtccagc atctcgctcg acggaccggg cgtgctggtg | 240 |
| gagttcaagg tcgacaccga cgtccgactc ggaaaccgca ccgaagtggc aatcaaaacc | 300 |
| aagggcttgt tgggcagcaa gttcctcgac gtcaccccc gcgggacgg ccgactcgat | 360 |
| tctccgatcc cgatcgagcg gaccacgtcg ccctaccaac tgcccgacgc ccttggcgat | 420 |
| ttggccgcca cgatcagcgg gttgcacacc gagcggctgt ccgaatcgct ggccaccctg | 480 |
| gcgcagacct tgccgatac gccggcgcac ttccgcaacg ccatacacgg ggtggcccgg | 540 |

```
ctcgcccaaa ccctcgatga gcgcgacaac caactgcgca gcctgctggc caacgcggcc      600
aaagccaccg gggtgctggc caaccgcacc gaccagatcg tcggcctggt gcgcgacacg      660
aatgtggtct tggcgcagct gcgcacccaa agcgccgccc tggaccggat ctgggcgaac      720
atctcggcgg tggccgaaca actgcggggc ttcatcgctg agaaccgcca gcagctgcgc      780
ccggcgctgg acaagctcaa cggggtgctg gctatcgtcg aaaaccgcaa agagcgtgtg      840
cggcaggcca tcccgctgat caacacctat gtcatgtcgc tgggtgagtc gctgtcgtcg      900
ggcccgttct tcaaggcata cgtggtgaac ctgctgccgg tcagttcgt gcaaccgttc       960 atcagcgccg cgttctccga cctggggctc gacccggcca cgttgctgcc gtcgcagctg      1020
accgacccac cgaccggtca acccggaacc ccgccgttgc cgatgcccta cccgcgcacg      1080
ggccagggcg gtgagccgcg gctgacgctg cccgacgcga tcaccggcaa tcccggcgat      1140
ccgcgctatc cgtaccggcc ggagccgccc gcgccgccgc cggcgggcc gccgcccggc       1200 ccgcccgcgc agcagccggg agaccaaccg                                       1230

<210> SEQ ID NO 115
<211> LENGTH: 1269
<212> TYPE: DNA
<213> ORGANISM: Mycobacteria tuberculosis

<400> SEQUENCE: 115
gtgacaacga aactcagacg tgcccgctcg gtgttggcga ccgccctggt gctggtcgcg       60
ggcgtgatcc tggccatgcg caccgccgac gccgccgccc gcacgaccgt ggtcgcctac      120
ttcgacaaca gcaacggtgt gttcgccggt gacgacgtgc tcattcgggg cgtgccggtg      180
ggcaagatcg tcaagatcga accgcaaccg ctgcgcgcca agatttcgtt ctggttcgac      240
cgcaaatacc gagtccccgc cgatgccgcc gcggcgatcc tgtcgccgca actggtgacc      300
ggccgggcca tccagctgac accgccgtat gccggcgggc cgaccatggc cgacggcaca      360
gtaatcccgc aagagcgcac cgtggtgccg gtggagtggg acgacttgcg ggcgcaactt      420
cagcggctga ccgcattgct gcagcccacc cggccgggcg gcgtcagcac gctgggtgcg      480
ctcatcaata ctgccgccga caacctgcgc gggcaaggcg ccaccatccg cgacaccatc      540
atcaaactgt cacaagcgat tcggctctc ggtgaccaca gcaaagacat cttctccacc       600
gtgacgaacc tgtcgacgct ggtcacggcc ctgcatgaca cgcgctgacct gctcgaacgg      660 ctcaaccaca acctggccgc ggtgacctcg ctgctggccg atggcccgga caagatcggt      720
caggcagccg aggacctcaa cgcggtcgta gccgacgtcg gcagcttcgc cgccgagcac      780
cgcgaggcga tcggcaccgc atcagacaag ctcgcgtcaa tcaccaccgc gctggtcgac      840
agcctcgacg acatcaagca gacgctgcat atcagcccga cggtgttgca gaacttcaac      900
aacatcttcg aacggccaa cggcgcgctg accgcgcgc tggcgggcaa caacatggcc       960
aacccaatcg ccttcctgtg cggcgcgatc caggctgcct cccggctggg cggcgagcaa     1020
gcggccaaat tgtgcgtgca atacctggcg ccgatcgtga agaaccgcca gtacaactac     1080
ccgccgctgg gggcgaacct gttcgtcggg gcgcaggcca ggcctaacga ggtcacctac     1140
agcgaggact ggctgcggcc cgattacgtt gcaccagttg cggacacgcc gccagatccg     1200
gccgcggccg tgaccgtcga tcccgcgacc ggcctgcgcg catgatgat gccgccgggg      1260 ggtggctcg                                                             1269

<210> SEQ ID NO 116
```

-continued

<211> LENGTH: 1131
<212> TYPE: DNA
<213> ORGANISM: M. tuberculosis

<400> SEQUENCE: 116
gtgaggatcg gcctgaccct ggtgatgatc gcggccgtgg tagcgagctg cggctggcgc 60
gggctgaatt cgctgccgct gcccggcacg cagggcaacg gcccggggtc cttcgcggtc 120
caggcgcagc tgccggatgt caacaacatc cagccgaact cgcgggtgcg ggttgccgac 180
gtgacggtcg gccacgtcac gaaaatcgag cgccaaggct ggcacgcgtt ggtgaccatg 240
cggctggatg gcgacgtcga tttgcccgcc aacgcaacgg ccaagatcgg caccaccagc 300
ctgctgggtt cctaccacat cgagctggcg ccaccgaaag gcgaagcgcg gcaaggcaag 360
ctgcgcgacg gttcactcat tgcgctgtca cacggtagcg cctacccaag caccgagcag 420
acgctggcag cgctgtcgct ggtgctcaac ggcggcggac tgggccaggt tcaagacatc 480
accgaggcgt tgagcaccgc gtttgccggc cgtgagcacg atctgcgcgg gctgattggg 540
cagctggaca ccttcaccgc atacctcaac aaccagtccg gtgacatcat cgcggccacc 600
gacagcctca accgcctcgt cggcaagttc gccgaccagc aacccgtctt cgatcgggcc 660
ctggccacca tccccgacgc gctcgcggtg ctggccgatg agcgggacac gctcgtcgag 720
gctgccgagc agctgagcaa gttcagcgcc ctgaccgtcg actcggtcaa caagaccacc 780
gcgaacctgg tcaccgaact gcggcaactc ggaccggtgt tggagtcgct ggccaattcc 840
ggtccggcgc tgacccgatc gctgtccctg ctggccacgt tcccgttccc gaacgagacg 900
ttccaaaatt tccagcgcgg cgaatacgcc aacctgaccg cgatcgtcga cctcacgctc 960
agccgcatcg accagggcct gttgaccggc acccgctggg agtgtcatct gacccagctc 1020
gagctgcagt ggggtcgcac cattgggcag ttccccagcc cgtgtaccgc gggctatcgg 1080
ggtaccccgg gcaatccgct gacgatcgcc taccgctggg atcaggggcc c 1131

<210> SEQ ID NO 117
<211> LENGTH: 1311
<212> TYPE: DNA
<213> ORGANISM: Mycobacteria tuberculosis

<400> SEQUENCE: 117
atgctgcatc taccgcgccg agtgatcgtt cagctggccg tctttaccgt gatcgcggtg 60
ggcgtgctgg ccatcacgtt cctgcatttc gtgaggctgc cggcgatgct tttcggcgtc 120
ggccgctaca cggtgacgat ggagctggtc gaagccggtg ggctgtatcg caccggcaat 180
gtcacctacc gcggctttga ggtgggccgg gtggcagcgg tgcggctcac cgacaccggg 240
gtgcaagcgg tgctggccct gaaatcgggc atcgatatcc cgtcggacct caaggccgag 300
gtgcacagcc acaccgcgat cggcgaaacc tacgtcgagt tgttgccgcg caacgccgcc 360
tcgccgccac tgaagaacgg cgatgtcatt gcgctggccg acacctcggt gccgcccgac 420
atcaacgacc tgctcagcgc ggccaacacc gcattggagg caatacctca cgagaacctg 480
cagaccgtca tcgacgagtc gtacaccgcg gtggccgggt tagggctcga actttcccgg 540
ctgatcaagg gctcggcgga actggcgatc gatgctcgcg cgaatctcga tccgctggtg 600
gcgctgatcg accgggcagg accggtgctg gattcgcaga cccacacctc ggatgcgatc 660
gcggcctggg cggcacagct ggccgcagtc accggccaat tgcagacaca cgactcggcg 720
gtcggcgatc tcatcgaccg gggcggtccg gcgttggggg agacgcgcca actgctcgag 780
cggctacaac ccaccgtgcc catcctgctg gccaacctgg tcagcgtcgg ccaggtcgca 840

```
ctcacctatc acaacgacat cgaacagctg ctggtggtgt tccccatggc catcgccgcc     900
gaacaggccg gcatcctggc caacctcaac accaagcagg cctaccgggg ccagtatctg     960
agcttcaacc tcaacctgaa cctgccgccg ccgtgcacca ccggctttct gccggcccag    1020
cagcggcgca ttcccacgtt cgaggactac ccggatcgcc cggccggtga tctgtactgc    1080
cgggtgcccc aggattcgcc gtttaacgtg cgcggcgccc gcaacatccc ctgtgaaacc    1140
gtgccgggca agcgcgcacc caccgtgaag ttatgcgaga cgacgcgcc atacctgccg     1200 ctgaacgacg gctacaactg gaagggcgac cccaacgcca cggtgccggg tttggggtcc    1260
ggccaggaca tcccgcagac atggcaaacg atgctgctgc cgccgggcag c             1311
```

<210> SEQ ID NO 118
<211> LENGTH: 573
<212> TYPE: DNA
<213> ORGANISM: Mycobacteria tuberculosis

<400> SEQUENCE: 118

```
atgtcggtag cagtggattc cgacgccgag gatgacgccg tatcggagat cgctgaggca      60
gccggcgtgt cgccggcccc agccaaacca tccatgtcgg cgccgcggcg catgctgctg     120
ttcggcctgg tcgtcgtcgt cgctttggcg gtgctgttgt gttgctgggg atttcgcgtc     180
cagcgggcac gccatgcgca ggaccagcgt ggtcacttcc tgcaagcggc ccggcagtgc     240
gcgctgaacc taacgaccat cgactggcgc aacgccgagg cggatgtgcg ccgcattctg     300
gacggcgcca caggcgagtt ttacaacgac ttcgcccagc ggtcccagcc cttcgtcgaa     360
gtactgaggc acgcaaaggc cagcacggtc ggcacgatca ccgaggccgg gctgcagacg     420
cagaccgccg acacggccca ggcgctggtg gcggtgtccg tgcaaacgtc gaatgccggc     480
gaagccgacc cggttccacg agcgtggcga atgcgcatca ccgtgcagcg ggtcggcgac     540
cgggtcaagg tgtccgacgt cgggttcgtg ccg                                  573
```

<210> SEQ ID NO 119
<211> LENGTH: 480
<212> TYPE: DNA
<213> ORGANISM: Mycobacteria tuberculosis

<400> SEQUENCE: 119

```
gtgagctggt cgcgggtgat cgcctacggg ctgctgcccg ggctggcgtt ggcgctgacg      60
tgtggcgcgg gcttgctgaa atggcaggac ggcgccgtcc gcgacgccgc ggttgcccgt     120
gcggaatccg tgcgggccgc gaccgacggg accaccgcgc tgctgtctta ccggcccgac     180
accgtgcagc atgacctcga gagcgcgcga agcaggctca cgggcacgtt cctcgacgcc     240
tacacacagc tgacccacga cgtggtgatc cccggcgcac agcagaagca gatctcggcc     300
gtggccaccg tcgcggccgc ggcgtcggtg tcgacttccg ccgaccgcgc cgtcgtcctg     360
ctgttcgtaa accagaccat caccgtcggc aaggacgcgc cgaccaccgc gcttccagc     420 gttcgggtga ccctcgacaa catcaacggg cgttggctga tctcgcaatt cgaaccgatc     480
```

<210> SEQ ID NO 120
<211> LENGTH: 375
<212> TYPE: DNA
<213> ORGANISM: Mycobacteria tuberculosis

<400> SEQUENCE: 120

```
gtgcagcgcc aatcattgat gccccagcag acccttgccg ccggcgtttt cgtgggtgcg      60
```

```
ctgctatgcg gtgtcgtgac ggcggcggtg ccaccacacg cacgcgccga cgtggtcgcc      120
tatctggtca acgtgacggt acgcccgggc tacaacttcg ccaacgccga cgccgcgttg      180
agttacggac atggcctctg cgagaaggtg tctcggggcc gcccttacgc acagatcatc      240
gccgacgtca aggctgattt cgacacccgc gaccaatacc aggcctcgta tctgctcagc      300
caggctgtca acgaactctg ccccgcgctg atctggcagt tgcgaaactc cgcagtcgac      360
aatcggcgct cgggc                                                      375

<210> SEQ ID NO 121
<211> LENGTH: 663
<212> TYPE: DNA
<213> ORGANISM: Mycobacteria tuberculosis

<400> SEQUENCE: 121
atgtcgcgtc gagcatcggc cacgtgtgcc ttgtccgcga ccaccgccgt cgccataatg       60
gctgctcccg ccgcacgggc cgacgacaag cggctcaacg acggcgtggt cgccaacgtc      120
tacaccgttc aacgtcaggc cggctgcacc aacgacgtca cgatcaaccc gcaactacaa      180
ttggccgccc aatggcacac cctcgatctg ctgaacaacc ggcacctcaa cgacgacacc      240
ggttctgacg gatccacacc gcaagaccgc gcgcatgccg ccggcttccg cgggaaagtc      300
gctgaaaccg tggcgatcaa tcccgccgta gcgatcagcg catcgagtt gataaaccag       360 tggtactaca accccgcgtt tttcgcgatc atgtccgact cgccaacac ccagatcggg       420 gtgtggtcag aaaacagccc ggatcgcacc gtcgtggtgg ccgtttacgg acagcccgat      480
cgaccttccg cgatgccgcc caggggagcg gtaaccggac cgccgtcccc ggtggccgcg      540
caagagaacg ttcctatcga ccccagcccc gactacgacg ccagcgacga gatcgaatac      600
ggcatcaact ggctgccatg gatcctgcgc ggcgtgtacc cgccgcccgc aatgccgccg      660
cag                                                                   663

<210> SEQ ID NO 122
<211> LENGTH: 405
<212> TYPE: DNA
<213> ORGANISM: Mycobacteria tuberculosis

<400> SEQUENCE: 122
gtgcggtgga ttgtcgacgg tatgaacgtg atcggaagtc gtccggatgg ttggtggcgc       60
gaccgccatc gcgcgatggt gatgctggtg gaaaggctcg aggggtgggc catcaccaag      120
gctcggggcg acgacgtgac ggtggtgttc gagcggccgc cgtcgaccgc catcccgtca      180
tcggtggtca agtggcgca tgcgcccaag gcggccgcca actcgccga cgacgagatc        240 gtccggctgg tccgatccgg cgcccagcca caagagattc gtgtggtgac atcggacaaa      300
gcgttgaccg accgggtccg agacttgggt gcggcagtct acccggcaga acggttccgt      360
gaccttatcg acccgcgcgg gtcgaacgcg gcccgccgca cgcag                      405

<210> SEQ ID NO 123
<211> LENGTH: 1044
<212> TYPE: DNA
<213> ORGANISM: Mycobacteria tuberculosis

<400> SEQUENCE: 123
atgtctcaga caccccgctac aacccgcaaa acgtttcccg agatcagctc aagagcgtgg       60 gagcacccccg ccgaccggac cgcccttttcc gcgctgcgcg ggctcaaagg cttcgaccag      120
atcttgaagc tgatgtcggg gatgttgcgg gaacggcagc accggctgct gtacctggcc       180
```

| | |
|---|---|
| agcgcggcac gggtcgggcc gcggcagttc gccgacctcg acgcgctgct ggacgaatgc | 240 |
| gtggatgtgc tggacgcgtc ggcgaaaccc gaactctacg tgatgcagtc accaatcgcg | 300 |
| gatgccttca ccatcggcat gggcaagcca ttcaccgtga tcacctcggg gctgtacgac | 360 |
| ctggtgacac acgacgagat gcggttcgtg atgggccacg agctcggcca cgcactgtcc | 420 |
| ggccacgcgg tgtaccgcac gatgatgatg catctgctgc ggttggcccg gtcattcggc | 480 |
| gtcttgccgg ttggcggctg ggcgctgcgc gcaatcgtgg ctgcgctgct ggaatggcag | 540 |
| cgcaaatcgg agctgtccgg cgatcgcgct gggttgctgt gcgcgcagga tttggacacc | 600 |
| gcgctcaggg tggagatgaa gctcgctggc ggctgccggc tggacaagct ggactcggag | 660 |
| gccttcttgg ctcaggcccg ggaatacgag acatccggcg atatgcgcga cggggtgctc | 720 |
| aagctgctca acctggagct gcagacccat ccgttctctg tgctgcgggc tgccgccttg | 780 |
| actcactggg tggacaccgg cggctatgcc aaggtgatag ccggcgagta cccgcgtcgg | 840 |
| gccgacgacg gcaacgccaa atttgcagac gaccttggcg cggccgcccg gtactaccgg | 900 |
| gacggcttcg accagtccaa cgacccgctg atcaaaggta tccgcgacgg attcggtggc | 960 |
| atcgtcgagg gcgtgggacg ggcagcctcg aacgcggccg attcattggg ccgcaagatc | 1020 |
| accgagtggc ggcagccctc gaag | 1044 |

<210> SEQ ID NO 124
<211> LENGTH: 564
<212> TYPE: DNA
<213> ORGANISM: Mycobacteria tuberculosis

<400> SEQUENCE: 124

| | |
|---|---|
| atgactacgc gtccggcaac cgaccgccgc aagatgccca ctgggcggga agaggtagcg | 60 |
| gccgcaatcc tgcaggccgc caccgacctg ttcgccgagc gtgggccagc cgcgacgtcg | 120 |
| attcgcgaca tcgccgctcg atccaaggtc aaccacgggc tggtgtttcg tcacttcggc | 180 |
| accaaggacc aactggttgg ggccgtgctc gatcacctgg gcacgaagct gaccagactg | 240 |
| ttgcactccg aggcgcccgc tgacatcatc gaacgggctc tcgaccgaca tgggcgggtc | 300 |
| ttagcccggg cactgctgga cggatatccc gtgggccagc tgcaacagcg atttcccaat | 360 |
| gttgcggagc tgctcgacgc ggtacggcct cgctacgaca gcgacttggg cgcgcggctg | 420 |
| gcggtcgcgc acgcccttgc gctgcaattc ggttggcggc tctttgcgcc catgctgcgc | 480 |
| tcggcgacgg gtatcgacga gctgaccggt gacgaactac ggctgtccgt gaacgatgcg | 540 |
| gtagcccgga tcctggaacc gcac | 564 |

<210> SEQ ID NO 125
<211> LENGTH: 702
<212> TYPE: DNA
<213> ORGANISM: Mycobacteria tuberculosis

<400> SEQUENCE: 125

| | |
|---|---|
| gtgacgatat tgatcctgac cgacaacgtc cacgcccatg ctctggcggt cgatctgcag | 60 |
| gccaggcatg gcgatatgga cgtctatcag tcccccatcg gccagctgcc gggtgtcccg | 120 |
| cgatgtgatg tcgcagagcg cgtcgcggaa atcgtggagc ggtatgacct cgtccttccc | 180 |
| ttccactgta aacagaggtt tcccgccgct tgatcgatg gggtcaggtg tgtgaatgtt | 240 |
| catccggggtt tcaaccccta caaccgcggc tggtttcccc aggtcttctc gatcatcgac | 300 |
| gggcaaaaag tcggcgtgac gatccacgag atcgacgatc agttggacca tggtccgatc | 360 |

| | |
|---|---|
| atcgcccagc gggaatgcgc gatcgagtcg tgggattcct cgggaagtgt ctacgcccgg | 420 |
| ctgatggaca tcgagcgtga gttggtgctg gaacatttcg acgccatccg ggacggcagc | 480 |
| tacacggcta aatcgccggc caccgagggc aacctcaacc tgaaaaagga tttcgaacaa | 540 |
| ctccggcggc tagacctgaa cgagcgcgga acgtttgggc atttcctgaa tcgcctgcgc | 600 |
| gcgttgaccc atgatgattt ccgcaacgct tggttcgtcg atgcgtcagg ccgcaaggtg | 660 |
| tttgtccgcg tcgtgctcga accggagaag cccgcggaag cc | 702 |

<210> SEQ ID NO 126
<211> LENGTH: 1599
<212> TYPE: DNA
<213> ORGANISM: Mycobacteria tuberculosis

<400> SEQUENCE: 126

| | |
|---|---|
| atgttagcct tcccttattt gatgactatg atcactccac ctaccttcga cgttgcgttc | 60 |
| atcggcagcg gggccgcgtg ctctatgact ctgctggaaa tggccgatgc cctgctgagc | 120 |
| agccctcgg catcgcccaa gttgcgcatc gcggtggtgg agcgagacga gcagttctgg | 180 |
| tgcggaatcc cctatggcca acgctccagc atcggatcgc tggccattca gaagctcgac | 240 |
| gatttcgccg acgagccgga aaaggccgcc taccggatct ggctggagca gaacaagcag | 300 |
| cgctggctgg cgttcttcca ggcagagggc ggtgcggccg cggcccgctg gatctgcgac | 360 |
| aaccgcgacg cattggacgg caaccagtgg ggggagctct acctgccgcg gtttctcttc | 420 |
| ggtgtatttc tgtcggagca gatgattgcc gccatcgccg cgctcggcga gcgtgacctg | 480 |
| gccgaaatcg tcaccatccg cgctgaggcc atgagcgccc actccgcaga cggccactac | 540 |
| cgaatcggcc tccgcccgtc tggaaacggt ccaacggcaa ttgctgcagg caaagtggtt | 600 |
| gtggccattg cagcccccc gaccaaagcc atccttgcga gcgattccga acccgcattc | 660 |
| acctatatca acgatttcta ctcccccggc ggggagagca acgttgcgcg actgcgcgat | 720 |
| tcgctcgacc gcgtcgagtc gtgggagaag cgcaacgtac tggtcgtggg ttccaacgcc | 780 |
| acctcgctgg aagcgctcta cctaatgcgt cacgacgcgc gcatccgcgc acgcgtccgg | 840 |
| tccatcaccg tcatctcgcg ctccggcgtg ctgccctaca tgatctgcaa tcagccgccg | 900 |
| gagtttgact tccgcggct gcgcacgctg ctctgtacgg aagcgatcgc cgcggcggat | 960 |
| ctcatgtccg cgatccgcga cgatctcgcg acggccgaag aacgctcgtt gaacctggcc | 1020 |
| gatttgtacg acgccgttgc cgccctgttt gggcaggcgc tgcacaagat ggatctcgtg | 1080 |
| cagcaggaag agttcttctg cgtgcacggc atgaacttca ccaagttggt gcggcgtgcg | 1140 |
| ggacgcgatt gccgccaggc atccgaggag ctagccgcgg acggcacgct gagcctgctc | 1200 |
| gccggcgaag tactgcgcgt ggatgcctgc gcgtccggcc agccgttcgc caccatgacc | 1260 |
| taccgagccg cgggagccga gcatacccac cccgtcccct tcgctgcggt ggtgaattgt | 1320 |
| ggcggtttcg aggagctgga cacgtgttcc tcgccgttcc tggtcagcgc gatgcagaac | 1380 |
| gggctgtgcc gcccgaaccg caccaaccgt ggccttctgg ttaacgacga cttcgaggcc | 1440 |
| agcccaggtt tttgcgtcat cgggcccta gtcggcggca atttcactcc caagatccgt | 1500 |
| ttttggcacg tcgagagcgc accgcgcgtc cggtcgctgg cgaaatcgct ggcggccagc | 1560 |
| ctgcttgctt cgctccagcc cgtcgcactg gccccatgc | 1599 |

<210> SEQ ID NO 127
<211> LENGTH: 1236
<212> TYPE: DNA
<213> ORGANISM: Mycobacteria tuberculosis -continued

<400> SEQUENCE: 127

```
atgaagatcc gaacgttatc cggctcggtg ctggagccgc cgtccgcagt acgcgcgacc      60
ccaggcacgt ccatgttaaa actcgagccg ggtggctcga cgatccccaa gatccccttc     120
atccgcccga gctttcccgg gccagccgag ctcgccgagg acttcgtaca gatcgcccag     180
gctaactggt acacgaactt cggtccgaac gagcggcggt ttgcccgcgc cctgcgcgac     240
tatctgggac ctcatctgca cgttgctacc ctcgccaacg gcaccctggc actcctcgcg     300
gcgctccacg tcagtttcgg cgccggtacg cgggaccgct acctgctgat gccgtcgttc     360
acgttcgtcg gcgtggctca ggctgcgcta tggactgggt accgtccctg gttcatcgac     420
atcgacgcca acacatggca gccatgcgtc cactccgccc gcgccgtcat cgaacgcttc     480
cgcgaccgga tcgccggcat cctgctggcc aatgtgttcg gcgtcggcaa tccccagatc     540
agcgtctggg aggagctcgc cgccgaatgg gagctaccga ttgtgctcga ctcggcggcc     600
ggcttcggct ccacgtacgc cgacggcgag cgcctcggtg gacgcggtgc atgcgagatc     660
ttctccttcc atgcgaccaa gccgttcgcg gttggtgagg gcggcgctct ggtttctcgc     720
gatccacggc tcgtcgagca cgcatacaag ttccagaact tcggcttggt gcaaacacgc     780
gagtccatcc agctcggaat gaacggcaag ctgtcggaga tcagcgccgc tattggccta     840
cgccaactag tcgggcttga tcgccgcctg gcaagtcgcc gcaaggtcct cgagtgctat     900
cgcaccggta tggccgacgc gggtgtgcgt ttccaggaca acgccaatgt tgcgtcgctc     960
tgtttcgcga gcgcttgctg cacgtccgcc gaccacaagg ccgcggttct gggtagcctg    1020
cgtaggcacg cgatcgaggc gcgcgactac tacaacccac cgcagcaccg acatccgtac    1080
tttgtgacga atgccgagtt agtcgagtcg accgatctag ccgtcacggc ggacatttgc    1140
tcgcgaatcg tgtcgctgcc agtccacgac cacatggccc cggatgacgt tgcccgggtc    1200
gtcgccgccg tgcaggaagc ggaggtgcgc ggtgaa                              1236
```

<210> SEQ ID NO 128
<211> LENGTH: 2358
<212> TYPE: DNA
<213> ORGANISM: Mycobacteria tuberculosis

<400> SEQUENCE: 128

```
atgatcaccg aggacgcctt ccccgtcgaa ccgtggcagg tccgcgagac caagctcaac      60
ctgaacctgc tggcccagtc cgaatcccta ttcgccttgt ccaacgggca cattggatta     120
cgcggcaacc tcgacgaggg cgaacccttc ggactgccgg gcacctacct gaactctttc     180
tacgaaatcc ggccgctgcc gtacgccgag gccggttatg gatatccgga ggccggccag     240
accgttgtcg acgtcaccaa cggcaagatc tttcgcctgt tggtcggcga cgagccgttc     300
gacgtccggt atggcgaatt gatctcccac gaacggatcc tcgacctgcg cgccgggacg     360
ctgacccgcc gcgcgcactg gcgctcaccg gcgggcaagc aagtcaaagt gacgtccacc     420
cggctggtgt cgctggccca ccgcagcgtc gcggcgatcg agtacgtcgt cgaggcaatc     480
gaggaattcg ttcgcgtgac cgtgcagtcc gaactcgtca ccaacgagga cgtaccggag     540
acctcggccg acccgcgggt gtcggccatc ctggacaggc cgctacaggc cgtcgagcac     600
gaacgcaccg agcggggtgc acttctcatg caccgcaccc gagccagcgc gctgatgatg     660
gccgcaggga tggaacacga ggtcgaggtt cccgggcggg tcgagatcac caccgacgcc     720
cgcccggacc tggcccgaac caccgtgatc tgcgggctgc gcccgggaca gaagctgcgc     780
```

-continued

| | |
|---|---|
| atcgtcaaat acctggccta tggctggtcc agcctgcgct cccgcccggc gctgcgcgac | 840 |
| caggccgccg gcgcgctgca cggtgcccgc tacagcggct ggcagggct gctggacgcg | 900 |
| caacgcgcct acctcgacga cttctgggac agcgcggacg tggaggtcga gggcgacccg | 960 |
| gaatgtcagc aagcggtgcg tttcgggtta tttcacctgt tgcaggccag cgcgcgcgcc | 1020 |
| gaacgccgcg cgatcccag caaggggctc accggaaccg ggtatgacgg ccacgccttt | 1080 |
| tgggacaccg aaggtttcgt gctaccggtg ctcacctaca ccgcaccgca tgcggtcgcc | 1140 |
| gacgcgctgc ggtggcgggc gtcgacgttg acctggcca aggagcgggc ggccgagctc | 1200 |
| ggcctggaag gtgccgcctt tccctggcgg accatccgcg acaggagtc ctcggcctac | 1260 |
| tggccggccg gcacgcggc ctggcacatc aacgccgaca tcgcgatggc gttcgagcgg | 1320 |
| taccgcatcg tcaccggcga cggttcgctg gaggaggaat gcggccttgc ggtgctgatc | 1380 |
| gagaccgccc ggctgtggct ctcgctcggg caccacgacc gccacggcgt ctggcacctc | 1440 |
| gacggggtca ccggtcccga cgagtacacg gcggtcgtcc gcgacaacgt gttcacgaat | 1500 |
| ctgatggcgg cgcacaatct gcacaccgcc gccgatgctt gcttgcgcca ccccgaggcg | 1560 |
| gcggaggcca tgggtgtcac caccgaggag atggccgcct ggcgcgacgc ggccgacgcc | 1620 |
| gccaacattc cctacgacga ggaactcggt gtccaccagc agtgtgaagg gttcaccacc | 1680 |
| cttgcggagt gggatttcga agccaacacc acttatccgt tgctactgca cgaggcctac | 1740 |
| gtgcgcttgt atcccgcaca ggtgatcaag caggccgacc tggtgctggc gatgcagtgg | 1800 |
| cagagtcacg cgttcacgcc cgagcagaag gcgcgcaacg tcgactacta cgaacggcgc | 1860 |
| atggtgcgcg actcgtcgtt gtcggcctgc actcaggcgg tgatgtgcgc cgaggtcggc | 1920 |
| catctcgagt tggcccacga ctatgcctac gaagccgccc tgatcgacct gcgcgacctg | 1980 |
| caccgcaaca cccgtgacgg cctacacatg gcttcgctgg ccggagcctg gacggcgctg | 2040 |
| gtcgtaggct tcggcggcct acgcgacgac gagggcatcc tgtccatcga tccgcagctg | 2100 |
| cccgacggca tctcgcggct gcggttccgg ctgcgatggc gcggcttccg gctgatcgtc | 2160 |
| gacgccaacc acaccgacgt cacccttcatc cttggcgacg gtcccggcac ccagctgacc | 2220 |
| atgcgccacg ccggccaaga tctgacgctg cacacggaca caccgtccac catcgccgtg | 2280 |
| cgcacccgta agccgctgct gccgccacca ccgcagccgc caggccgcga gccagtgcac | 2340 |
| cgccgggctt tagcccgg | 2358 |

<210> SEQ ID NO 129
<211> LENGTH: 786
<212> TYPE: DNA
<213> ORGANISM: Mycobacteria tuberculosis

<400> SEQUENCE: 129

| | |
|---|---|
| atggcgaact ggtatcgccc gaactatccg gaagtgaggt cccgcgtgct gggtctgccc | 60 |
| gagaaggtgc gtgcttgcct gttcgacctc gacggtgtgc tcaccgatac cgcgagcctg | 120 |
| cataccaagg cgtggaaggc catgtttgac gcctacctag ccgagcgagc cgagcgcacc | 180 |
| ggcgaaaaat tcgttcccctt cgaccctgcc gcggactatc acacgtatgt ggacggcaag | 240 |
| aaacgcgaag acggcgttcg atcgtttctg agcagccgcg ccatcgaaat acccgacggt | 300 |
| tccccggatg acccgggcgc cgccgagacg gtgtatggcc tgggcaaccg caagaacgac | 360 |
| atgttgcaca gctgctgcg cgacgatggg gcccaggtgt tcgacgggtc gcggcgctac | 420 |
| ctggaggcgg tcacggccgc gggtctcggt gtggccgtgg tgtcttcgag cgccaacacc | 480 |
| cgcgacgtgc tcgcgaccac cggtctggac cggttcgtcc agcagcgggt ggacggcgtg | 540 |

```
acgttgcgcg aagagcacat cgccggcaag ccggcccccg actccttcct gcgcgcggca    600
gaactgttgg gggttacccc cgacgcggcg gcggtgttcg aggacgccct gtccggggtg    660
gcggccggcc gcgccggcaa cttcgccgta gtggtgggca tcaaccgaac gggccgggcg    720
gctcaggccg cccagttgcg ccgccatggc gccgacgtgg tggtaaccga tctcgccgag    780
ctgctg                                                               786
```

<210> SEQ ID NO 130
<211> LENGTH: 60
<212> TYPE: DNA
<213> ORGANISM: M. tuberculosis
<220> FEATURE:
<221> NAME/KEY: misc_feature
<222> LOCATION: (1)...(60)
<223> OTHER INFORMATION: n = A,T,C or G

<400> SEQUENCE: 130

```
antagtaatg tgcgagctga gcgatgtcgc cgctcccaaa aattaccaat ggttnggtca    60
```

<210> SEQ ID NO 131
<211> LENGTH: 60
<212> TYPE: DNA
<213> ORGANISM: M. tuberculosis

<400> SEQUENCE: 131

```
agtagtaatg tgcgagctga gcgatgtcgc cgctcccaaa aattaccaat ggtttggtca    60
```

<210> SEQ ID NO 132
<211> LENGTH: 60
<212> TYPE: DNA
<213> ORGANISM: M. tuberbulosis

<400> SEQUENCE: 132

```
tgacgccttc ctaaccagaa ttgtgaattc atacaagccg tagtcgtgca gaagcgcaac    60
```

<210> SEQ ID NO 133
<211> LENGTH: 60
<212> TYPE: DNA
<213> ORGANISM: M. tuberculosis

<400> SEQUENCE: 133

```
tgacgccttc ctaaccagaa ttgtgaattc atacaagccg tagtcgtgca gaagcgcaac    60
```

<210> SEQ ID NO 134
<211> LENGTH: 11
<212> TYPE: DNA
<213> ORGANISM: M. tuberculosis

<400> SEQUENCE: 134

```
actcttggag t                                                         11
```

<210> SEQ ID NO 135
<211> LENGTH: 11
<212> TYPE: DNA
<213> ORGANISM: M. tuberculosis

<400> SEQUENCE: 135

```
actcttggag t                                                         11
```

<210> SEQ ID NO 136
<211> LENGTH: 49
<212> TYPE: DNA

-continued

```
<213> ORGANISM: M. tuberculosis
<220> FEATURE:
<221> NAME/KEY: misc_feature
<222> LOCATION: (1)...(49)
<223> OTHER INFORMATION: n = A,T,C or G

<400> SEQUENCE: 136
gtggcctaca acggngctct ccgnggcgcg ggcgtaccgg atatcttag            49

<210> SEQ ID NO 137
<211> LENGTH: 49
<212> TYPE: DNA
<213> ORGANISM: M. tuberculosis

<400> SEQUENCE: 137
gcggcctaca acggcgctct ccgcggcgcg ggcgtaccgg atatcttag            49
```

MOLECULAR DIFFERENCES BETWEEN SPECIES OF THE *M. TUBERCULOSIS* COMPLEX

This application claims the benefit of U.S. Provisional Application No. 60/097,936, filed Aug. 25, 1998.

Tuberculosis is an ancient human scourge that continues to be an important public health problem worldwide. It is an ongoing epidemic of staggering proportions. Approximately one in every three people in the world is infected with *Mycobacterium tuberculosis*, and has a 10% lifetime risk of progressing from infection to clinical disease. Although tuberculosis can be treated, an estimated 2.9 million people died from the disease last year.

There are significant problems with a reliance on drug treatment to control active *M. tuberculosis* infections. Most of the regions having high infection rates are less developed countries, which suffer from a lack of easily accessible health services, diagnostic facilities and suitable antibiotics against *M. tuberculosis*. Even where these are available, patient compliance is often poor because of the lengthy regimen required for complete treatment, and multidrug-resistant strains are increasingly common.

Prevention of infection would circumvent the problems of treatment, and so vaccination against tuberculosis is widely performed in endemic regions. Around 100 million people a year are vaccinated with live bacillus Calmette-Guerin (BCG) vaccine. BCG has the great advantage of being inexpensive and easily administered under less than optimal circumstances, with few adverse reactions. Unfortunately, the vaccine is widely variable in its efficacy, providing anywhere from 0 to 80% protection against infection with *M. tuberculosis*.

BCG has an interesting history. It is an attenuated strain of *M. bovis*, a very close relative of *M. tuberculosis*. The *M. bovis* strain that became BCG was isolated from a cow in the late 1800's by a bacteriologist named Nocard, hence it was called Nocard's bacillus. The attenuation of Nocard's bacillus took place from 1908 to 1921, over the course of 230 in vitro passages. Thereafter, it was widely grown throughout the world, resulting in additional hundreds and sometime thousands of in vitro passages. Throughout its many years in the laboratory, there has been selection for cross-reaction with the tuberculin skin test, and for decreased side effects. The net result has been a substantially weakened pathogen, which may be ineffective in raising an adequate immune response.

New antituberculosis vaccines are urgently needed for the general population in endemic regions, for HIV-infected individuals, as well as health care professionals likely to be exposed to tubercle bacilli. Recombinant DNA vaccines bearing protective genes from virulent *M. tuberculosis* are being developed using shuttle plasmids to transfer genetic material from one mycobacterial species to another, for example see U.S. Pat. No. 5,776,465. Tuberculosis vaccine development should be given a high priority in current medical research goals.

Relevant literature

Mahairas et al. (1996) *J Bacteriol* 178(5):1274–1282 provides a molecular analysis of genetic differences between *Mycobacterium bovis* BCG and virulent *M. bovis*. Subtractive genomic hybridization was used to identify genetic differences between virulent *M. bovis* and *M. tuberculosis* and avirulent BCG. U.S. Pat. No. 5,700,683 is directed to these genetic differences.

Cole et al. (1998) *Nature* 393:537–544 have described the complete genome of *M. tuberculosis*. To obtain the contiguous genome sequence, a combined approach was used that involved the systematic sequence analysis of selected large-insert clones as well as random small-insert clones from a whole-genome shotgun library. This culminated in a composite sequence of 4,411,529 base pairs, with a G+C content of 65.6%. 3,924 open reading frames were identified in the genome, accounting for ~91% of the potential coding capacity.

*Mycobacterium tuberculosis* (M.tb.) genomic sequence is available at several internet sites.

SUMMARY OF THE INVENTION

Genetic markers are provided that distinguish between strains of the *Mycobacterium tuberculosis* complex, particularly between avirulent and virulent strains. Strains of interest include *M. bovis*, *M. bovis* BCG strains, *M. tuberculosis* (*M. tb.*) isolates, and bacteriophages that infect mycobacteria. The genetic markers are used for assays, e.g. immunoassays, that distinguish between strains, such as to differentiate between BCG immunization and *M. tb.* infection. The protein products may be produced and used as an immunogen, in drug screening, etc. The markers are useful in constructing genetically modified *M. tb* or *M. bovis* cells having improved vaccine characteristics.

DETAILED DESCRIPTION OF THE EMBODIMENTS

Specific genetic deletions are identified that serve as markers to distinguish between avirulent and virulent mycobacteria strains, including *M. bovis*, *M. bovis* BCG strains, *M. tuberculosis* (*M. tb.*) isolates, and bacteriophages that infect mycobacteria. These deletions are used as genetic markers to distinguish between the different mycobacteria. The deletions may be introduced into *M. tb.* or *M. bovis* by recombinant methods in order to render a pathogenic strain avirulent. Alternatively, the deleted genes are identified in the *M. tb.* genome sequence, and are then reintroduced by recombinant methods into BCG or other vaccine strains, in order to improve the efficacy of vaccination.

The deletions of the invention are identified by comparative DNA hybridizations from genomic sequence of mycobacterium to a DNA microarray comprising representative sequences of the *M. tb.* coding sequences. The deletions are then mapped to the known *M. tb.* genome sequence in order to specifically identify the deleted gene(s), and to characterize nucleotide sequence of the deleted region.

Nucleic acids comprising the provided deletions and junctions are used in a variety of applications. Hybridization probes may be obtained from the known *M. tb.* sequence which correspond to the deleted sequences. Such probes are useful in distinguishing between mycobacteria. For example, there is a 10% probability that an *M. tb.* infected person will progress to clinical disease, but that probability may vary depending of the particular infecting strain. Analysis for the presence or absence of the deletions provided below as "M. tb variable" is used to distinguish between different *M. tb* strains. The deletions are also useful in identifying whether a patient that is positive for a tuberculin skin test has been infected with *M. tb* or with BCG.

In another embodiment of the invention, mycobacteria are genetically altered to delete sequences identified herein as absent in attenuated strains, but present in pathogenic strains, e.g. deletions found in BCG but present in *M. tb* H37Rv. Such genetically engineered strains may provide superior vaccines to the present BCG isolates in use. Alternatively, BCG strains may be "reconstructed" to more closely resemble wild-type *M. tb* by inserting certain of the deleted sequences back into the genome. Since the protein products of the deleted sequences are expressed in virulent mycobacterial species, the encoded proteins are useful as immunogens for vaccination.

The attenuation (loss of virulence) in BCG is attributed to the loss of genetic material at a number of places throughout the genome. The selection over time for fewer side-effects resulting from BCG immunization, while retaining cross-reactivity with the tuberculin skin test, has provided an excellent screen for those sequences that engender side effects. The identification of deletions that vary between BCG isolates identifies such sequences, which may be used in drug screening and biological analysis for the role of the deleted genes in causing untoward side effects and pathogenicity.

Identification of *M. Tuberculosis* Complex Deletion Markers

The present invention provides nucleic acid sequences that are markers for specific mycobacteria, including *M. tb., M. bovis*, BCG and bacteriophage. The deletions are listed in Table 1. The absence or presence of these marker sequences is characteristic of the indicated isolate, or strain. As such, they provide a unique characteristic for the identification of the indicated mycobacteria. The deletions are identified by their *M. tb.* open reading frame ("Rv" nomenclature), which corresponds to a known genetic sequence, and may be accessed as previously cited. The junctions of the deletions are provided by the designation of position in the publicly available *M. tb.* sequence.

TABLE 1

| SEQ ID | rd | rv_num | orf_id | breakpoint |
|---|---|---|---|---|
| SEQ ID NO: 1 | RD01 | Rv3871 | MTV027.06 | "H37Rv, segment 160: 7534, 16989" |
| SEQ ID NO: 2 | RD01 | Rv3872 | MTV027.07 | "H37Rv, segment 160: 7534, 16989" |
| SEQ ID NO: 3 | RD01 | Rv3873 | MTV027.08 | "H37Rv, segment 160: 7534, 16989" |
| SEQ ID NO: 4 | RD01 | Rv3874 | MTV027.09 | "H37Rv, segment 160: 7534, 16989" |
| SEQ ID NO: 5 | RD01 | Rv3875 | MTV027.10 | "H37Rv, segment 160: 7534, 16989" |
| SEQ ID NO: 6 | RD01 | Rv3876 | MTV027.11 | "H37Rv, segment 160: 7534, 16989" |
| SEQ ID NO: 7 | RD01 | Rv3877 | MTV027.12 | "H37Rv, segment 160: 7534, 16989" |
| SEQ ID NO: 8 | RD01 | Rv3878 | MTV027.13 | "H37Rv, segment 160: 7534, 16989" |
| SEQ ID NO: 9 | RD01 | Rv3879c | MTV027.14c | "H37Rv, segment 160: 7534, 16989" |
| SEQ ID NO: 10 | RD02 | Rv1988 | MTCY39.31c | "H37Rv segment 88: 14211, segment 89: 8598" |
| SEQ ID NO: 11 | RD02 | Rv1987 | MTCY39.32c | "H37Rv segment 88: 14211, segment 89: 8598" |
| SEQ ID NO: 12 | RD02 | Rv1986 | MTCY39.33c | "H37Rv segment 88: 14211, segment 89: 8598" |
| SEQ ID NO: 13 | RD02 | Rv1985c | MTCY39.34 | "H37Rv segment 88: 14211, segment 89: 8598" |
| SEQ ID NO: 14 | RD02 | Rv1984c | MTCY39.35 | "H37Rv segment 88: 14211, segment 89: 8598" |
| SEQ ID NO: 15 | RD02 | Rv1983 | MTCY39.36c | "H37Rv segment 88: 14211, segment 89: 8598" |
| SEQ ID NO: 16 | RD02 | Rv1982c | MTCY39.37 | "H37Rv segment 88: 14211, segment 89: 8598" |
| SEQ ID NO: 17 | RD02 | Rv1981c | MTCY39.38 | "H37Rv segment 88: 14211, segment 89: 8598" |
| SEQ ID NO: 18 | RD02 | Rv1980c | MTCY39.39 | "H37Rv segment 88: 14211, segment 89: 8598" |
| SEQ ID NO: 19 | RD02 | Rv1979c | MTCY39.40 | "H37Rv segment 88: 14211, segment 89: 8598" |
| SEQ ID NO: 20 | RD02 | Rv1978 | MTV051.16 | "H37Rv segment 88: 14211, segment 89: 8598" |
| SEQ ID NO: 21 | RD03 | Rv1586c | MTCY336.18 | "H37Rv, segment 70: 7677, 16923" |
| SEQ ID NO: 22 | RD03 | Rv1585c | MTCY336.19 | "H37Rv, segment 70: 7677, 16923" |
| SEQ ID NO: 23 | RD03 | Rv1584c | MTCY336.20 | "H37Rv, segment 70: 7677, 16923" |
| SEQ ID NO: 24 | RD03 | Rv1583c | MTCY336.21 | "H37Rv, segment 70: 7677, 16923" |
| SEQ ID NO: 25 | RD03 | Rv1582c | MTCY336.22 | "H37Rv, segment 70: 7677, 16923" |
| SEQ ID NO: 26 | RD03 | Rv1581c | MTCY336.23 | "H37Rv, segment 70: 7677, 16923" |
| SEQ ID NO: 27 | RD03 | Rv1580c | MTCY336.24 | "H37Rv, segment 70: 7677, 16923" |
| SEQ ID NO: 28 | RD03 | Rv1579c | MTCY336.25 | "H37Rv, segment 70: 7677, 16923" |
| SEQ ID NO: 29 | RD03 | Rv1578c | MTCY336.26 | "H37Rv, segment 70: 7677, 16923" |
| SEQ ID NO: 30 | RD03 | Rv1577c | MTCY336.27 | "H37Rv, segment 70: 7677, 16923" |
| SEQ ID NO: 31 | RD03 | Rv1576c | MTCY336.28 | "H37Rv, segment 70: 7677, 16923" |
| SEQ ID NO: 32 | RD03 | Rv1575 | MTCY336.29c | "H37Rv, segment 70: 7677, 16923" |
| SEQ ID NO: 33 | RD03 | Rv1574 | MTCY336.30c | "H37Rv, segment 70: 7677, 16923" |
| SEQ ID NO: 34 | RD03 | Rv1573 | MTCY336.31c | "H37Rv, segment 70: 7677, 16923" |
| SEQ ID NO: 35 | RD04 | Rv0221 | MTCY08D5.16 | "H37Rv, segment 12: 17432, 19335" |
| SEQ ID NO: 36 | RD04 | Rv0222 | MTCY08D5.17 | "H37Rv, segment 12: 17432, 19335" |
| SEQ ID NO: 37 | RD04 | Rv0223c | MTCY08D5.18 | "H37Rv, segment 12: 17432, 19335" |
| SEQ ID NO: 38 | RD05 | Rv3117 | MTCY164.27 | "H37Rv, segment 135: 27437, 30212" |
| SEQ ID NO: 39 | RD05 | Rv3118 | MTCY164.28 | "H37Rv, segment 135: 27437, 30212" |
| SEQ ID NO: 40 | RD05 | Rv3119 | MTCY164.29 | "H37Rv, segment 135: 27437, 30212" |
| SEQ ID NO: 41 | RD05 | Rv3120 | MTCY164.30 | "H37Rv, segment 135: 27437, 30212" |
| SEQ ID NO: 42 | RD05 | Rv3121 | MTCY164.31 | "H37Rv, segment 135: 27437, 30212" |
| SEQ ID NO: 43 | RD06 | Rv1506c | MTCY277.28c | "H37Rv, segment 65: 23614, 36347" |
| SEQ ID NO: 44 | RD06 | Rv1507c | MTCY277.29c | "H37Rv, segment 65: 23614, 36347" |
| SEQ ID NO: 45 | RD06 | Rv1508c | MTCY277.30c | "H37Rv, segment 65: 23614, 36347" |
| SEQ ID NO: 46 | RD06 | Rv1509 | MTCY277.31 | "H37Rv, segment 65: 23614, 36347" |
| SEQ ID NO: 47 | RD06 | Rv1510 | MTCY277.32 | "H37Rv, segment 65: 23614, 36347" |
| SEQ ID NO: 48 | RD06 | Rv1511 | MTCY277.33 | "H37Rv, segment 65: 23614, 36347" |
| SEQ ID NO: 49 | RD06 | Rv1512 | MTCY277.34 | "H37Rv, segment 65: 23614, 36347" |
| SEQ ID NO: 50 | RD06 | Rv1513 | MTCY277.35 | "H37Rv, segment 65: 23614, 36347" |
| SEQ ID NO: 51 | RD06 | Rv1514c | MTCY277.36c | "H37Rv, segment 65: 23614, 36347" |
| | RD06 | Rv1515c | MTCY277.37c | "H37Rv, segment |

TABLE 1-continued

| SEQ ID | rd | rv_num | orf_id | breakpoint |
|---|---|---|---|---|
| SEQ ID NO: 53 | RD06 | Rv1516c | MTCY277.38c | "H37Rv, segment 65: 23614, 36347" |
| SEQ ID NO: 54 | RD07 | Rv2346c | MTCY98.15c | "H37Rv, segment 103: 17622, 26584" |
| SEQ ID NO: 55 | RD07 | Rv2347c | MTCY98.16c | "H37Rv, segment 103: 17622, 26584" |
| SEQ ID NO: 56 | RD07 | Rv2348c | MTCY98.17c | "H37Rv, segment 103: 17622, 26584" |
| SEQ ID NO: 57 | RD07 | Rv2349c | MTCY98.18c | "H37Rv, segment 103: 17622, 26584" |
| SEQ ID NO: 58 | RD07 | Rv2350c | MTCY98.19c | "H37Rv, segment 103: 17622, 26584" |
| SEQ ID NO: 59 | RD07 | Rv2351c | MTCY98.20c | "H37Rv, segment 103: 17622, 26584" |
| SEQ ID NO: 60 | RD07 | Rv2352c | MTCY98.21c | "H37Rv, segment 103: 17622, 26584" |
| SEQ ID NO: 61 | RD07 | Rv2353c | MTCY98.22c | "H37Rv, segment 103: 17622, 26584" |
| SEQ ID NO: 62 | RD08 | Rv0309 | MTCY63.14 | "H37Rv, segment 16: 17018, 20446" |
| SEQ ID NO: 63 | RD08 | Rv0310c | MTCY63.15c | "H37Rv, segment 16: 17018, 20446" |
| SEQ ID NO: 64 | RD08 | Rv0311 | MTCY63.16 | "H37Rv, segment 16: 17018, 20446" |
| SEQ ID NO: 65 | RD08 | Rv0312 | MTCY63.17 | "H37Rv, segment 16: 17018, 20446" |
| SEQ ID NO: 66 | RD09 | Rv3623 | MTCY15C10.29c | "H37Rv, segment 153: 21131, segment 154: 2832" |
| SEQ ID NO: 67 | RD09 | Rv3622c | MTCY15C10.30 | "H37Rv, segment 153: 21131, segment 154: 2832" |
| SEQ ID NO: 68 | RD09 | Rv3621c | MTCY15C10.31 | "H37Rv, segment 153: 21131, segment 154: 2832" |
| SEQ ID NO: 69 | RD09 | Rv3620c | MTCY15C10.32 | "H37Rv, segment 153: 21131, segment 154: 2832" |
| SEQ ID NO: 70 | RD09 | Rv3619c | MTCY15C10.33 | "H37Rv, segment 153: 21131, segment 154: 2832" |
| SEQ ID NO: 71 | RD09 | Rv3618 | MTCY15C10.34c | "H37Rv, segment 153: 21131, segment 154: 2832" |
| SEQ ID NO: 72 | RD09 | Rv3617 | MTCY15C10.35c | "H37Rv, segment 153: 21131, segment 154: 2832" |
| SEQ ID NO: 73 | RD10 | Rv1257c | MTCY50.25 | "H37Rv, segment 55: 3689, 6696" |
| SEQ ID NO: 74 | RD10 | Rv1256c | MTCY50.26 | "H37Rv, segment 55: 3689, 6696" |
| SEQ ID NO: 75 | RD10 | Rv1255c | MTCY50.27 | "H37Rv, segment 55: 3689, 6696" |
| SEQ ID NO: 76 | RD11 | Rv3429 | MTCY77.01 | "H37Rv, segment 145: 30303 to segment 146: 1475" |
| SEQ ID NO: 77 | RD11 | Rv3428c | MTCY78.01 | "H37Rv, segment 145: 30303 to segment 146: 1475" |
| SEQ ID NO: 78 | RD11 | Rv3427c | MTCY78.02 | "H37Rv, segment 145: 30303 to segment 146: 1475" |
| SEQ ID NO: 79 | RD11 | Rv3426 | MTCY78.03c | "H37Rv, segment 145: 30303 to segment 146: 1475" |
| SEQ ID NO: 80 | RD11 | Rv3425 | MTCY78.04c | "H37Rv, segment 145: 30303 to segment 146: 1475" |
| SEQ ID NO: 81 | RD12 | Rv2072c | MTCY49.11c | "H37Rv segment 93: 9301, 11331" |
| SEQ ID NO: 82 | RD12 | Rv2073c | MTCY49.12c | "H37Rv segment 93: 9301, 11331" |
| SEQ ID NO: 83 | RD12 | Rv2074 | MTCY49.13 | "H37Rv segment 93: 9301, 11331" |
| SEQ ID NO: 84 | RD12 | Rv2075c | MTCY49.14c | "H37Rv segment 93: 9301, 11331" |
| SEQ ID NO: 85 | RD13bis | Rv2645 | MTCY441.15 | "H37Rv segment 118: 12475, 23455" |
| SEQ ID NO: 86 | RD13bis | Rv2646 | MTCY441.16 | "H37Rv segment 118: 12475, 23455" |
| SEQ ID NO: 87 | RD13bis | Rv2647 | MTCY441.17 | "H37Rv segment 118: 12475, 23455" |
| SEQ ID NO: 88 | RD13bis | Rv2648 | MTCY441.17A | "H37Rv segment 118: 12475, 23455" |
| SEQ ID NO: 89 | RD13bis | Rv2649 | MTCY441.18 | "H37Rv segment 118: 12475, 23455" |
| SEQ ID NO: 90 | RD13bis | Rv2650c | MTCY441.19 | "H37Rv segment 118: 12475, 23455" |
| SEQ ID NO: 91 | RD13bis | Rv2651c | MTCY441.20c | "H37Rv segment 118: 12475, 23455" |
| SEQ ID NO: 92 | RD13bis | Rv2652c | MTCY441.21c | "H37Rv segment 118: 12475, 23455" |
| SEQ ID NO: 93 | RD13bis | Rv2653c | MTCY441.22c | "H37Rv segment 118: 12475, 23455" |
| SEQ ID NO: 94 | RD13bis | Rv2654c | MTCY441.23c | "H37Rv segment 118: 12475, 23455" |
| SEQ ID NO: 95 | RD13bis | Rv2655c | MTCY441.24c | "H37Rv segment 118: 12475, 23455" |
| SEQ ID NO: 96 | RD13bis | Rv2656c | MTCY441.25c | "H37Rv segment 118: 12475, 23455" |
| SEQ ID NO: 97 | RD13bis | Rv2657c | MTCY441.26c | "H37Rv segment 118: 12475, 23455" |
| SEQ ID NO: 98 | RD13bis | Rv2658c | MTCY441.27c | "H37Rv segment 118: 12475, 23455" |
| SEQ ID NO: 99 | RD13bis | Rv2659c | MTCY441.28c | "H37Rv segment 118: 12475, 23455" |
| SEQ ID NO: 100 | RD13bis | Rv2660c | MTCY441.29c | "H37Rv segment 118: 12475, 23455" |
| SEQ ID NO: 101 | RD14 | Rv1766 | MTCY28.32 | "H37Rv, segment 79: 30573, 39642" |
| SEQ ID NO: 102 | RD14 | Rv1767 | MTCY28.33 | "H37Rv, segment 79: 30573, 39642" |
| SEQ ID NO: 103 | RD14 | Rv1768 | MTCY28.34 | "H37Rv, segment 79: 30573, 39642" |
| SEQ ID NO: 104 | RD14 | Rv1769 | MTCY28.35 | "H37Rv, segment 79: 30573, 39642" |
| SEQ ID NO: 105 | RD14 | Rv1770 | MTCY28.36 | "H37Rv, segment 79: 30573, 39642" |
| SEQ ID NO: 106 | RD14 | Rv1771 | MTCY28.37 | "H37Rv, segment 79: 30573, 39642" |
| SEQ ID NO: 107 | RD14 | Rv1772 | MTCY28.38 | "H37Rv, segment 79: 30573, 39642" |
| SEQ ID NO: 108 | RD14 | Rv1773c | MTCY28.39 | "H37Rv, segment 79: 30573, 39642" |
| SEQ ID NO: 109 | RD15 | Rv1763c | MTV051.01c | "H37Rv, segment 88: 1153, 13873" |
| SEQ ID NO: 110 | RD15 | Rv1764 | MTV051.02 | "H37Rv, segment 88: 1153, 13873" |
| SEQ ID NO: 111 | RD15 | Rv1765 | MTV051.03 | "H37Rv, segment 88: 1153, 13873" |
| SEQ ID NO: 112 | RD15 | Rv1766 | MTV051.04 | "H37Rv, segment 88: 1153, 13873" |
| SEQ ID NO: 113 | RD15 | Rv1767 | MTV051.05 | "H37Rv, segment 88: 1153, 13873" |
| SEQ ID NO: 114 | RD15 | Rv1768 | MTV051.06 | "H37Rv, segment 88: 1153, 13873" |
| SEQ ID NO: | RD15 | Rv1769 | MTV051.07 | "H37Rv, segment 88: 1153, 13873" |

TABLE 1-continued

| SEQ ID | rd | rv_num | orf_id | breakpoint |
|---|---|---|---|---|
| SEQ ID NO: 115 | | | | |
| SEQ ID NO: 116 | RD15 | Rv1770 | MTV051.08 | "H37Rv, segment 88: 1153, 13873" |
| SEQ ID NO: 117 | RD15 | Rv1771 | MTV051.09 | "H37Rv, segment 88: 1153, 13873" |
| SEQ ID NO: 118 | RD15 | Rv1772 | MTV051.10 | "H37Rv, segment 88: 1153, 13873" |
| SEQ ID NO: 119 | RD15 | Rv1773 | MTV051.11 | "H37Rv, segment 88: 1153, 13873" |
| SEQ ID NO: 120 | RD15 | Rv1774 | MTV051.12 | "H37Rv, segment 88: 1153, 13873" |
| SEQ ID NO: 121 | RD15 | Rv1775 | MTV051.13 | "H37Rv, segment 88: 1153, 13873" |
| SEQ ID NO: 122 | RD15 | Rv1776c | MTV051.14 | "H37Rv, segment 88: 1153, 13873" |
| SEQ ID NO: 123 | RD15 | Rv1777 | MTV051.15 | "H37Rv, segment 88: 1153, 13873" |
| SEQ ID NO: 124 | RD16 | Rv3405c | MTCY78.23 | "H37Rv, segment 145: 5012, 12621" |
| SEQ ID NO: 125 | RD16 | Rv3404c | MTCY78.24 | "H37Rv, segment 145: 5012, 12621" |
| SEQ ID NO: 126 | RD16 | Rv3403c | MTCY78.25 | "H37Rv, segment 145: 5012, 12621" |
| SEQ ID NO: 127 | RD16 | Rv3402c | MTCY78.26 | "H37Rv, segment 145: 5012, 12621" |
| SEQ ID NO: 128 | RD16 | Rv3401 | MTCY78.27c | "H37Rv, segment 145: 5012, 12621" |
| SEQ ID NO: 129 | RD16 | Rv3400 | MTCY78.28c | "H37Rv, segment 145: 5012, 12621" |

The "Rv" column indicates public *M. tb* sequence, open reading frame. The BCG

TABLE 2

Strains employed in study of BCG phylogeny

| Name of strain | Synonym | Source | Descriptors |
|---|---|---|---|
| BCG-Russia | Moscow | ATCC | # 35740 |
| BCG-Moreau | Brazil | ATCC | # 35736 |
| BCG-Moreau | Brazil | IAF | dated 1958 |
| BCG-Moreau | Brazil | IAF | dated 1961 |
| BCG-Japan | Tokyo | ATCC | # 35737 |
| BCG-Japan | Tokyo | IAF | dated 1961 |
| BCG-Japan | Tokyo | JATA | vaccine strain |
| BCG-Japan | Tokyo | JATA | bladder cancer strain |
| BCG-Japan | Tokyo | JATA | clinical isolate-adenitis |
| BCG-Sweden | Gothenburg | ATCC | # 35732 |
| BCG-Sweden | Gothenburg | IAF | dated 1958 |
| BCG-Sweden | Gothenburg | SSI | production lot, Copenhagen |
| BCG-Phipps | Philadelphia | ATCC | # 35744 |
| BCG-Denmark | Danish 1331 | ATCC | # 35733 |
| BCG-Copenhagen | | ATCC | # 27290 |
| BCG-Copenhagen | | IAF | dated 1961 |
| BCG-Tice | Chicago | vaccine | dated 1973 |
| BCG-Tice | Chicago | ATCC | # 35743 |
| BCG-Frappier | Montreal | IAF | primary lot, 1973 |
| BCG-Frappier, INH-resistant | Montreal-R | IAF | primary lot, 1973 |
| BCG-Frappier | Montreal | IAF | passage 946 |
| BCG-Connaught | Toronto | CL | bladder cancer treatment |
| BCG-Birkhaug | | ATCC | # 35731 |
| BCG-Prague | Czech | SSI | lyophilized 1968 |
| BCG-Glaxo | | vaccine | dated 1973 |
| BCG-Glaxo | | ATCC | # 35741 |
| BCG-Pasteur | | IAF | passage 888 |
| BCG-Pasteur | | IAF | dated 1961 |
| BCG-Pasteur | | IP | 1173P2-B |
| BCG-Pasteur | | IP | 1173P2-C |
| BCG-Pasteur | | IP | clinical isolate # 1 |
| BCG-Pasteur | | IP | clinical isolate # 2 |
| BCG-Pasteur | | ATCC | # 35734 |

Abbreviations:
IP = Institut Pasteur, Paris, France;
IAF = Institut Armand Frappier, Laval, Canada;
AT = American Type Culture Collection, Rockville, Md, USA;
SSI = Statens Serum Institute, Copenhagen, Denmark;
CL = Connaught Laboratories, Willowdale, Canada,
JATA = Japanese Anti-Tuberculosis Association;
INH = isoniazid.
Canadian: BCG's refers to BCG-Montreal and BCG-Toronto, the latter being derived from the former.

In performing the initial screening method, genomic DNA is isolated from two mycobacteria microbial cell cultures. The two DNA preparations are labeled, where a different label is used for the first and second microbial cultures, typically using nucleotides conjugated to a fluorochrome that emits at a wavelength substantially different from that of the fluorochrome tagged nucleotides used to label the selected probe. The strains used were the reference strain of *Mycobacterium tuberculosis* (H37Rv), other *M. tb.* laboratory strains, such as H37Ra, the O strain, *M. tb.* clinical isolates, the reference strain of *Mycobacterium bovis,* and different strains of *Mycobacterium bovis* BCG.

The two DNA preparations are mixed, and competitive hybridization is carried out to a microarray representing all of the open reading frames in the genome of the test microbe, usually H37Rv. Hybridization of the labeled sequences is accomplished according to methods well known in the art. In a preferred embodiment, the two probes are combined to provide for a competitive hybridization to a single microarray. Hybridization can be carried out under conditions varying in stringency, preferably under conditions of high stringency (e.g., 4×SSC, 10% SDS, 65° C.) to allow for hybridization of complementary sequences having extensive homology (e.g., having at least 85% sequence identity, preferably at least 90% sequence identity, more preferably having at least 95% sequence identity). Where the target sequences are native sequences the hybridization is preferably carried out under conditions that allow hybridization of only highly homologous sequences (e.g., at least 95% to 100% sequence identity).

Two color fluorescent hybridization is utilized to assay the representation of the unselected library in relation to the selected library (i.e., to detect hybridization of the unselected probe relative to the selected probe). From the ratio of one color to the other, for any particular array element, the relative abundance of that sequence in the unselected and selected libraries can be determined. In addition, comparison of the hybridization of the selected and unselected probes provides an internal control for the assay. An absence of signal from the reference strain, as compared to H37Rv, is indicative that the open reading frame is deleted in the test strain. The deletion may be further mapped by Southern blot analysis, and by sequencing the regions flanking the deletion.

Microarrays can be scanned to detect hybridization of the selected and the unselected sequences using a custom built scanning laser microscope as described in Shalon et al., *Genome Res.* 6:639 (1996). A separate scan, using the appropriate excitation line, is performed for each of the two fluorophores used. The digital images generated from the scan are then combined for subsequent analysis. For any particular array element, the ratio of the fluorescent signal from the amplified selected cell population DNA is compared to the fluorescent signal from the unselected cell population DNA, and the relative abundance of that sequence in the selected and unselected libraries determined.

Nucleic Acid Compositions

As used herein, the term "deletion marker", or "marker" is used to refer to those sequences of *M. tuberculosis* complex genomes that are deleted in one or more of the strains or species, as indicated in Table 1. The bacteria of the *M. tuberculosis* complex include *M. tuberculosis, M. bovis*, and BCG, inclusive of varied isolates and strains within each species. Nucleic acids of interest include all or a portion of the deleted region, particularly complete open reading frames, hybridization primers, promoter regions, etc.

The term "junction " or "deletion junction " is used to refer to nucleic acids that comprise the regions on both the 3' and the 5' sequence immediately flanking the deletion. Such junction sequences are preferably used as short primers, e.g. from about 15 nt to about 30 nt, that specifically hybridize to the junction, but not to a nucleic acid comprising the undeleted genomic sequence. For example, the deletion found in *M. bovis*, at Rv0221, corresponds to the nucleotide sequence of the *M. tuberculosis* H37Rv genome, segment 12: 17432,19335. The junction comprises the regions upstream of position 17342, and downstream of 19335, e.g. a nucleic acid of 20 nucleotides comprising the sequence from H37Rv 17332–17342 joined to 19335–19345.

Typically, such nucleic acids comprising a junction will include at least about 7 nucleotides from each flanking region, i.e. from the 3' and from the 5' sequence adjacent to the deletion, and may be about 10 nucleotides from each flanking region, up to about 15 nucleotides, or more. Amplification primers that hybridize to the junction sequence, to the deleted sequence, and to the flanking non-deleted regions have a variety of uses, as detailed below.

The nucleic acid compositions of the subject invention encode all or a part of the deletion markers. Fragments may be obtained of the DNA sequence by chemically synthesizing oligonucleotides in accordance with conventional methods, by restriction enzyme digestion, by PCR amplification, etc. For the most part, DNA fragments will be at least about 25 nt in length, usually at least about 30 nt, more usually at least about 50 nt. For use in amplification reactions, such as PCR, a pair of primers will be used. The exact composition of the primer sequences is not critical to the invention, but for most applications the primers will hybridize to the is subject sequence under stringent conditions, as known in the art. It is preferable to chose a pair of primers that will generate an amplification product of at least about 50 nt, preferably at least about 100 nt. Algorithms for the selection of primer sequences are generally known, and are available in commercial software packages. Amplification primers hybridize to complementary strands of DNA, and will prime towards each other.

Usually, the DNA will be obtained substantially free of other nucleic acid sequences that do not include a deletion marker sequence or fragment thereof, generally being at least about 50%, usually at least about 90% pure and are typically "recombinant", i.e. flanked by one or more nucleotides with which it is not normally associated on a naturally occurring chromosome.

For screening purposes, hybridization probes of one or more of the deletion sequences may be used in separate reactions or spatially separated on a solid phase matrix, or labeled such that they can be distinguished from each other. Assays may utilize nucleic acids that hybridize to one or more of the described deletions.

An array may include all or a subset of the deletion markers listed in Table 1. Usually such an array will include at least 2 different deletion marker sequences, ie. deletions located at unique positions within the locus, and may include all of the provided deletion markers. Arrays of interest may further comprise other genetic sequences, particularly other sequences of interest for tuberculosis screening. The oligonucleotide sequence on the array will usually be at least about 12 nt in length, may be the length of the provided deletion marker sequences, or may extend into the flanking regions to generate fragments of 100 to 200 nt in length. For examples of arrays, see Ramsay (1998) *Nat. Biotech.* 16:40–44; Hacia et al. (1996) *Nature Genetics* 14:441–447; Lockhart et al. (1996) *Nature Biotechnol.* 14:1675–1680; and De Risi et al. (1996) *Nature Genetics* 14:457–460.

Nucleic acids may be naturally occurring, e.g. DNA or RNA, or may be synthetic analogs, as known in the art. Such analogs may be preferred for use as probes because of superior stability under assay conditions. Modifications in the native structure, including alterations in the backbone, sugars or heterocyclic bases, have been shown to increase intracellular stability and binding affinity. Among useful changes in the backbone chemistry are phosphorothioates; phosphorodithioates, where both of the non-bridging oxygens are substituted with sulfur; phosphoroamidites; alkyl phosphotriesters and boranophosphates. Achiral phosphate derivatives include 3'-O'-5'S-phosphorothioate, 3'-S-5'-O-phosphorothioate, 3'-$CH_2$-5'-O-phosphonate and 3'-NH-5'-O-phosphoroamidate Peptide nucleic acids replace the entire ribose phosphodiester backbone with a peptide linkage.

Sugar modifications are also used to enhance stability and affinity. The α-anomer of deoxyribose may be used, where the base is inverted with respect to the natural b-anomer. The 2'-OH of the ribose sugar may be altered to form 2'-O-methyl or 2'-O-allyl sugars, which provide resistance to degradation without comprising affinity.

Modification of the heterocyclic bases must maintain proper base pairing. Some useful substitutions include deoxyuridine for deoxythymidine; 5-methyl-2'-deoxycytidine and 5-bromo-2'-deoxycytidine for deoxycytidine. 5-propynyl-2'-deoxyuridine and 5-propynyl-2'-deoxycytidine have been shown to increase affinity and biological activity when substituted for deoxythymidine and deoxycytidine, respectively.

Polypeptide Compositions

The specific deletion markers in Table 1 correspond to open reading frames of the *M. tb* genome, and therefore encode a polypeptide. The subject markers may be employed for synthesis of a complete protein, or polypeptide fragments thereof, particularly fragments corresponding to functional domains; binding sites; etc.; and including fusions of the subject polypeptides to other proteins or parts thereof. For expression, an expression cassette may be employed, providing for a transcriptional and translational initiation region, which may be inducible or constitutive, where the coding region is operably linked under the transcriptional control of the transcriptional initiation region, and a transcriptional and translational termination region. Various transcriptional initiation regions may be employed that are functional in the expression host.

The polypeptides may be expressed in prokaryotes or eukaryotes in accordance with conventional ways, depending upon the purpose for expression. For large scale production of the protein, a unicellular organism, such as *E. coli, B. subtilis, S. cerevisiae,* or cells of a higher organism such as vertebrates, particularly mammals, e.g. COS 7 cells, may be used as the expression host cells. Small peptides can also be synthesized in the laboratory.

With the availability of the polypeptides in large amounts, by employing an expression host, the polypeptides may be isolated and purified in accordance with conventional ways. A lysate may be prepared of the expression host and the lysate purified using HPLC, exclusion chromatography, gel electrophoresis, affinity chromatography, or other purification technique. The purified polypeptide will generally be at least about 80% pure, preferably at least about 90% pure, and may be up to and including 100% pure. Pure is intended to mean free of other proteins, as well as cellular debris.

The polypeptide is used for the production of antibodies, where short fragments provide for antibodies specific for the particular polypeptide, and larger fragments or the entire protein allow for the production of antibodies over the surface of the polypeptide. Antibodies may be raised to isolated peptides corresponding to particular domains, or to the native protein.

Antibodies are prepared in accordance with conventional ways, where the expressed polypeptide or protein is used as an immunogen, by itself or conjugated to known immunogenic carriers, e.g. KLH, pre-S HBsAg, other viral or eukaryotic proteins, or the like. Various adjuvants may be employed, with a series of injections, as appropriate. For monoclonal antibodies, after one or more booster injections, the spleen is isolated, the lymphocytes immortalized by cell fusion, and then screened for high affinity antibody binding. The immortalized cells, i.e. hybridomas, producing the desired antibodies may then be expanded. For further description, see *Monoclonal Antibodies: A Laboratory Manual*, Harlow and Lane eds., Cold Spring Harbor Laboratories, Cold Spring Harbor, N.Y. 1988. If desired, the mRNA encoding the heavy and light chains may be isolated and mutagenized by cloning in *E. coli*, and the heavy and light chains mixed to further enhance the affinity of the antibody. Alternatives to in vivo immunization as a method of raising antibodies include binding to phage "display" libraries, usually in conjunction with in vitro affinity maturation.

The antibody may be produced as a single chain, instead of the normal multimeric structure. Single chain antibodies are described in Jost et al. (1994) *J.B.C.* 269:26267–73, and others. DNA sequences encoding the variable region of the heavy chain and the variable region of the light chain are ligated to a spacer encoding at least about 4 amino acids of small neutral amino acids, including glycine and/or serine. The protein encoded by this fusion allows assembly of a functional variable region that retains the specificity and affinity of the original antibody.

Use of Deletion Markers in Identification of Mycobacteria

The deletions provided in Table 1 are useful for the identification of a mycobacterium as (a) variants of *M. tb.* (b) isolates of BCG (c) *M. bovis* strains or (d) carrying the identified mycobacterial bacteriophage, depending on the specific marker that is chosen. Such screening is particularly useful in determining whether a particular infection or isolate is pathogenic. The term mycobacteria may refer to any member of the family Mycobacteriacaeae, including *M. tuberculosis, M. avium complex, M. kansasii, M. scrofulaceum, M. bovis* and *M. leprae.*

Means of detecting deletions are known in the art. Deletions may be identified through the absence or presence of the sequences in mRNA or genomic DNA, through analysis of junctional regions that flank the deletion, or detection of the gene product, or, particularly relating to the tuberculin skin test, by identification of antibodies that react with the encoded gene product.

While deletions can be easily determined by the absence of hybridization, in many cases it is desirable to have a positive signal, in order to minimize artifactual negative readings. In such cases the deletions may be detected by designing a primer that flanks the junction formed by the deletion. Where the deletion is present, a novel sequence is formed between the flanking regions, which can be detected by hybridization. Preferably such a primer will be sufficiently short that it will only hybridize to the junction, and will fail to form stable hybrids with either of the separate parts of the junction.

Diagnosis is performed by protein, DNA or RNA sequence and/or hybridization analysis of any convenient sample, e.g. cultured mycobacteria, biopsy material, blood sample, etc. Screening may also be based on the functional or antigenic characteristics of the protein. Immunoassays designed to detect the encoded proteins from deleted sequences may be used in screening.

A number of methods are available for analyzing nucleic acids for the presence of a specific sequence. Where large amounts of DNA are available, genomic DNA is used directly. Alternatively, the region of interest is cloned into a suitable vector and grown in sufficient quantity for analysis. The nucleic acid may be amplified by conventional techniques, such as the polymerase chain reaction (PCR), to provide sufficient amounts for analysis. The use of the polymerase chain reaction is described in Saiki, et al. (1985) *Science* 239:487, and a review of current techniques may be found in Sambrook, et al. *Molecular Cloning: A Laboratory Manual,* CSH Press 1989, pp.14.2–14.33. Amplification may also be used to determine whether a polymorphism is present, by using a primer that is specific for the polymorphism. Alternatively, various methods are known in the art that utilize oligonucleotide ligation, for examples see Riley et al. (1990) *N.A.R.* 18:2887–2890; and Delahunty et al. (1996) *Am. J. Hum. Genet.* 58:1239–1246.

A detectable label may be included in an amplification reaction. Suitable labels include fluorochromes, e.g. fluorescein isothiocyanate (FITC), rhodamine, Texas Red, phycoerythrin, allophycocyanin, 6-carboxyfluorescein (6-FAM), 2',7'-dimethoxy-4',5'-dichloro-6-carboxyfluorescein (JOE), 6-carboxy-X-rhodamine (ROX), 6-carboxy-2',4',7!,4,7-hexachlorofluorescein (HEX), 5-carboxyfluorescein (5-FAM) or N,N,N',N'-tetramethyl-6-carboxyrhodamine (TAMRA), radioactive labels, e.g. $^{32}P$, $^{35}S$, $^{3}H$; etc. The label may be a two stage system, where the amplified DNA is conjugated to biotin, haptens, etc. having a high affinity binding partner, e.g. avidin, specific antibodies, etc., where the binding partner is conjugated to a detectable label. The label may be conjugated to one or both of the primers. Alternatively, the pool of nucleotides used in the amplification is labeled, so as to incorporate the label into the amplification product.

The sample nucleic acid, e.g. amplified or cloned fragment, is analyzed by one of a number of methods known in the art. The nucleic acid may be sequenced by dideoxy or other methods, and the sequence of bases compared to the deleted sequence. Hybridization with the variant sequence may also be used to determine its presence, by Southern blots, dot blots, etc. The hybridization pattern of a control and variant sequence to an array of oligonucleotide probes immobilized on a solid support, as described in U.S. Pat. No. 5,445,934, or in WO95/35505, may also be used as a means of detecting the presence of variable sequences. Single strand conformational polymorphism (SSCP) analysis, denaturing gradient gel electrophoresis (DGGE), mismatch cleavage detection, and heteroduplex analysis in gel matrices are used to detect conformational changes created by DNA sequence variation as alterations in electrophoretic mobility. Alternatively, where a polymorphism creates or destroys a recognition site for a restriction endonuclease (restriction fragment length polymorphism, RFLP), the sample is digested with that endonuclease, and the products size fractionated to determine whether the fragment was digested. Fractionation is performed by gel or capillary electrophoresis, particularly acrylamide or agarose gels.

The hybridization pattern of a control and variant sequence to an array of oligonucleotide probes immobilized on a solid support, as described in U.S. Pat. No. 5,445,934, or in WO95/35505, may be used as a means of detecting the presence or absence of deleted sequences. In one embodiment of the invention, an array of oligonucleotides is provided, where discrete positions on the array are complementary to at least a portion of *M. tb.* genomic DNA, usually comprising at least a portion from the identified open reading frames. Such an array may comprise a series of oligonucleotides, each of which can specifically hybridize to a nucleic acid, e.g. mRNA, cDNA, genomic DNA, etc.

Deletions may also be detected by amplification. In an embodiment of the invention, sequences are amplified that include a deletion junction, i.e. where the amplification primers hybridize to a junction sequence. In a nucleic acid sample where the marker sequence is deleted, a junction will be formed, and the primer will hybridize, thereby allowing amplification of a detectable sequence. In a nucleic acid sample where the marker sequence is present, the primer will not hybridize, and no amplification will take place. Alternatively, amplification primers may be chosen such that amplification of the target sequence will only take place where the marker sequence is present. The amplification products may be separated by size using any convenient method, as known in the art, including gel electrophoresis, chromatography, capillary electrophoresis, density gradient fractionation, etc.

In addition to the detection of deletions by the detection of junctions sequences, or detection of the marker sequences themselves, one may determine the presence or absence of the encoded protein product. The specific deletions in Table 1 correspond to open reading frames of the *M. tb* genome, and therefore encode a polypeptides. Polypeptides are detected by means known in the art, including determining the presence of the specific polypeptide in a sample through biochemical, functional or immunological characterization. The detection of antibodies in patient serum that react with a polypeptide is of particular interest.

Immunization with BCG typically leads to a positive response against tuberculin antigens in a skin test. In people who have been immunized, which includes a significant proportion of the world population, it is therefore difficult to determine whether a positive test is the result of an immune reaction to the BCG vaccine, or to an ongoing *M. tb.* infection. The subject invention has provided a number of open reading frame sequences that are present in *M. tb* isolates, but are absent in BCG. As a primary or a secondary screening method, one may test for immunoreactivity of the patient with the polypeptides encoded by such deletion markers. Diagnosis may be performed by a number of methods. The different methods all determine the presence of an immune response to the polypeptide in a patient, where a positive response is indicative of an *M. tb* infection. The immune response may be determined by determination of antibody binding, or by the presence of a response to intradermal challenge with the polypeptide.

In one method, a dose of the deletion marker polypeptide, formulated as a cocktail of proteins or as individual protein species, in a suitable medium is injected subcutaneously into the patient. The dose will usually be at least about 0.05 $\mu$g of protein, and usually not more than about 5 $\mu$g of protein. A control comprising medium alone, or an unrelated protein will be injected nearby at the same time. The site of injection is examined after a period of time for the presence of a wheal. The wheal at the site of polypeptide injection is compared to that at the site of the control injection, usually by measuring the size of the wheal. The skin test readings may be assessed by a variety of objective grading systems. A positive result for the presence of an allergic condition will show an increased diameter at the site of polypeptide injection as compared to the control, usually at least about 50% increase in size, more usually at least 100% increase in size.

An alternative method for diagnosis depends on the in vitro detection of binding between antibodies in a patient sample and the subject polypeptides, either as a cocktail or as individual protein species, where the presence of specific binding is indicative of an infection. Measuring the concentration of polypeptide specific antibodies in a sample or fraction thereof may be accomplished by a variety of specific assays. In general, the assay will measure the reactivity between a patient sample, usually blood derived, generally in the form of plasma or serum. The patient sample may be used directly, or diluted as appropriate, usually about 1:10 and usually not more than about 1:10,000. Immunoassays may be performed in any physiological buffer, e.g. PBS, normal saline, HBSS, dPBS, etc.

In a preferred embodiment, a conventional sandwich type assay is used. A sandwich assay is performed by first attaching the polypeptide to an insoluble surface or support. The polypeptide may be bound to the surface by any convenient means, depending upon the nature of the surface, either directly or through specific antibodies. The particular manner of binding is not crucial so long as it is compatible with the reagents and overall methods of the invention. They may be bound to the plates covalently or non-covalently, preferably non-covalently. Samples, fractions or aliquots thereof are then added to separately assayable supports (for example, separate wells of a microtiter plate) containing support-bound polypeptide. Preferably, a series of standards, containing known concentrations of antibodies is assayed in parallel with the samples or aliquots thereof to serve as controls.

Immune specific receptors may be labeled to facilitate direct, or indirect quantification of binding. Examples of labels which permit direct measurement of second receptor binding include radiolabels, such as $^{3}H$ or $^{125}I$, fluorescers, dyes, beads, chemilumninescers, colloidal particles, and the like. Examples of labels which permit indirect measurement of binding include enzymes where the substrate may provide for a colored or fluorescent product. In a preferred embodiment, the second receptors are antibodies labeled with a covalently bound enzyme capable of providing a detectable product signal after addition of suitable substrate. Examples of suitable enzymes for use in conjugates include horseradish peroxidase, alkaline phosphatase, malate dehydrogenase and the like. Where not commercially available, such antibody-enzyme conjugates are readily produced by techniques known to those skilled in the art.

In some cases, a competitive assay will be used. In addition to the patient sample, a competitor to the antibody is added to the reaction mix. The competitor and the antibody compete for binding to the polypeptide. Usually, the competitor molecule will be labeled and detected as previously described, where the amount of competitor binding will be proportional to the amount of Immune present. The concentration of competitor molecule will be from about 10 times the maximum anticipated Immune concentration to about equal concentration in order to make the most sensitive and linear range of detection.

Alternatively, antibodies may be used for direct determination of the presence of the deletion marker polypeptide. Antibodies specific for the subject deletion markers as previously described may be used in screening immunoassays. Samples, as used herein, include microbial cultures, biological fluids such as tracheal lavage, blood, etc. Also included in the term are derivatives and fractions of such fluids. Diagnosis may be performed by a number of methods. The different methods all determine the absence or presence of polypeptides encoded by the subject deletion markers. For example, detection may utilize staining of mycobacterial cells or histological sections, performed in accordance with conventional methods. The antibodies of interest are added to the cell sample, and incubated for a period of time sufficient to allow binding to the epitope, usually at least about 10 minutes. The antibody may be labeled with radioisotopes, enzymes, fluorescers, chemiluminescers, or other labels for direct detection. Alternatively, a second stage antibody or reagent is used to amplify the signal. Such reagents are well known in the art. For example, the primary antibody may be conjugated to biotin, with horseradish peroxidase-conjugated avidin added as a second stage reagent. Final detection uses a substrate that undergoes a color change in the presence of the peroxidase. The absence or presence of antibody binding may be determined by various methods, including microscopy, radiography, scintillation counting, etc.

An alternative method for diagnosis depends on the in vitro detection of binding between antibodies and the subject polypeptides in solution, e.g. a cell lysate. Measuring the concentration of binding in a sample or fraction thereof may be accomplished by a variety of specific assays. A conventional sandwich type assay may be used. For example, a sandwich assay may first attach specific antibodies to an insoluble surface or support. The particular manner of binding is not crucial so long as it is compatible with the reagents and overall methods of the invention. They may be bound to the plates covalently or non-covalently, preferably non-covalently. The insoluble supports may be any compositions to which polypeptides can be bound, which is readily separated from soluble material, and which is otherwise compatible with the overall method. The surface of such supports may be solid or porous and of any convenient shape. Examples of suitable insoluble supports to which the receptor is bound include beads, e.g. magnetic beads, membranes and microtiter plates. These are typically made of glass, plastic (e.g. polystyrene), polysaccharides, nylon or nitrocellulose. Microtiter plates are especially convenient because a large number of assays can be carried out simultaneously, using small amounts of reagents and samples.

Samples are then added to separately assayable supports (for example, separate wells of a microtiter plate) containing antibodies. Preferably, a series of standards, containing known concentrations of the polypeptides is assayed in parallel with the samples or aliquots thereof to serve as controls. Preferably, each sample and standard will be added to multiple wells so that mean values can be obtained for each. The incubation time should be sufficient for binding, generally, from about 0.1 to 3 hr is sufficient. After incubation, the insoluble support is generally washed of non-bound components. Generally, a dilute non-ionic detergent medium at an appropriate pH, generally 7–8, is used as a wash medium. From one to six washes may be employed, with sufficient volume to thoroughly wash non-specifically bound proteins present in the sample.

After washing, a solution containing a second antibody is applied. The antibody will bind with sufficient specificity such that it can be distinguished from other components present. The second antibodies may be labeled to facilitate direct, or indirect quantification of binding. Examples of labels that permit direct measurement of second receptor binding include radiolabels, such as $^{3}H$ or $^{125}I$, fluorescers, dyes, beads, chemilumninescers, colloidal particles, and the like. Examples of labels which permit indirect measurement of binding include enzymes where the substrate may provide for a colored or fluorescent product. In a preferred embodiment, the antibodies are labeled with a covalently bound enzyme capable of providing a detectable product signal after addition of suitable substrate. Examples of suitable enzymes for use in conjugates include horseradish peroxidase, alkaline phosphatase, malate dehydrogenase and the like. Where not commercially available, such antibody-enzyme conjugates are readily produced by techniques known to those skilled in the art. The incubation time should be sufficient for the labeled ligand to bind available molecules. Generally, from about 0.1 to 3 hr is sufficient, usually 1 hr sufficing.

After the second binding step, the insoluble support is again washed free of non-specifically bound material. The signal produced by the bound conjugate is detected by conventional means. Where an enzyme conjugate is used, an appropriate enzyme substrate is provided so a detectable product is formed.

Other immunoassays are known in the art and may find use as diagnostics. Ouchterlony plates provide a simple determination of antibody binding. Western blots may be performed on protein gels or protein spots on filters, using a detection system specific for the polypeptide, conveniently using a labeling method as described for the sandwich assay.

Recombinant Mycobacterium

Mycobacterium, particularly those of the *M. tuberculosis* complex, are genetically engineered to contain specific deletions or insertions corresponding to the identified genetic markers. In particular, attenuated BCG strains are modified to introduce deleted genes encoding sequences important in the establishment of effective immunity. Alternatively, *M. bovis* or *M. tuberculosis* are modified by homologous recombination to create specific deletions in sequences that determine virulence, i.e. the bacteria are attenuated through recombinant techniques.

In order to stably introduce sequences into BCG, the *M. tb* open reading frame corresponding to one of the deletions in Table 1 is inserted into a vector that is maintained in *M. bovis* strains. Preferably, the native 5' and 3' flanking sequences are included, in order to provide for suitable regulation of transcription and translation. However, in special circumstances, exogenous promoters and other regulatory regions may be included. Vectors and methods of transfection for BCG are known in the art. For example, U.S. Pat. No. 5,776,465, herein incorporated by reference, describes the introduction of exogenous genes into BCG.

In one embodiment of the invention, the complete deleted region is replaced in BCG. The junctions of the deletion are determined as compared to a wild type *M. tb.* or *M. bovis* sequence, for example as set forth in the experimental section. The deleted region is cloned by any convenient method, as known in the art, e.g. PCR amplification of the region, restriction endonuclease digestion, chemical synthesis, etc. Preferably the cloned region will further comprise flanking sequences of a length sufficient to induce homologous recombination, usually at least about 25 nt, more usually at least about 100 nt, or greater. Suitable vectors and methods are known in the art, for an example, see Norman et al. (1995) *Mol. Microbiol.* 16:755–760.

In an alternative embodiment, one or more of the deletions provided in Table 1 are introduced into a strain of *M. tuberculosis* or *M. bovis* . Preferably such a strain is reduced in virulence, e.g. H37Ra, etc. Methods of homologous recombination in order to effect deletions in mycobacteria are known in the art, for example see Norman et al., supra.; Ganjam et al. (1991) *P.N.A.S.* 88:5433–5437; and Aldovini et al. (1993) *J. Bacteriol.* 175:7282–7289. Deletions may comprise an open reading frame identified in Table 1, or may extend to the full deletion, i.e. extending into flanking regions, and may include multiple open reading frames.

The ability of the genetically altered mycobacterium to cause disease may be tested in one or more experimental models. For example, *M. tb.* is known to infect a variety of animals, and cells in culture. In one assay, mammalian macrophages, preferably human macrophages, are infected. In a comparison of virulent, avirulent and attenuated strains of the *M. tuberculosis* complex, alveolar or peripheral blood monocytes are infected at a 1:1 ratio (Silver et al. (1998) *Infect Immun* 66(3):1190–1199; Paul et al. (1996) *J Infect Dis* 174(1):105–112). The percentages of cells infected by the strains and the initial numbers of intracellular organisms are equivalent, as were levels of monocyte viability up to 7 days following infection. However, intracellular growth reflects virulence, over a period of one or more weeks. Mycobacterial growth may be evaluated by acid-fast staining, electron microscopy, and colony-forming units (cfu) assays. Monocyte production of tumor necrosis factor alpha may also be monitored as a marker for virulence.

Other assays for virulence utilize animal models. The *M. tb.* complex bacteria are able to infect a wide variety of animal hosts. One model of particular interest is cavitary tuberculosis produced in rabbits by aerosolized virulent tubercle bacilli (Converse et al. (1996) *Infect Immun* 64(11):4776–4787). In liquefied caseum, the tubercle bacilli grow extracellularly for the first time since the onset of the disease and can reach such large numbers that mutants with antimicrobial resistance may develop. From a cavity, the bacilli enter the bronchial tree and spread to other parts of the lung and also to other people. Of the commonly used laboratory animals, the rabbit is the only one in which cavitary tuberculosis can be readily produced.

Vaccines may be formulated according to methods known in the art. Vaccines of the modified bacteria are administered to a host which may be exposed to virulent tuberculosis. In many countries where tuberculosis is endemic, vaccination may be performed at birth, with additional vaccinations as necessary. The compounds of the present invention are administered at a dosage that provides effective immunity while minimizing any side-effects. It is contemplated that the composition will be obtained and used under the guidance of a physician.

Conventional vaccine strains of BCG may be formulated in a combination vaccine with polypeptides identified in the present invention and produced as previously described, in order to improve the efficacy of the vaccine.

Various methods for administration may be employed. The formulation may be injected intramuscularly, intravascularly, subcutaneously, etc. The dosage will be conventional. The bacteria can be formulated into pharmaceutical compositions by combination with appropriate, pharmaceutically acceptable carriers or diluents, and may be formulated into preparations in semi-solid or liquid forms, such as solutions, injections, etc. The following methods and excipients are merely exemplary and are in no way limiting.

The modified bacteria can be formulated into preparations for injections by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives. Unit dosage forms for injection or intravenous administration may comprise the bacteria of the present invention in a composition as a solution in sterile water, normal saline or another pharmaceutically acceptable carrier.

The term "unit dosage form, " as used herein, refers to physically discrete units suitable as unitary dosages for human and animal subjects, each unit containing a predetermined quantity of vaccine, calculated in an amount sufficient to produce the desired effect in association with a pharmaceutically acceptable diluent, carrier or vehicle. The specifications for the unit dosage forms of the present invention depend on the particular bacteria employed and the effect to be achieved, and the pharmacodynamics associated with each complex in the host.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

The following examples are put forth so as to provide those of ordinary skill in the art with a complete disclosure and description of how to make and use the subject invention, and are not intended to limit the scope of what is regarded as the invention. Efforts have been made to ensure accuracy with respect to the numbers used (e.g. amounts, temperature, concentrations, etc.) but some experimental errors and deviations should be allowed for. Unless otherwise indicated, parts are parts by weight, molecular weight is average molecular weight, temperature is in degrees centigrade; and pressure is at or near atmospheric.

EXPERIMENTAL

Methods:

The technical methods used begin with extraction of whole genomic DNA from bacteria grown in culture.

Day 1

Inoculate culture medium of choice (LJ/7H9) and incubate at 35° C. until abundant growth. Dispense 500 µl 1× TE into each tube. (If DNA is in liquid medium, no TE needed.)

Transfer loopful (sediment) of cells into microcentrifuge tube containing 500 μl of 1*TE. If taking DNA from liquid medium, let cells collect in bottom of flask. Pipette cells (about 1 ml) into tube. Heat 20 min at 80° C. to kill cells, centrifuge, resuspend in 500 μl of 1*TE. Add 50 μl of 10 mg/ml lysozyme, vortex, incubate overnight at 37° C.

Day 2

Add 70 μl of 10% SDS and 10 μl proteinase K, vortex and incubate 20 min. at 65° C. Add 100 μl of 5M NaCl. Add 100 μl of CTAB/NaCl solution, prewarmed at 65° C. Vortex until liquid content white ("milky"). Incubate 10 min at 65° C. Outside of hood, prepare new microcentrifuge tubes labeled with culture # on top, and culture #, tube #, date on side. Add 550 μl isopropanol to each and cap. Back in the hood, add 750 μl of chloroform/isoamyl alcohol, vortex for 10 sec. Centrifuge at room temp for 5 min. at 12,000 g. Transfer aqueous supernatant in 180 μl amounts to new tube using pipetter, being careful to leave behind solids and non-aqueous liquid. Place 30 min at −20 C. Spin 15 min at room temp in a microcentrifuge at 12,000 g. Discard supernatant; leave about 20 μl above pellet. Add 1 ml cold 70% ethanol and turn tube a few times upside down. Spin 5 min at room temp in a microcentrifuge. Discard supernatant; leave about 20 μl above the pellet. Spin 1 min in a microcentrifuge and discard cautiously the last 20 μl supernatant just above the pellet using a pipetter (P-20). Be sure that all traces of ethanol are removed. Allow pellet to dry at room temp for 10 min or speed vac 2–3 min. (Place open tubes in speed vac, close lid, start rotor, turn on vacuum. After 3 min. push red button, turn off vacuum, turn off rotor. Check if pellets are dry by flicking tube to see if pellet comes away from side of tube.) Redissolve the pellet in 20–50 μl of ddH2O. Small pellets get 20, regular sized get 30 and very large get 50. DNA can be stored at 4° C. for further use.

DNA array: was made by spotting DNA fragments onto glass microscope slides which were pretreated with poly-L-lysine. Spotting onto the array was accomplished by a robotic arrayer. The DNA was cross-linked to the glass by ultraviolet irradiation, and the free poly-L-lysine groups were blocked by treatment with 0.05% succinic anhydride, 50% 1-methyl-2-pyrrolidinone and 50% borate buffer.

The majority of spots on the array were PCR-derived products, produced by selecting over 9000 primer pairs designed to amplify the predicted open reading frames of the sequences strain H37Rv (ftp.sanger.ac.uk/pub/TB.seq). Some internal standards and negative control spots including plasmid vectors and non-*M.tb.* DNA were also on the array.

Therefore, with the preparation for an array that contained the whole genome of *Mycobacterium tuberculosis*, we compared BCG-Connaught to *Mycobacterium tuberculosis*, using the array for competitive hybridization. The protocol follows:

DNA labeling protocol. Add 4 μg DNA in 20 μl H$_2$O, 2 ml dN10N6 and 36 μl H$_2$O. 2 ml DNA spike for each DNA sample, for total of 60 μl. Boil 3 minutes to denature DNA, then snap cool on ice water bath. Add 1 μl dNTP (5mM ACG), 10 μl 10 buffer, 4 μl Klenow, 22 μl H$_2$O to each tube. Add 3 μl of Cy3 or Cy5 dUTP, for total of 100 μl. Incubate 3 hours at 37° C. Add 11 μl 3M NaAc, 250 μl 100% EtOH to precipitate, store O/N at −20° C. Centrifuge genomic samples 30 minutes at 13K to pellet precipitate. Discard supernatant, add 70% EtOH, spin 15 minutes, discard sup and speed-vac to dry. This provides DNA for two experiments.

DNA hybridization to microarray. protocol. Resuspend the labeled DNA in 11 μl H$_2$O (for 2 arrays). Run out 1 μl DNA on a 1.5% agarose gel to document sample to be hybridized. Of the remaining 10 μl of solution, half will be used for this hyb, and half will be left for later date. Take 5 μl of solution Cy3 and add to same amount of Cy5 solution, for total volume 10 μl mixed labeled DNA. Add 1 μl tRNA, 2.75 μl 20×SSC, 0.4 μl SDS, for total volume 14.1 μl. Place on slide at array site, cover with 22 mm coverslip, put slide glass over and squeeze onto rubber devices, then hybridize 4 hours at 65° C. After 4 hours, remove array slides from devices, leave coverslip on, and dip in slide tray into wash buffer consisting of 1×SSC with 0.05% SDS for about 2 minutes. Cover slip should fall off into bath. After 2 minutes in wash buffer, dip once into a bath with 0.06×SSC, then rinse again in 0.06×SSC in separate bath. Dry slides in centrifuge about 600 rpm. They are now ready for scanning.

Fluorescence scanning and data acquisition. Fluorescence scanning was set for 20 microns/pixel and two readings were taken per pixel. Data for channel 1 was set to collect fluorescence from Cy3 with excitation at 520 nm and emission at 550–600 nm. Channel 2 collected signals excited at 647 nm and emitted at 660–705 nm, appropriate for Cy5. No neutral density filters were applied to the signal from either channel, and the photomultiplier tube gain was set to 5. Fine adjustments were then made to the photomultiplier gain so that signals collected from the two spots containing genomic DNA were equivalent.

To analyze the signal from each spot on the array, a 14×14 grid of boxes was applied to the data collected from the array such that signals from within each box were integrated and a value was assigned to the corresponding spot. A background value was obtained for each spot by integrating the signals measured 2 pixels outside the perimeter of the corresponding box. The signal and background values for each spot were imported into a spreadsheet program for further analysis. The background values were subtracted from the signals and a factor of 1.025 was applied to each value in channel 2 to normalize the data with respect to the signals from the genomic DNA spots.

Because the two samples are labeled with different fluorescent dyes, it is possible to determine that a spot of DNA on the array has hybridized to Mycobacterium tuberculosis (green dye) and not to BCG (red dye), thus demonstrating a likely deletion from the BCG genome.

However, because the array now contains spots representing 4000 spots, one may expect up to 100 spots with hybridization two standard deviations above or below the mean. Consequently, we have devised a screening protocol, where we look for mismatched hybridization in two consecutive genes on the genome. Therefore, we are essentially looking only for deletions of multiple genes at this point.

To confirm that a gene or group of genes is deleted, we perform Southern hybridization, employing a separate probe from the DNA on the array. Digestions of different mycobacterium DNAs are run on an agarose gel, and transferred to membranes. The membranes can be repeatedly used for probing for different DNA sequences. For the purposes of this project, we include DNA from the reference strain of *Mycobacterium tuberculosis* (H37Rv), from other laboratory strains, such as H37Ra, the O strain, from clinical isolates, from the reference strain of *Mycobacterium bovis*, and from different strains of *Mycobacterium bovis* BCG.

Once a deletion is confirmed by Southern hybridization, we then set out to characterize the exact genomic location. This is done by using polymerase chain reaction, with primers designed to be close to the edges of the deletion, see Talbot (1997) *J Clin Micro.* 35: 566–9

Primers have been chosen to amplify across the deleted region. Only in the absence of this region does one obtain an amplicon. PCR products were examined by electrophoresis (1.5% agarose) and ethidium bromide staining.

Once a short amplicon is obtained, this amplicon is then sequenced. A search of the genome database is performed to determine whether the sequence is exactly identical to one part of the *Mycobacterium tuberculosis* genome, and that the next part of the amplicon is exactly identical to another part of the Mycobacterium tuberculosis genome. This permits precise identification of the site of deletion.

Below follows an example of the kind of report obtained:
rd6 bridging PCR, blast search of sequence

```
emb |Z79701 |MTCY277 Mycobacterium tuberculosis cosmid Y277
Length = 38,908
Plus Strand HSPs:
Score = 643 (177.7 bits), Expect = 1.6e-54, Sum P(2) = 1.6e-54
Identities = 129/131 (98%), Positives = 129/131 (98%), Strand = Plus/Plus Query SEQ ID NO:130:      12 ANTAGTAATGTGCGAGCTGAGCGATGTCGCCGCTCCCAAAAATTACCAATGGTTNGGTCA 71
                             | |||||||||||||||||||||||||||||||||||||||||||||||||||| |||||
Sbjct SEQ ID NO:131:   24784 AGTAGTAATGTGCGAGCTGAGCGATGTCGCCGCTCCCAAAAATTACCAATGGTTTGGTCA Query SEQ ID NO:132:      72 TGACGCCTTCCTAACCAGAATTGTGAATTCATACAAGCCGTAGTCGTGCAGAAGCGCAAC
                             ||||||||||||||||||||||||||||||||||||||||||||||||||||||||||||
Sbjct SEQ ID NO:133:   24844 TGACGCCTTCCTAACCAGAATTGTGAATTCATACAAGCCGTAGTCGTGCAGAAGCGCAAC Query SEQ ID NO:134:     132 ACTCTTGGAGT 142
                             |||||||||||
Sbjct SEQ ID NO:135:   24904 ACTCTTGGAGT 24914

Score = 224 (61.9 bits), Expect = 1.6e-54, Sum P(2) = 1.6e-54
Identities = 46/49 (93%), Positives = 46/49 (93%), Strand = Plus/Plus Query SEQ ID NO:136:     141 GTGGCCTACAACGGNGCTCTCCGNGGCGCGGGCGTACCGGATATCTTAG 189
                             | ||||||||||||| ||||||| ||||||||||||||||||||||||
Sbjct SEQ ID NO:137:   37645 GCGGCCTACAACGGCGCTCTCCGCGGCGCGGGCGTACCGGATATCTTAG 37693
```

This process is repeated with each suggested deletion, beginning with the three previously described deletions to serve as controls. Sixteen deletions have been identified by these methods, and are listed in Table 1.

It is to be understood that this invention is not limited to the particular methodology, protocols, formulations and reagents described, as such may, of course, vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "and", and "the " include plural referents unless the context clearly dictates otherwise. Thus, for example, reference to "a complex " includes a plurality of such complexes and reference to "the formulation " includes reference to one or more formulations and equivalents thereof known to those skilled in the art, and so forth.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

All publications mentioned herein are incorporated herein by reference for the purpose of describing and disclosing, for example, the cell lines, constructs, and methodologies that are described in the publications which might be used in connection with the presently described invention. The publications discussed above and throughout the text are provided solely for their disclosure prior to the filing date of the present application. Nothing herein is to be construed as an admission that the inventors are not entitled to antedate such disclosure by virtue of prior invention.

What is claimed is:

1. A method of distinguishing whether a patient has been exposed to a virulent strain of the *M. tuberculosis* complex, the method comprising:

contacting said patient or a sample obtained therefrom with a polypeptide encoded by the open reading frame Rv2073c (SEQ ID NO: 82); and determining the presence of an immune reaction to said polypeptide, wherein a positive response is indicative of exposure to a virulent strain of the *M. tuberculosis* complex.

2. The method of claim 1, wherein the contacting step comprises sub-cutaneous injection of said polypeptide.

3. The method of claim 1, wherein the contacting step is performed in vitro and said sample comprises a blood sample or derivative thereof.

4. The method according to claim 2, wherein said polypeptide is injected at a dose of from 0.05 µg to 5 µg.

5. The method according to claim 2, wherein the site of injection is examined for the presence of a wheat, indicative of said positive response.

* * * * *

UNITED STATES PATENT AND TRADEMARK OFFICE
CERTIFICATE OF CORRECTION

PATENT NO. : 6,291,190 B1  Page 1 of 1
DATED : September 18, 2001
INVENTOR(S) : Behr et al.

It is certified that error appears in the above-identified patent and that said Letters Patent is hereby corrected as shown below:

<u>Column 148, claim 5,</u>
Line 29, please replace the word "wheat" with the word -- wheal --.

Signed and Sealed this

Twenty-sixth Day of March, 2002

Attest:

*Attesting Officer*

JAMES E. ROGAN
*Director of the United States Patent and Trademark Office*

UNITED STATES PATENT AND TRADEMARK OFFICE
CERTIFICATE OF CORRECTION

PATENT NO.   : 6,291,190 B1
DATED        : September 18, 2001
INVENTOR(S)  : Behr, Marcel et al.

It is certified that error appears in the above-identified patent and that said Letters Patent is hereby corrected as shown below:

<u>Column 1,</u>
Line 5, please insert the following:
-- This invention was made with Government support under contract AI01137, AI35969 awarded by the National Institutes of Health. The Government has certain rights in this invention. --

Signed and Sealed this

Fifteenth Day of June, 2004

JON W. DUDAS
*Acting Director of the United States Patent and Trademark Office*